United States Patent
Chen et al.

(10) Patent No.: US 11,219,607 B2
(45) Date of Patent: Jan. 11, 2022

(54) METHODS FOR SUPPRESSING CANCER-RELATED CACHEXIA

(71) Applicant: Ohio State Innovation Foundation, Columbus, OH (US)

(72) Inventors: Ching-Shih Chen, Upper Arlington, OH (US); Tanios Bekaii-Saab, Upper Arlington, OH (US); Denis Guttridge, Upper Arlington, OH (US); Guido Marcucci, Powell, OH (US); Samuel Kulp, Hiliard, OH (US); Yu-Chou Tseng, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 223 days.

(21) Appl. No.: 14/547,771

(22) Filed: Nov. 19, 2014

(65) Prior Publication Data

US 2015/0150832 A1    Jun. 4, 2015

Related U.S. Application Data

(60) Provisional application No. 61/906,738, filed on Nov. 20, 2013.

(51) Int. Cl.
*A61K 31/16* (2006.01)
*A61K 31/166* (2006.01)
*A61K 31/167* (2006.01)

(52) U.S. Cl.
CPC ............ *A61K 31/16* (2013.01); *A61K 31/166* (2013.01); *A61K 31/167* (2013.01)

(58) Field of Classification Search
CPC .... A61K 31/16; A61K 31/166; A61K 31/167; A61P 7/00; A61P 43/00; A61P 35/00; A61P 3/00; A61P 21/00
See application file for complete search history.

(56) References Cited

U.S. PATENT DOCUMENTS

| | | | |
|---|---|---|---|
| 2006/0229237 A1* | 10/2006 | Chung et al. | 514/9 |
| 2006/0275370 A1 | 12/2006 | Chung et al. | |
| 2015/0296757 A1 | 10/2015 | Schule et al. | |

FOREIGN PATENT DOCUMENTS

| | | | | |
|---|---|---|---|---|
| GN | 1843508 A | 10/2006 | | |
| WO | 2007/147868 A2 | 12/2007 | | |
| WO | WO 2012009475 A1 * | 1/2012 | | A61K 31/00 |
| WO | 2013/080120 A1 | 6/2013 | | |
| WO | 2014/068033 A2 | 5/2014 | | |
| WO | 2015077353 A1 | 5/2015 | | |

OTHER PUBLICATIONS

Simone, Oncology: Introduction, Cecil Textbook of Medicine, 20th Edition, 1996 vol. 1, pp. 1004-1010.*

(Continued)

*Primary Examiner* — Savitha M Rao
*Assistant Examiner* — Andrew P Lee
(74) *Attorney, Agent, or Firm* — Potomac Law Goup, PLLC

(57) ABSTRACT

Methods of suppressing cachexia in a mammal with cancer comprising administering HDAC inhibitors are provided. Aspects include methods of administering an HDAC class 1 and 2b inhibitor in an amount effective to substantially maintain the mammal's weight compared to a mammal that does receive the HDAC class 1 and 2b inhibitor.

15 Claims, 41 Drawing Sheets

Specification includes a Sequence Listing.

(56) References Cited

OTHER PUBLICATIONS

Thomas, Loss of skeletal muscle mass in aging: Examining the relationship of starvation, sarcopenia and cachexia, Clinical Nutrition, 2007, 26, pp. 389-399 (Year: 2007).*
Thaler, Next generation histone deacetylase inhibitors: the answer to the search for optimized epigenetic therapies?, Expert Opinion on Drug Discovery, 2011, 6(4), pp. 393-404 (Year: 2011).*
International Search Report of corresponding PCT International Patent Application No. PCT/US2014/066435 dated May 13, 2015.
Lu, et al., "Efficacy of a novel histone deacetylase inhibitor in murine models of hepatocellular carcinoma", Hepatology (Baltimore, MD) Oct. 2007, vol. 46, No. 4, pp. 1119-1130.
Tseng, "Abstract 5540: Preclinical investigation of the novel histone deacetylase (HDAC) inhibitor AR-42 in the treatment of cancer-induced cachexia", Apr. 9, 2014.
Kim, et al., "Histone deacetylase inhibitors: molecular mechanisms of action and clinical trials as anti-cancer drugs", American Journal of Translational Research, Feb. 2011, vol. 3, No. 2, pp. 166-179.
Lee, et al., "Histone deacetylase inhibitor AR-42 enhances E7-specific CD8 +T cell-mediated antitumor immunity induced by therapeutic HPV DNA vaccination", Journal of Molecular Medicine (Berlin, Germany), Oct. 2013, vol. 91, No. 10, pp. 1221-1231.
Beharry, et al., "HDAC1 activates FoxO and is both sufficient and required for skeletal muscle atrophy", Journal of Cell Science, Apr. 2014, vol. 127, No. 7, pp. 1441-1453.
Damrauer, et al., "Chemotherapy-induced muscle wasting: association with NF-xB and cancer cachexia", Basic Applied Myology, 2008, vol. 18, No. 5, pp. 139-148.
Prado, et al., "Skeletal muscle anabolism is a side effect of therapy with the MEK inhibitor: selumetinib in patients with cholangiocarcinoma", British Journal of Cancer, 2012, vol. 106, pp. 1583-1586.
Antoun, et al., "Association of Skeletal Muscle Wasting With Treatment With Sorafenib in Patients With Advanced Renal Cell Carcinoma: Results From a Placebo-Controlled Study", Journal of Clinical Oncology, Feb. 10, 2010, vol. 28, No. 6, pp. 1054-1060.
European Communication in European Patent Application No. 14824959.2 dated Jul. 15, 2016.
Written Opinion of corresponding PCT International Patent Application No. PCT/US2014/066435 dated May 13, 2015.
Aulino et al., "Molecular, cellular and physiological characterization of the cancer cachexia-inducing C26 colon carcinoma in mouse," BMC Cancer 10:363 (2010).
Porporato, "Understanding cachexia as a cancer metabolism syndrome," Oncogenesis (2016) 5.
Tsoli et al., "Cancer cachexia: malignant inflammation, tumorkines, and metabolic mayhem," Trends in Endocrinology and Metabolism, Apr. 2013, vol. 24, No. 4.
DeBoer, "Animal models of anorexia and cachexia," Expert Opin Drug Discov. Nov. 1, 2009; 4(11): 1145-1155.
Seto, et al., "A Key Role for Leukemia Inhibitory Factor in C26 Cancer Cachexia," The Journal of Biological Chemistry, Aug. 7, 2015, vol. 290, No. 32, pp. 19976-19986.
Examination Report for European Patent Application No. 14824959.2 dated Jan. 29, 2018.
First Office Action for Chinese Patent Application No. 201480063679.7 dated Jan. 31, 2018 (with machine English language translation).
Subramanian et al., "Clinical Toxicities of Histone Deacetylase Inhibitors", Pharmaceuticals, vol. 3(9), Aug. 26, 2010, pp. 2751-2767.
Tan et al., "Cachexia: prevalence and impact in medicine", Current Opinion in Clinical Nutrition & Metabolic Care, Jul. 2008, vol. 11(4), pp. 400-407.
Valencia et al., "A phase 1 study of AR-42 in patients with advanced solid tumors, including nervous system tumors", Journal of Clinical Oncology, May 2016, vol. 34(15), p. 2558.
Lane et al., "Histone deacetylase inhibitors in cancer therapy," J Clin Oncol., Nov. 10, 2009, vol. 27(32), pp. 5459-5468.
Lucas et al., "The novel deacetylase inhibitor AR-42 demonstrates pre-clinical activity in B-cell malignancies in vitro and in vivo," PLoS One, Jun. 3, 2010, vol. 5(6), art. e10941, pp. 1-10.
Notification of Reasons for Refusal dated Aug. 28, 2018 issued in Japanese Patent Application No. 2016-530241 (with English-language translation).
Office Action and Search Report dated Aug. 31, 2018 issued in Russian Patent Application No. 2016118228 (with English-language translation).
Communication under Rule 71(3) EPC for European Patent Application No. 14824959.2 dated Oct. 29, 2018.
Second Office Action for Chinese Patent Application No. 201480063679.7 dated Oct. 17, 2018.
Office Action dated Jan. 15, 2019 for Russian Patent Application No. 2016118228.
Argilés et al., "Cancer cachexia: understanding the molecular basis," Nature Reviews Cancer, Oct. 9, 2014, vol. 14, pp. 754-762.
Bozzetti, "Forcing the vicious circle: sarcopenia increases toxicity, decreases response to chemotherapy and worsens with chemotherapy," Annals of Oncology, Sep. 2017, vol. 28(9), pp. 2107-2118.
Penna et al., "The Skeletal Muscle as an Active Player Against Cancer Cachexia," Frontiers in Physiology, Feb. 18, 2019, vol. 10(41), pp. 1-15.
Office Action (First Examination Report) dated Apr. 24, 2019 for Australian Patent Application No. 2014353070.
Office Action (First Examination Report) dated Jun. 20, 2019 for Indian Patent Application No. 201617019838.
Office Action dated Jun. 10, 2019 for Mexican Patent Application No. MX/a/2016/006058.
Office Action (Notice to File a Response) dated Nov. 18, 2019 for South Korean Patent Application No. 10-2016-7016307.
Office Action (Second Examination Report) dated Nov. 27, 2019 for Australian Patent Application No. 2014353070.
Office Action (Examination Report) dated Jan. 22, 2021 for Canadian Patent Application No. 2,930,606.

* cited by examiner

Supplementary Table 1. Sequences of primers used for real-time RT-PCR

| Target | Primer pairs (5'→3') | |
| --- | --- | --- |
| ATGL (PNPLA2) | AACACCAGCATCCAGTTCAA | GGTTCAGTAGGCCATTCCTC |
| Atrogin-1 (Fbxo32) | CACATTCTCTCCTGGAAGGGC | TTGATAAAGTCTTGAGGGGAAAGTG |
| Foxo1 | TTCAATTCGCCACAATCTGTCC | GGGTGATTTTCCGCTCTTGC |
| GAPDH | CATGGCCTTCCGTGTTCCTA | GCGGCACGTCAGATCCA |
| IL-6Rα | CTCCCGGTGGCCCAGTACCA | TGCACTGGGGCGAGGACACT |
| Mef2c | GCTGTTCCAGTACGCCAGCAC | AGTGCGTGGGGTGAGTGCATAA |
| MuRF1 (Trim63) | CACGAAGACGAGAAGATCAACATC | AGCCCCAAACACCTTGCA |
| UCP3 | CCAACATCACAAGAAATGC | TACAAACATCATCACGTTCC |

FIG. 8

Table 1. IPA of differentially expressed genes (≥4-fold) related to muscle disease or functions between AR-42- and vehicle-treated C-26 tumor-bearing mice (n = 6)

| RefSeq ID | Gene ID | Log2 fold change | P value | Description | Disease or function annotation |
|---|---|---|---|---|---|
| *Upregulated by AR-42* | | | | | |
| NM_024291 | Ky | 4.3 | 0.0004 | Kyphoscoliosis peptidase | Muscle development |
| NM_010267 | Gdap1 | 4.2 | 0.0004 | Ganglioside-induced differentiation-associated-protein 1 | Muscle atrophy; myopathy |
| NM_013569 | Kcnh2 | 4.1 | 0.0004 | Potassium voltage-gated channel, subfamily H, member 2 | Muscle atrophy; myopathy |
| NM_009608 | Actc1 | 3.9 | 0.0004 | Actin, alpha, cardiac | Muscle development and morphology; myopathy; muscle cell death |
| NM_183408 | Pde4a | 3.7 | 0.0004 | Phosphodiesterace 4A, cAMP specific | Myopathy |
| NM_022322 | Tnmd | 3.5 | 0.0004 | Tenomodulin | Muscle morphology |
| NM_013803 | Casr | 3.5 | 0.0004 | Calcium-sensing receptor | Muscle cell death |
| NM_008596 | Sypl2 | 3.5 | 0.0004 | Synaptophysin-like 2 | Muscle contractility, development, and morphology; skeletal muscle cell size |
| NM_010518 | Igfbp5 | 3.3 | 0.0004 | Insulin-like growth factor binding protein 5 | Muscle development; skeletal muscle mass |
| NM_008876 | Pld2 | 3.2 | 0.0191 | Phospholipase D2 | Muscle cell death |
| NM_080440 | Slc8a3 | 3.2 | 0.0004 | Solute carrier family 8 (sodium/calcium exchanger), member 3 | Muscle cell death |
| NM_198190 | Ntf5 | 3.2 | 0.0004 | Neurotrophin 5 | Muscle development |
| NM_001170537 | Mef2c | 2.9 | 0.0004 | Myocyte enhancer factor 2C | Muscle contractility and development; |
| NM_176848 | Fbxo2 | 2.8 | 0.0004 | F-box protein 2 | Protein catabolism |
| NM_022027 | Syne1 | 2.7 | 0.0004 | Synaptic nuclear envelope 1 | Muscle development function, and morphology; myopathy |
| NM_009255 | Serpine2 | 2.6 | 0.0004 | Serine (or cysterine) peptidase inhibitor, clade F, member 2 | Protein catabolism |
| NM_001256224 | Wnt5a | 2.6 | 0.0011 | Wingless-related MMTV integration site 5A | Protein catabolism |
| NM_134028 | Tubg2 | 2.6 | 0.0004 | Tubulin, gamma 2 | Myopathy |

FIG. 9

| | | | | | |
|---|---|---|---|---|---|
| NM_021508 | Myox1 | 2.5 | 0.0004 | Myoxenin 1 | Muscle development and morphology, skeletal muscle mass and cell size |
| NM_110361 | Cflar | 2.5 | 0.0004 | CASP8 and FADD-like apoptosis regulator | Muscle morphology |
| NM_178608 | Reep1 | 2.3 | 0.0004 | Receptor accessory protein 1 | Myopathy |
| NM_001252455 | Ptprs | 2.3 | 0.0004 | Protein tyrosine phosphatase, receptor type, S | Muscle morphology, myopathy |
| NM_013491 | Clcn1 | 2.3 | 0.0004 | Chloride channel 1 | Muscle function |
| NM_008305 | Hspg2 | 2.3 | 0.0004 | Perlecan (heparan sulfate proteoglycan 2) | Muscle development and morphology |
| NM_025358 | Ndufa9 | 2.3 | 0.0004 | NADH dehydrogenase (ubiquinone) 1 alpha subcomplex 9 | Myopathy |
| NM_011436 | Sort1 | 2.3 | 0.0004 | Sortilin-related receptor, LDLR class A repeats-containing | Muscle function |
| NM_001243009 | Col6a3 | 2.3 | 0.0004 | Collagen, type VI, alpha 3 | Muscle development; myopathy |
| NM_025343 | Rmnd1 | 2.3 | 0.0200 | Required for meiotic nuclear division 1 homolog (S. cerevisiae) | Myopathy |
| NM_001289762 | Rarb | 2.2 | 0.0004 | Retinoic acid receptor, beta | Muscle cell death |
| NM_021355 | Fmod | 2.1 | 0.0004 | Fibromodulin | Muscle morphology |
| NM_013645 | Pvalb | 2.1 | 0.0004 | Parvalbumin | Muscle contractility and development |
| NM_172259 | Myl6b | 2.1 | 0.0004 | Myosin, light polypeptide 6B | Muscle development |
| NM_008551 | Mapkapk2 | 2.1 | 0.0004 | MAP kinase-activated protein kinase 2 | Muscle cell death |
| NM_013712 | Itgb1bp2 | 2.1 | 0.0004 | Integrin beta 1 binding protein 2 | Muscle development |
| NM_021566 | Jph2 | 2.1 | 0.0004 | Junctophilin 2 | Muscle development and morphology, myopathy |
| NM_025823 | Pcyox1 | 2.0 | 0.0004 | Prenylcysteine oxidase 1 | Protein catabolism |
| NM_001013833 | Prkg1 | 2.0 | 0.0004 | Protein kinase, cGMP-dependent, type 1 | Muscle contractility and function |
| NM_019735 | Apip | 2.0 | 0.0004 | APAF1 interacting protein | Muscle cell death |
| NM_009022 | Aldh1a2 | 2.0 | 0.0004 | Aldehyde dehydrogenase family 1, subfamily A2 | Muscle development and morphology |
| NM_008524 | Lum | 2.0 | 0.0004 | Lumican | Muscle morphology |

FIG. 9 (cont.)

*Downregulated by AR-42*

| Accession | Gene | Fold | p-value | Description | Function |
|---|---|---|---|---|---|
| NM_138677 | Edem1 | -2.0 | 0.0004 | ER degradation enhancer, mannosidase alpha-like 1 | Protein catabolism |
| NM_001163704 | Fbxo6 | -2.0 | 0.0004 | F-box protein 6 | Protein catabolism |
| NM_011724 | Xirp1 | -2.1 | 0.0004 | Xin actin-binding repeat containing 1 | Muscle, contractility, development, and morphology |
| NM_001111099 | Cdkn1a | -2.1 | 0.0004 | Cyclin-dependent kinase inhibitor 1A (P21) | Muscle development and morphology, skeletal muscle mass and cell size; muscle cell death |
| NM_001199733 | Daxx | -2.1 | 0.0004 | Fas death domain-associated protein | Muscle cell death |
| NM_001081044 | Mylk2 | -2.1 | 0.0004 | Myosin, light polypeptide kinase 2, skeletal muscle | Muscle development; myopathy |
| NM_016736 | Nub1 | -2.1 | 0.0004 | Negative regulator of ubiquitin-like proteins 1 | Protein catabolism |
| NM_007582 | Cacng1 | -2.2 | 0.0004 | Calcium channel, voltage-dependent, gamma subunit 1 | Muscle development; protein catabolism |
| NM_020033 | Ankrd2 | -2.2 | 0.0004 | Ankyrin repeat domain 2 (stretch responsive muscle) | Muscle function and morphology |
| NM_172845 | Adamts4 | -2.2 | 0.0004 | A disintegrin-like and metallopeptidase (reprolysin type) with thrombospondin type 1 motif, 4 | Muscle development; protein catabolism |
| NM_009464 | Ucp3 | -2.2 | 0.0004 | Uncoupling protein 3 | Skeletal muscle mass |
| NM_028142 | Pupla2 | -2.2 | 0.0004 | Patatin-like phospholipase domain containing 2 | Muscle morphology, muscle cell death |
| NM_104580 | Slc8a1 | -2.3 | 0.0004 | Solute carrier family 8 (sodium/calcium exchanger), member 1 | Muscle development and morphology; muscle cell death; myopathy |
| NM_008871 | Serpine1 | -2.3 | 0.0004 | Serine (or cysterine) peptidase inhibitor, clade E, member 1 | Muscle development |
| NM_001081185 | Flnc | -2.3 | 0.0004 | Filamin C, gamma (actin binding protein 280) | Muscle development and morphology; myopathy |
| NM_009238 | Sox4 | -2.3 | 0.0004 | SRY-box containing gene 4 | Muscle development and morphology |
| NM_001289716 | Bcl2l1 | -2.4 | 0.0004 | Bcl2-like 1 | Muscle cell death; myopathy |
| NM_001165894 | Akt1 | -2.4 | 0.0004 | Thymoma viral proto-oncogene 1 | Muscle atrophy, development and function; skeletal muscle |

FIG. 9 (cont.)

| | | | | | |
|---|---|---|---|---|---|
| | | | | | cell size; myopathy; protein catabolism |
| NM_007428 | Agt | -2.5 | 0.0004 | Angiotensinogen (serpin peptidase inhibitor, clade A, member 8) | Muscle atrophy; smooth muscle mass; muscle cell death; myopathy; protein catabolism |
| NM_019739 | Foxol | -2.5 | 0.0004 | Forkhead box O1 | Muscle atrophy and development; skeletal muscle mass; muscle cell death; myopathy |
| NM_013560 | Hspbl | -2.5 | 0.0004 | Heat shock protein 1 | Muscle atrophy; muscle cell death; myopathy |
| NM_026346 | Fbxo32 | -3.0 | 0.0004 | F-box protein 32 | Muscle atrophy; myopathy; protein catabolism |
| NM_001159324 | Gaa | -3.0 | 0.0004 | Glucosidase, alpha, acid | Muscle atrophy, development, function, and morphology; myopathy |
| NM_008244 | Hgs | -3.3 | 0.0004 | HGF-regulated tyrosine kinase substrate | Protein catabolism |
| NM_013468 | Ankrd1 | -3.6 | 0.0004 | Ankyrin repeat domain 1 (cardiac muscle) | Muscle development, function, and morphology, muscle cell death |
| NM_001039048 | Trim63 | -3.9 | 0.0004 | Tripartite motif-containing 63 | Muscle contractility and morphology; skeletal muscle mass and cell size; muscle atrophy; myopathy |
| NM_008491 | Lcn2 | -4.9 | 0.0004 | Lipocalin 2 | Muscle cell death |

FIG. 9 (cont.)

Supplementary Table 2. Cytokine profile analysis of serum samples from tumor-free and C-26 tumor-bearing mice treated with vehicle or AR-42 (means ± S.D.; n = 3 for each group)

| pg/ml | Tumor-free mice | | C-26 tumor-bearing mice | |
| --- | --- | --- | --- | --- |
| | Vehicle | AR-42 (n = 3) | Vehicle | AR-42 |
| Eotaxin | 677.2 ± 34.2 | 633.9 ± 84.8 | 766.8 ± 191.7 | 636.2 ± 146.0 |
| G-CSF | 145.4 ± 27.5 | 1215 ± 291 | 2520 ± 1533 | 2284 ± 989 |
| GM-CSF | 31.9 ± 18.3 | 44.7 ± 14.8 | 36.4 ± 21.1 | 41.1 ± 23.7 |
| IFNγ | 4.7 ± 2.9 | 1.2 ± 1.7 | 0.39 ± 0.76 | 0.89 ± 1.34 |
| IL-1α | 293.0 ± 184.7 | 169.5 ± 130.2 | 78.7 ± 50.7 | 25.1 ± 15.7 |
| IL-1β | 11.1 ± 17.0 | 4.7 ± 2.7 | 2.9 ± 2.3 | 2.2 ± 1.8 |
| IL-2 | 3.6 ± 1.1 | 4.0 ± 1.6 | 3.8 ± 1.7 | 1.7 ± 1.3 |
| IL-3 | 3.0 ± 1.9 | 1.2 ± 1.4 | 0.5 ± 0.7 | 1.7 ± 2.6 |
| IL-4 | 0.02 ± 0.05 | 0 | 0 | 0.5 ± 0.9 |
| IL5 | 3.4 ± 0.6 | 4.3 ± 1.1 | 0.76 ± 1.09 | 25.2 ± 40.6 |
| IL-6 | 3.0 ± 1.3 | 5.1 ± 3.6 | 216.6 ± 108.8 | 100.6 ± 43.1 |
| IL-7 | 8.8 ± 2.5 | 13.0 ± 10.2 | 10.9 ± 5.2 | 5.8 ± 2.2 |
| IL-9 | 38.8 ± 8.7 | 34.0 ± 13.0 | 54.4 ± 42.0 | 11.4 ± 21.2 |
| IL-10 | 5.6 ± 2.0 | 6.8 ± 1.0 | 8.2 ± 3.6 | 14.9 ± 9.8 |
| IL12 (p40) | 57.7 ± 33.1 | 42.8 ± 44.6 | 7.3 ± 1.8 | 7.4 ± 2.8 |
| IL-12 (p70) | 4.6 ± 1.5 | 5.0 ± 1.9 | 3.8 ± 2.2 | 15.3 ± 32.0 |
| IL-13 | 109.9 ± 20.7 | 63.0 ± 27.6 | 88.0 ± 24.8 | 68.3 ± 26.8 |
| EL-15 | 36.2 ± 13.0 | 70.7 ± 88.1 | 94.1 ± 161.3 | 18.6 ± 8.7 |
| IL-17 | 5.1 ± 1.1 | 6.838 ± 3.010 | 3.293 ± 2.925 | 3.277 ± 2.774 |
| IP-10 | 166.2 ± 53.3 | 135.6 ± 42.4 | 180.5 ± 59.9 | 311.5 ± 140.4 |
| K.C | 89.7 ± 38.2 | 156.4 ± 62.1 | 115.1 ± 43.9 | 1070 ± 1072 |
| LIF | 1.7 ± 2.7 | 5.1 ± 10.247 | 20.8 ± 13.1 | 4.7 ± 3.0 |
| LIX | 6778 ± 2835 | 5625 ± 2760 | 4917 ± 3165 | 1197 ± 1376 |
| MCP-1 | 41.8 ± 12.1 | 24.8 ± 5.9 | 35.5 ± 27.3 | 63.1 ± 17.8 |
| M-CSF | 9.5 ± 4.3 | 5.9 ± 1.7 | 4.2 ± 2.3 | 6.6 ± 2.4 |
| MIG | 136.5 ± 94.3 | 66.0 ± 35.1 | 30.2 ± 18.0 | 77.4 ± 33.0 |
| MIP-1α | 51.3 ± 17.7 | 42.2 ± 25.0 | 40.2 ± 24.1 | 22.9 ± 19.3 |
| MIP-1β | 103.7 ± 8.8 | 89.7 ± 14.7 | 63.6 ± 17.9 | 70.2 ± 8.8 |
| MIP-2 | 81.1 ± 20.9 | 68.1 ± 20.4 | 57.4 ± 21.9 | 49.8 ± 4.0 |
| RANTES | 27.9 ± 4.5 | 21.8 ± 7.3 | 21.2 ± 7.5 | 20.2 ± 5.5 |
| TNFα | 5.5 ± 3.5 | 0.23 ± 0.52 | 2.8 ± 3.7 | 3.2 ± 3.5 |
| VEGF | 1.7 ± 0.36 | 1.5 ± 0.6 | 1.4 ± 0.5 | 1.1 ± 0.3 |

FIG. 10

Supplementary Table 3. RNA-seq analysis of differentially expressed genes (> 4-fold) in muscles from AR-42-treated versus vehicle-treated C-26 tumor-bearing mice (n = 3)

| RefSeq ID (UCSC) | Gene ID | log2 fold change | P value | Description |
|---|---|---|---|---|
| *Upregulated by AR-42* | | | | |
| NM_009700 | Aqp4 | 6.7 | 0.0004 | Aquaporin 4 |
| NM_009867 | Cdh4 | 6.2 | 0.0004 | Cadherin 4 |
| NR_002870 | Dnm3os | 6.1 | 0.0004 | Dynamin 3, opposite strand |
| NM_207281.3 | 4832428D23Rik | 6.0 | 0.0004 | RIKEN cDNA 4832428D23 gene |
| NM_001081116 | Arhgef17 | 5.8 | 0.0083 | Rho guanine nucleotide exchange factor (GEF) 17 |
| NM_008438 | Kera | 5.8 | 0.0004 | Keratocan |
| NM_008393 | Irx3 | 5.6 | 0.0004 | Iroquois related homeobox 3 (Drosophila) |
| NM_008473 | Krt1 | 5.5 | 0.0004 | Keratin 1 |
| NM_001198886 | Dpp6 | 5.4 | 0.0004 | Dipeptidylpeptidase 6 |
| NM_016749 | Mybph | 5.1 | 0.0004 | Myosin binding protein H |
| NM_001162983 | Lrrc38 | 5.0 | 0.0004 | Leucine rich repeat containing 38 |
| NM_001109988.1 | D0H4S114 | 4.9 | 0.0004 | DNA segment, human D4S114 |
| NM_001101475 | F830016B08Rik | 4.9 | 0.0382 | RIKEN cDNA F830016B08 gene |
| NR_045431 | 4933401D09Rik | 4.9 | 0.0004 | RIKEN cDNA 4933401D09 gene |
| NM_001205219 | Sorbs2 | 4.9 | 0.0436 | Sorbin and SH3 domain containing 2 |
| NM_010254 | Galr2 | 4.9 | 0.0004 | Galanin receptor 2 |
| NM_011825 | Grem2 | 4.9 | 0.0004 | Gremlin 2 homolog, cysteine knot superfamily (Xenopus laevis) |
| NM_001081456 | Plcd4 | 4.8 | 0.0004 | Phospholipase C, delta 4 |
| NM_181664 | Crip3 | 4.7 | 0.0004 | Cysteine-rich protein 3 |
| NM_027948 | 1700003E16Rik | 4.7 | 0.0004 | RIKEN cDNA 1700003E16 gene |
| NM_028639 | Ttc7 | 4.7 | 0.0317 | Tetratricopeptide repeat domain 7 |
| NR_045491 | 2310016D03Rik | 4.7 | 0.0004 | RIKEN cDNA 2310016D03 gene |
| NM_025734 | Kcng4 | 4.6 | 0.0004 | Potassium voltage-gated channel, subfamily G, member 4 |
| NM_025290 | Rsph1 | 4.6 | 0.0004 | Radial spoke head 1 homolog (Chlamydomonas) |
| NM_011506 | Sucla2 | 4.5 | 0.0014 | Succinate-Coenzyme A ligase, ADP-forming beta subunit |
| NM_001101475 | F830016B08Rik | 4.5 | 0.0021 | RIKEN cDNA F830016B08 gene |
| NM_001081052 | Nhs | 4.5 | 0.0004 | Nance-Horan syndrome (human) |
| NM_001008533 | Adora1 | 4.4 | 0.0004 | Adenosine A1 receptor |
| NM_029932 | Spns3 | 4.4 | 0.0004 | Spinster homolog 3 (Drosophila) |
| NM_001013013 | Dhrs7c | 4.4 | 0.0008 | Dehydrogenase/reductase (SDR family) member 7C |
| NM_024291 | Ky | 4.3 | 0.0004 | Kyphoscoliosis peptidase |
| NM_010742 | Ly6d | 4.2 | 0.0085 | Lymphocyte antigen 6 complex, locus D |
| NM_010267 | Gdap1 | 4.2 | 0.0004 | Ganglioside-induced differentiation-associated-protein 1 |
| NM_013569 | Kcnh2 | 4.1 | 0.0004 | Potassium voltage-gated channel, subfamily 1 (eag related), member 2 |
| NM_176916 | Pld5 | 4.1 | 0.0004 | Phospholipase D family, member 5 |

FIG. 11

| | | | | |
|---|---|---|---|---|
| NM_001164223 | Rpa1 | 4.1 | 0.0102 | Replication protein A1 |
| NM_008508 | Lor | 4.1 | 0.0004 | Loricrin |
| NM_001114116 | Syt3 | 4.0 | 0.0004 | Synaptotagmin III |
| NM_013530 | Gnb3 | 4.0 | 0.0004 | Guanine nucleotide binding protein, beta 3 |
| NM_020036 | Calm4 | 3.9 | 0.0004 | Calmodulin 4 |
| NM_145128 | Mgat5 | 3.9 | 0.0319 | Mannoside acetylglucosaminyltransferase 5 |
| NM_008974 | Ptp4a2 | 3.9 | 0.0004 | Protein tyrosine phosphatase 4a2 |
| NM_148941 | E3ovl4 | 3.9 | 0.0004 | Elongation of very long chain fatty acids (FEN1/Elo2, SUR4/Elo3, yeast)-like 4 |
| NM_030133 | Srbd1 | 3.9 | 0.0011 | S1 RNA binding domain 1 |
| NM_009608 | Actc1 | 3.9 | 0.0004 | Actin, alpha, cardiac |
| NM_198166.3 | Uts2d | 3.9 | 0.0004 | Urotensin 2 domain containing |
| NM_001003667 | Krt77 | 3.8 | 0.0004 | Keratin 77 |
| NM_001291129 | Nnat | 3.8 | 0.0480 | Neuronatin |
| NM_025771 | Cntnap2 | 3.8 | 0.0004 | Contactin associated protein-like 2 |
| NM_001136084 | Tph1 | 3.8 | 0.0004 | Tryptophan hydroxylase 1 |
| NM_026278 | Lrp2bp | 3.8 | 0.0004 | Lrp2 binding protein |
| NM_001081052 | Nhs | 3.8 | 0.0004 | Nance-Horan syndrome (human) |
| NM_001205219 | Sorbs2 | 3.7 | 0.0242 | Sorbin and SH3 domain containing 2 |
| NM_001199224 | Agbl1 | 3.7 | 0.0004 | ATP/GTP binding protein-like 1 |
| NM_027011 | Krt5 | 3.7 | 0.0004 | Keratin 5 |
| NM_183408 | Pde4a | 3.7 | 0.0004 | Phosphodiesterase 4A, cAMP specific |
| NM_175486 | 6430571L13Rik | 3.7 | 0.0004 | RIKEN cDNA 6430571L13 gene |
| NM_021359 | Itgb6 | 3.7 | 0.0004 | Integrin beta 6 |
| NM_016958 | Krt14 | 3.6 | 0.0004 | Keratin 14 |
| NM_001013826 | Dupd1 | 3.6 | 0.0004 | Dual specificity phosphatase and pro isomerase domain containing 1 |
| NM_001244200 | Pax6 | 3.6 | 0.0014 | Paired box gene 6 |
| NM_198112 | Ostn | 3.6 | 0.0004 | Osteocrin |
| NM_182993 | Slc17a7 | 3.6 | 0.0004 | Solute carrier family 17 (sodium-dependent inorganic phosphate cotransporter), member 7 |
| NM_001146275 | Iigp1 | 3.6 | 0.0004 | Interferon inducible GTPase 1 |
| NM_007975 | F2rl3 | 3.6 | 0.0078 | Coagulation factor II (thrombin) receptor-like 3 |
| NM_023695 | Crybb1 | 3.5 | 0.0004 | Crystallin, beta B1 |
| NM_010067 | Trdmt1 | 3.5 | 0.0492 | TRNA aspartic acid methyltransferase 1 |
| NM_022322 | Tnmd | 3.5 | 0.0004 | Tenomodulin |
| NM_016667 | Sntb1 | 3.5 | 0.0004 | Syntrophin, basic 1 |
| NM_013803 | Casr | 3.5 | 0.0004 | Calcium-sensing receptor |
| NM_008596 | Sypl2 | 3.5 | 0.0004 | Synaptophysin-like 2 |
| NM_027258 | Rnf157 | 3.5 | 0.0308 | Ring finger protein 157 |
| NM_021443 | Ccl8 | 3.4 | 0.0004 | Chemokine (C-C motif) ligand 8 |
| NM_011356 | Frzb | 3.4 | 0.0004 | Frizzled-related protein |
| NM_009813 | Casq1 | 3.4 | 0.0004 | Calsequestrin 1 |
| NR_015523 | A730017L22Rik | 3.4 | 0.0017 | RIKEN cDNA A730017L22 gene |
| NM_010518 | Igfbp5 | 3.3 | 0.0004 | Insulin-like growth factor binding protein 5 |
| NM_198300 | Cpeb3 | 3.3 | 0.0029 | Cytoplasmic polyadenylation element binding protein 3 |
| NM_001081160 | Mdga1 | 3.3 | 0.0004 | MAM domain containing glycosyl-phosphatidylinositol anchor 1 |
| NM_020509 | Retnla | 3.3 | 0.0004 | Resistin like alpha |

FIG. 11 (cont.)

| | | | | |
|---|---|---|---|---|
| NM_175541 | Mum1l1 | 2.8 | 0.0004 | Melanoma associated antigen (mutated) 1-like 1 |
| NM_175486 | 6430571L13Rik | 2.8 | 0.0080 | RIKEN cDNA 6430571L13 gene |
| NM_001025577 | Maf | 2.8 | 0.0004 | Avian musculoaponeurotic fibrosarcoma (v-maf) AS42 oncogene homolog |
| NM_133226 | Pdzd3 | 2.8 | 0.0004 | PDZ domain containing 3 |
| NM_008469 | Krt15 | 2.8 | 0.0004 | Keratin 15 |
| NM_029037.4 | 4930444A02Rik | 2.8 | 0.0004 | RIKEN cDNA 4930444A02 gene |
| NM_029297 | Dynlrb2 | 2.8 | 0.0112 | Dynein light chain roadblock-type 2 |
| n/a | Ercc2,Mir343 | 2.8 | 0.0004 | Excision repair cross-complementing rodent repair deficiency, complementation group 2 |
| NM_176848 | Fbxo2 | 2.8 | 0.0004 | F-box protein 2 |
| NM_007670 | Cdkn2b | 2.8 | 0.0004 | Cyclin-dependent kinase inhibitor 2B (p15, inhibits CDK4) |
| NM_001081416 | Fndc1 | 2.7 | 0.0336 | Fibronectin type III domain containing 1 |
| NM_172794 | Zfp454 | 2.7 | 0.0004 | Zinc finger protein 454 |
| NM_026794 | Deb1 | 2.7 | 0.0004 | Differentially expressed in B16F10 1 |
| NM_177784 | Klhl23 | 1.7 | 0.0004 | Kelch-like 23 (Drosophila) |
| NM_022027 | Syne1 | 2.7 | 0.0004 | Synaptic nuclear envelope 1 |
| NM_028798 | Crct1 | 2.7 | 0.0208 | Cysteine-rich C-terminal 1 |
| NM_001009951.1 | BC088983 | 2.7 | 0.0214 | cDNA sequence BC088983 |
| NM_001289450 | Kcnab1 | 2.7 | 0.0004 | Potassium voltage-gated channel shaker-related subfamily, beta member 1 |
| NM_001290825 | Col17a1 | 2.7 | 0.0004 | Collagen type XVII, alpha 1 |
| NM_016685 | Comp | 2.7 | 0.0004 | Cartilage oligomeric matrix protein |
| NM_177222 | Casc1 | 2.7 | 0.0166 | Cancer susceptibility candidate 1 |
| NM_001290679 | Tmem14a | 2.7 | 0.0004 | Transmembrane protein 14A |
| NM_198111 | Akap6 | 2.7 | 0.0004 | A kinase (PRKA) anchor protein 6 |
| NM_020278 | Lgi1 | 2.7 | 0.0004 | Leucine-rich repeat LGI family, member 1 |
| NM_008496 | Lgals7 | 2.7 | 0.0004 | Lectin, galactose binding, soluble 7 |
| NM_025500 | Mrpl37 | 2.6 | 0.0004 | Mitochondrial ribosomal protein L37 |
| NM_001290708 | Smarca1 | 2.6 | 0.0004 | SWI/SNF related, matrix associated, actin dependent regulator of chromatin subfamily a, member 1 |
| NM_053166 | Trim7 | 2.6 | 0.0004 | Tripartite motif protein 7 |
| NM_139152 | Asb18 | 2.6 | 0.0004 | Ankyrin repeat and SOCS box-containing 18 |
| NM_009255 | Serpine2 | 2.6 | 0.0004 | Serine (or cysteine) peptidase inhibitor, clade E, member 2 |
| NM_207205 | Igsf3 | 2.6 | 0.0004 | Immunoglobulin superfamily, member 3 |
| NM_023734 | Pi16 | 2.6 | 0.0206 | Peptidase inhibitor 16 |
| NR_045837 | 9130227L01Rik | 2.6 | 0.0083 | RIKEN cDNA 9130227L01 gene |
| NM_011638 | Tfrc | 2.6 | 0.0004 | Transferrin receptor |
| NM_001256224 | Wnt5a | 2.6 | 0.0011 | Wingless-related MMTV integration site 5A |
| NM_181541 | Caprin2 | 2.6 | 0.0004 | Caprin family member 2 |
| NM_001077202 | Hs6st2 | 2.6 | 0.0004 | Heparan sulfate 6-O-sulfotransferase 2 |
| NM_010271 | Gpd1 | 2.6 | 0.0004 | Glycerol-3-phosphate dehydrogenase 1 (soluble) |
| NM_017392 | Celsr2 | 2.6 | 0.0004 | Cadherin EGF LAG seven-pass G-type receptor 2 |
| NM_010576 | Itga4 | 2.6 | 0.0004 | Integrin alpha 4 |

FIG. 11 (cont.)

| | | | | |
|---|---|---|---|---|
| NM_011994 | Abcd2 | 2.6 | 0.0004 | ATP-binding cassette, sub-family D(ALD), member 2 |
| n/a | Fabp9 | 2.6 | 0.0004 | Fatty acid binding protein 9, testis |
| NM_001030305.2 | Pmp2 | 2.6 | 0.0004 | Peripheral myelin protein 2 |
| NM_001289498 | Egflam | 2.6 | 0.0004 | Tubulin, gamma 2 |
| NM_134028 | Tubg2 | 2.6 | 0.0004 | EGF-like, fibronectin type III and laminin G domains |
| n/a | Snora31 | 2.6 | 0.0035 | Tumor protein, translationally controlled 1 |
| n/a | Tpt1 | 2.6 | 0.0035 | Tumor protein, translationally controlled 1 |
| NM_001198765 | Postn | 2.6 | 0.0004 | Periostin, osteoblast specific factor |
| NM_025998 | Nkain1 | 2.5 | 0.0004 | Na+/K+ transporting ATPase interacting 1 |
| NM_007988 | Fasn | 2.5 | 0.0004 | Fatty acid synthase |
| NM_016788 | Tnk2 | 2.5 | 0.0004 | Tyrosine kinase, non-receptor, 2 |
| NM_029761 | Dok5 | 2.5 | 0.0004 | Docking protein 5 |
| NM_133729 | 2610018G03Rik | 2.5 | 0.0004 | RIKEN cDNA 2610018G03 gene |
| NM_001145887 | Tiam1 | 2.5 | 0.0004 | T-cell lymphoma invasion and metastasis 1 |
| NM_025420 | Lce1m | 2.5 | 0.0008 | Late cornified envelope 1M |
| NM_145134 | Spsb4 | 2.5 | 0.0004 | SplA/ryanodine receptor domain and SOCS box containing 4 |
| NR_040577 | 1700123M08Rik | 2.5 | 0.0004 | RIKEN cDNA 1700123M08 gene |
| NM_023047 | Dpysl5 | 2.5 | 0.0004 | Dihydropyrimidinase-like 5 |
| NM_139152 | Asb18 | 2.5 | 0.0004 | Ankyrin repeat and SOCS box-containing 18 |
| NM_008409 | Itm2a | 2.5 | 0.0004 | Integral membrane protein 2A |
| NM_021508 | Myoz1 | 2.5 | 0.0004 | Myozenin 1 |
| NM_029568 | Mfap4 | 2.5 | 0.0004 | Microfibrillar-associated protein 4 |
| NM_026626 | Efcab2 | 2.5 | 0.0011 | EF-hand calcium binding domain 2 |
| NM_172784 | Lrp11 | 2.5 | 0.0004 | CASP8 and FADD-like apoptosis regulator |
| NR_110361 | Cflar | 2.5 | 0.0004 | Low density lipoprotein receptor-related protein 11 |
| NM_001291104 | Fgf11 | 2.5 | 0.0004 | Fibroblast growth factor 11 |
| NM_027756 | Mfap3l | 2.5 | 0.0004 | Microfibrillar-associated protein 3-like |
| NM_001111145 | Gm514 | 2.5 | 0.0004 | Gene model 514, (NCBI) |
| NM_009469 | Ulk1 | 2.5 | 0.0212 | Unc-51 like kinase 1 (C.elegans) |
| NM_026956 | Cd209f | 2.5 | 0.0004 | CD209f antigen |
| NM_019718 | Arl3 | 2.5 | 0.0004 | ADP-ribosylation factor-like 3 |
| NM_026617 | Tmbim4 | 2.4 | 0.0092 | Dopa decarboxylase |
| NM_016672 | Ddc | 2.4 | 0.0004 | Transmembrane BAX inhibitor motif containing 4 |
| NM_172899 | Dmkn | 2.4 | 0.0004 | Dermokine |
| NM_019563 | Cited4 | 2.4 | 0.0004 | Glu/Asp-rich carboxy-terminal domain, 4 |
| NM_013803 | Casr | 2.4 | 0.0119 | Cbp/p300-interacting transactivator, with Calcium-sensing receptor |
| NM_194350 | Mafa | 2.4 | 0.0004 | V-maf musculoaponeurotic fibrosarcoma oncogene family, protein A (avian) |
| NM_013933 | Vapa | 2.4 | 0.0004 | Vesicle-associated membrane protein, associated protein A |
| NM_025384 | Dnajc15 | 2.4 | 0.0287 | DnaJ (hsp40) homolog, subfamily C, member 15 |
| NM_009873 | Cdk6 | 2.4 | 0.0004 | Cyclin-dependent kinase 6 |
| NR_030764 | 2700097O09Rik | 2.4 | 0.0021 | RIKEN cDNA 2700097O09 gene |

FIG. 11 (cont.)

| | | | | |
|---|---|---|---|---|
| NM_153546 | Mboat1 | 2.2 | 0.0004 | Membrane bound O-acyltransferase domain containing 1 |
| NM_001289762 | Rarb | 2.2 | 0.0004 | Retinoic acid receptor, beta |
| NM_134079 | Adk | 2.2 | 0.0026 | Adenosine kinase |
| NM_010357 | Gsta4 | 2.2 | 0.0004 | Glutathione S-transferase, alpha 4 |
| NM_177073 | Relt | 2.2 | 0.0004 | RELT tumor necrosis factor receptor |
| NM_001033131 | Krtdap | 2.2 | 0.0011 | Keratinocyte differentiation associated protein |
| NM_175645 | Xylt1 | 2.2 | 0.0004 | Xylosyltransferase 1 |
| NM_007742 | Col1a1 | 2.2 | 0.0004 | Collagen, type 1, alpha 1 |
| NR_040577 | 1700123M08Rik | 2.2 | 0.0004 | RIKEN cDNA 1700123M08 gene |
| NM_016785 | Tpmt | 2.2 | 0.0004 | Thiopurine methyltransferase |
| NM_001013771 | Gm973 | 2.2 | 0.0008 | Gene model 973, (NCBI) |
| NM_021717 | Nrip2 | 2.2 | 0.0210 | Nuclear receptor interaction protein 2 |
| NM_001012450 | Ankrd6 | 2.2 | 0.0004 | Ankyrin repeat domain 6 |
| NM_172600 | 6720456H20Rik | 2.2 | 0.0057 | RIKEN cDNA 6720456H20 gene |
| NM_145523 | Gca | 2.2 | 0.0218 | Grancalcin |
| NM_017378 | Pcdh12 | 2.2 | 0.0004 | Protocadherin 12 |
| NM_153801 | Tecr1 | 2.2 | 0.0260 | n/a |
| NM_027865 | Tmem25 | 2.2 | 0.0004 | Transmembrane protein 25 |
| NM_177698 | Psd3 | 2.2 | 0.0218 | Pleckstrin and Sec7 domain containing 3 |
| NM_010924 | Nnmt | 2.2 | 0.0004 | Nicotinamide N-methyltransferase |
| NM_078479 | Mrps21 | 2.2 | 0.0112 | Mitochondrial ribosomal protein S21 |
| NM_001285849 | Paqr7 | 2.2 | 0.0004 | Progestin and adipoQ receptor family member VII |
| NM_028132 | Pgm2 | 2.1 | 0.0004 | Phosphoglucomutase 2 |
| NM_172527 | Nudt15 | 2.1 | 0.0004 | Nudix (nucleoside diphosphate linked moiety X)-type motif 15 |
| NM_026732 | Mrpl14 | 2.1 | 0.0248 | Mitochondrial ribosomal protein L14 |
| NM_194060 | Foxo6 | 2.1 | 0.0004 | Forkhead box O6 |
| NR_024619 | 2610001J05Rik | 2.1 | 0.0216 | RIKEN cDNA 2610001J05 gene |
| NM_021355 | Fmod | 2.1 | 0.0004 | Fibromodulin |
| NM_011775 | Zp2 | 2.1 | 0.0004 | Zona pellucida glycoprotein 2 |
| NM_146188 | Kctd15 | 2.1 | 0.0008 | Potassium channel tetramerisation domain containing 15 |
| NM_008571 | Mcpt2 | 2.1 | 0.0004 | Mast cell protease 2 |
| NM_013645 | Pvalb | 2.1 | 0.0004 | Parvalbumin |
| NM_001076681 | 1810012P15Rik | 2.1 | 0.0070 | RIKEN cDNA 1810012P15 gene |
| NM_172259 | Myl6b | 2.1 | 0.0004 | Myosin, light polypeptide 6B |
| NR_040577 | 1700123M08Rik | 2.1 | 0.0470 | RIKEN cDNA 1700123M08 gene |
| NM_012048 | Polk | 2.1 | 0.0004 | Polymerase (DNA directed), kappa |
| NM_001168476 | Ttc23 | 2.1 | 0.0004 | Tetratricopeptide repeat domain 23 |
| NM_172522 | Megf11 | 2.1 | 0.0004 | Multiple EGF-like-domains 11 |
| NM_017382 | Rab11a | 2.1 | 0.0004 | RAB11a, member RAS oncogene family |
| NM_008609 | Mmp15 | 2.1 | 0.0004 | Matrix metallopeptidase 15 |
| NM_054088 | Pnpla3 | 2.1 | 0.0004 | Patatin-like phospholipase domain containing 3 |
| NM_007590 | Calm3 | 2.1 | 0.0004 | Calmodulin 3 |
| NM_001168471 | Dynll2 | 2.1 | 0.0355 | Dynein light chain LC8-type 2 |
| NM_080856 | Asb14 | 2.1 | 0.0004 | Ankyrin repeat and SOCS box-containing protein 14 |
| NM_198414 | Paqr9 | 2.1 | 0.0004 | Progestin and adipoQ receptor family member IX |

FIG. 11 (cont.)

| Accession | Gene | FC | p-value | Description |
|---|---|---|---|---|
| NM_017394 | Slc7a10 | 2.1 | 0.0321 | Solute carrier family 7 (cationic amino acid transporter, y+ system), member 10 |
| NM_001271758 | Wnt5b | 2.1 | 0.0393 | Wingless-related MMTV integration site 5B |
| NM_011035 | Pak1 | 2.1 | 0.0004 | P21 (CDKN1A)-activated kinase 1 |
| NM_058212 | Dpf3 | 2.1 | 0.0014 | D4, zinc and double PHD fingers family 3 |
| NM_008832 | Phka1 | 2.1 | 0.0004 | Phosphorylase kinase alpha 1 |
| NM_008551 | Mapkapk2 | 2.1 | 0.0004 | MAP kinase-activated protein kinase 2 |
| NM_013712 | Itgb1bp2 | 2.1 | 0.0004 | Integrin beta 1 binding protein 2 |
| NM_016673 | Cntfr | 2.1 | 0.0004 | Ciliary neurotrophic factor receptor |
| NM_021566 | Jph2 | 2.1 | 0.0004 | Junctophilin 2 |
| NM_013415 | Atp1b2 | 2.1 | 0.0004 | ATPase, Na+/K+ transporting, beta 2 polypeptide |
| NM_133687 | Cxxc5 | 2.1 | 0.0004 | CXXC finger 5 |
| NM_011932 | Dapp1 | 2.0 | 0.0004 | Dual adaptor for phosphotyrosine and 3-phosphoinositides 1 |
| NM_153554 | Aldh1a2 | 2.0 | 0.0004 | Aldehyde dehydrogenase 18 family, member A1 |
| NM_001290761 | Nmral1 | 2.0 | 0.0004 | NmrA-like family domain containing 1 |
| NM_146030 | Plekhh3 | 2.0 | 0.0004 | Pleckstrin homology domain containing, family H (with MyTH4 domain) member 3 |
| NM_025823 | Pcyox1 | 2.0 | 0.0004 | Prenylcysteine oxidase 1 |
| NM_176920 | Lrtm1 | 2.0 | 0.0004 | Leucine-rich repeats and transmembrane domains 1 |
| NM_001013833 | Prkg1 | 2.0 | 0.0004 | Protein kinase, cGMP-dependent, type 1 |
| NM_019735 | Apip | 2.0 | 0.0004 | APAF1 interacting protein |
| NM_011734 | Siae | 2.0 | 0.0004 | Sialic acid acetylesterase |
| NM_009022 | Aldh1a2 | 2.0 | 0.0004 | Aldehyde dehydrogenase family 1, subfamily A2 |
| NM_008524 | Lum | 2.0 | 0.0004 | Lumican |
| NM_001198790 | Ak1 | 2.0 | 0.0216 | Adenylate kinase 1 |
| NM_178401 | Ramp1 | 2.0 | 0.0004 | Receptor (calcitonin) activity modifying protein 1 |
| NM_172752 | Sorbs2 | 2.0 | 0.0004 | Sorbin and SH3 domain containing 2 |
| NM_013737 | Pla2g7 | 2.0 | 0.0004 | Phospholipase A2, group VII (platelet-activating factor acetylhydrolase, plasma) |
| NR_027236 | AI854703 | 2.0 | 0.0004 | Expressed sequence AI854703 |
| NM_145602 | Ndrg4 | 2.0 | 0.0004 | N-myc downstream regulated gene 4 |
| NM_011759 | Zfp41 | 2.0 | 0.0004 | Zinc finger protein 41 |
| NM_007506 | Atp5gl | 2.0 | 0.0004 | ATP synthase, H+ transporting, mitochondrial F0 complex, subunit c (subunit 9), isoform 1 |
| NM_019573 | Wwox | 2.0 | 0.0004 | WW domain-containing oxidoreductase |
| NM_009073 | Rom1 | 2.0 | 0.0004 | Rod outer segment membrane protein 1 |
| NM_027289 | Nt5dc2 | 2.0 | 0.0130 | 5'-nucleotidase domain containing 2 |
| Downregulated by AR-42 | | | | |
| NM_025994 | Efhd2 | -2.0 | 0.0004 | Ef hand domain containing 2 |
| NM_016868 | Hif3a | -2.0 | 0.0004 | Hypoxia inducible factor 3, alpha subunit |

FIG. 11 (cont.)

| | | | | |
|---|---|---|---|---|
| NM_029936 | Ddx10 | 2.4 | 0.0008 | DEAD (Asp-Glu-Ala-Asp) box polypeptide 10 |
| NM_133769 | Cyfip2 | 2.4 | 0.0004 | Cytoplasmic FMR1 interacting protein 2 |
| NM_153546 | Mboat1 | 2.4 | 0.0004 | Membrane bound O-acyltransferase domain containing 1 |
| NM_173431 | Rpgrip1l | 2.4 | 0.0032 | Rpgrip1-like |
| NM_138953 | Ell2 | 2.4 | 0.0107 | Elongation factor RNA polymerase II 2 |
| NM_010264 | Nr6a1 | 2.4 | 0.0420 | Nuclear receptor subfamily 6, group A, member 1 |
| NM_001127725 | Sec14l5 | 2.4 | 0.0004 | SEC14-like 5 (S. cerevisiae) |
| NM_182930 | Plekha6 | 2.4 | 0.0004 | Pleckstrin homology domain containing family A member 6 |
| NM_011331 | Ccl12 | 2.4 | 0.0116 | Chemokine (C-C motif) ligand 12 |
| NM_207278 | Tigd4 | 2.4 | 0.0004 | Tigger transposable element derived 4 |
| NM_177039 | A530016L24Rik | 2.4 | 0.0004 | RIKEN cDNA A530016L24 gene |
| NM_178929 | Kazald1 | 2.3 | 0.0004 | Kazal-type serine peptidase inhibitor domain 1 |
| NM_178608 | Reep1 | 2.3 | 0.0004 | Receptor accessory protein 1 |
| NM_001252455 | Ptprs | 2.3 | 0.0004 | Protein tyrosine phosphatase, receptor type, S |
| NM_028639 | Ttc7 | 2.3 | 0.0004 | Tetratricopeptide repeat domain 7 |
| NM_013491 | Clcn1 | 2.3 | 0.0004 | Chloride channel 1 |
| NM_025474 | Mrps14 | 2.3 | 0.0004 | Mitochondrial ribosomal protein S14 |
| NM_008305 | Hspg2 | 2.3 | 0.0004 | Perlecan (heparan sulfate proteoglycan 2) |
| NM_009533 | Xrcc5 | 2.3 | 0.0353 | X-ray repair complementing defective repair in Chinese hamster cells 5 |
| NM_019573 | Wwox | 2.3 | 0.0314 | WW domain-containing oxidoreductase |
| NM_025358 | Ndufa9 | 2.3 | 0.0004 | NADH dehydrogenase (ubiquinone) 1 alpha subcomplex, 9 |
| NM_011923 | Angptl2 | 2.3 | 0.0004 | Angiopoietin-like 2 |
| NM_026728 | Echdc2 | 2.3 | 0.0004 | Enoyl Coenzyme A hydratase domain containing 2 |
| NM_177471 | Ccdc69 | 2.3 | 0.0004 | Coiled-coil domain containing 69 |
| NM_001291282 | Tm6sf1 | 2.3 | 0.0004 | Transmembrane 6 superfamily member 1 |
| NM_009396 | Tnfaip2 | 2.3 | 0.0004 | Tumor necrosis factor, alpha-induced protein 2 |
| NM_001007578 | Armcx6 | 2.3 | 0.0004 | Armadillo repeat containing, X-linked 6 |
| NM_133804 | Tmem132a | 2.3 | 0.0004 | Transmembrane protein 132A |
| NM_011436 | Sorl1 | 2.3 | 0.0004 | Sortilin-related receptor, LDLR class A repeats-containing |
| NM_001164225 | Fbxl16 | 2.3 | 0.0004 | F-box and leucine-rich repeat protein 16 |
| NM_001007583 | Best3 | 2.3 | 0.0004 | Bestrophin 3 |
| NM_133903 | Spon2 | 2.3 | 0.0004 | Spondin 2, extracellular matrix protein |
| NM_001243009 | Col6a3 | 2.3 | 0.0004 | Collagen, type VI, alpha 3 |
| NM_025343 | Rmnd1 | 2.3 | 0.0200 | Required for meiotic nuclear division 1 homolog (S. cerevisiae) |
| NM_010272 | Gdf11 | 2.3 | 0.0004 | Growth differentiation factor 11 |
| NM_026219 | Uqcrb | 2.3 | 0.0008 | Ubiquinol-cytochrome c reductase binding protein |
| NM_001039562 | Ankrd37 | 2.2 | 0.0004 | Ankyrin repeat domain 37 |
| NM_146188 | Kctd15 | 2.2 | 0.0004 | Potassium channel tetramerisation domain containing 15 |

FIG. 11 (cont.)

| | | | | |
|---|---|---|---|---|
| NM_012065 | Pde6g | -2.0 | 0.0004 | Phosphodiesterase 6G, cGMP-specific, rod, gamma |
| NM_023476 | Tinag11 | -2.0 | 0.0488 | n/a |
| NM_001042655 | Tbc1d17 | -2.0 | 0.0004 | TBC1 domain family, member 17 |
| NM_007695 | Chi3l1 | -2.0 | 0.0004 | Chitinase 3-like 1 |
| NM_026877 | Aspscr1 | -2.0 | 0.0004 | Alveolar soft part sarcoma chromosome region, candidate 1 (human) |
| NM_138677 | Edem1 | -2.0 | 0.0004 | ER degradation enhancer, mannosidase alpha-like 1 |
| NM_026220 | Mfap1a | -2.0 | 0.0004 | Microfibrillar-associated protein 1A |
| NM_001033411 | Gm826 | -2.0 | 0.0004 | Gene model 826, (NCBI) |
| NM_153075 | Catsper2 | -2.0 | 0.0004 | Cation channel sperm associated 2 |
| NM_001163704 | Fbxo6 | -2.0 | 0.0004 | F-box protein 6 |
| NM_001162465 | Dtnb | -2.0 | 0.0004 | Dystrobrevin, beta |
| NM_011690 | Vars | -2.0 | 0.0004 | Valyl-tRNA synthetase |
| NM_001081349 | Slc43a1 | -2.0 | 0.0004 | Solute carrier family 43 member 1 |
| NM_133765 | Fbxo31 | -2.1 | 0.0004 | F-box protein 31 |
| NM_029008 | 4833403I15Rik | -2.1 | 0.0004 | RIKEN cDNA 4833403I15 gene |
| NM_001286498 | Tex264 | -2.1 | 0.0004 | Testis expressed gene 264 |
| NM_001289917 | Rora | -2.1 | 0.0004 | RAR-related orphan receptor alpha |
| NM_010220 | Fkbp5 | -2.1 | 0.0004 | FK506 binding protein 5 |
| NM_011724 | Xirp1 | -2.1 | 0.0004 | Xin actn-binding repeat containing 1 |
| NM_001145858 | Sh3bp2 | -2.1 | 0.0004 | SH3-domain binding protein 2 |
| NM_001037129 | Musk | -2.1 | 0.0004 | Muscle, skeletal receptor tyrosine kinase |
| NM_025341 | Abhd6 | -2.1 | 0.0004 | Abhydidase domain containing 6 |
| NM_010176 | Fah | -2.1 | 0.0004 | Fumarylacetoacetate hydrolase; |
| NM_007923 | Elk4 | -2.1 | 0.0004 | ELK4, member of ETS oncogene family |
| NM_153136 | Nudt18 | -2.1 | 0.0004 | Nudix (nucleoside diphosphate linked moiety X)-type motif 18 |
| NM_016684 | Zscan12 | -2.1 | 0.0004 | Zinc finger and SCAN domain containing 12 |
| NM_001291014 | Zkscan17 | -2.1 | 0.0004 | Zinc finger with KRAB and SCAN domains 17 |
| NM_016972 | Slc7a8 | -2.1 | 0.0004 | Solute carrier family 7 (cationic amino acid transporter, y+ system), member 8 |
| NM_057172 | Fubp1 | -2.1 | 0.0112 | Far upstream element (FUSE) binding protein 1 |
| NM_022882 | Lpin2 | -2.1 | 0.0004 | Lipin 2 |
| NM_011663 | Zrsr1 | -2.1 | 0.0004 | Zinc finger (CCCH type), RNA binding motif and serine/arginine rich 11 |
| NM_016896 | Map3k14 | -2.1 | 0.0004 | Mitogen-activated protein kinase kinase kinase 14 |
| NM_138950 | Wdr81 | -2.1 | 0.0004 | WD repeat domain 81 |
| NR_104298 | Gnl3 | -2.1 | 0.0004 | Guanine, nucleotide binding protein-like 3 (nucleolar) |
| NM_016661 | Ahcy | -2.1 | 0.0004 | S-adenosyl homocysteine hydrolase |
| NM_010757 | Mafk | -2.1 | 0.0004 | V-maf musculoaponeurotic fibrosarcoma oncogene family, protein K (avian) |
| NM_021897 | Trp53inp1 | -2.1 | 0.0004 | Transformation related protein 53 inducible nuclear protein 1 |

FIG. 11(cont.)

| | | | | |
|---|---|---|---|---|
| NM_009025 | Rasa3 | -2.1 | 0.0004 | RAS p21 protein activator 3 |
| NM_133895 | Slc15a4 | -2.1 | 0.0004 | Solute carrier family 15, member 4 |
| NM_053098 | Lmod2 | -2.1 | 0.0004 | Leiomodin 2 (cardiac) |
| NM_052994 | Spock2 | -2.1 | 0.0021 | Sparc/osteonectin,cwcv and kazal-like domains proteoglycan 2 |
| NM_176968 | Nt5dc1 | -2.1 | 0.0004 | 5'-nucleotidase domain containing 1 |
| NM_027493 | Actr8 | -2.1 | 0.0004 | ARP8 actin-related protein 8 homolog (S. cerevisiae) |
| NM_001111099 | Cdkn1a | -2.1 | 0.0004 | Cyclin-dependent kinase inhibitor 1A (P21) |
| NM_001256042 | Hsf4 | -2.1 | 0.0004 | Heat shock transcription factor 4 |
| NM_010100 | Edar | -2.1 | 0.0062 | Ectodysplasin-A receptor |
| NM_007746 | Map3k8 | -2.1 | 0.0004 | Mitogen activated protein kinase kinase kinase 8 |
| NM_023913 | Ern1 | -2.1 | 0.0004 | Endoplasmic retivulum (ER) to nucleus signalling 1 |
| NM_001199733 | Daxx | -2.1 | 0.0004 | Death domain-associated protein 6 |
| NM_007570 | Btg2 | -2.1 | 0.0004 | B-cell translocation gene 2, anti-proliferative |
| NM_019822 | Adrm1 | -2.1 | 0.0004 | Adhesion regulating molecule 1 |
| NM_029415 | Slc10a6 | -2.1 | 0.0004 | Solute carrier family 10 (sodium/bile acid cotransporter family), member 6 |
| NM_001081044 | Mylk2 | -2.1 | 0.0004 | Myosin, light polypeptide kinase 2, skeletal muscle |
| NM_175133 | 1110038D17Rik | -2.1 | 0.0004 | RIKEN cDNA 1110038D17 gene |
| NM_029083 | Ddit4 | -2.1 | 0.0004 | DNA-damase-inducible transcript 4 |
| NM_145135 | Rnh1 | -2.1 | 0.0004 | Ribonuclease/angiogenin inhibitor 1 |
| NM_016736 | Nub1 | -2.1 | 0.0004 | Negative regulator of ubiquitin-like proteins 1 |
| NM_027560 | Arrdc2 | -2.1 | 0.0004 | Arrestin domain containing 2 |
| NM_025514 | Anapcl6 | -2.1 | 0.0004 | n/a |
| NR_044986 | 4933406C10Rik | -2.2 | 0.0004 | RIKEN cDNA 4933406C10 gene |
| NM_008407 | Itih3 | -2.2 | 0.0004 | Inter-alpha trypsin inhibitor, heavy chain 3 |
| NM_010813 | Mnt | -2.2 | 0.0004 | Max binding protein |
| NM_026483 | Mphosph10 | -2.2 | 0.0004 | M-phase phosphoprotein 10 (U3 small nucleolar ribonucleoprotein) |
| NM_001081044 | Mylk2 | -2.2 | 0.0004 | Myosin, light polypeptide kinase 2, skeletal muscle |
| NM_001290727 | Arid5a | -2.2 | 0.0004 | AT rich interactive domain 5A (Mrf1 like) |
| NM_010115 | Klk1b26 | -2.2 | 0.0121 | Kallikrein 1-related peptidase b26 |
| NM_015818 | Hs6st1 | -2.2 | 0.0240 | Heparan sulfate 6-O-sulfotransferase 1 |
| NM_015787 | Hist1h1e | -2.2 | 0.0004 | Histone cluster 1, H1e |
| NM_023422 | Hist1h2be | -2.2 | 0.0004 | Histone cluster 1, H2be |
| NM_177362 | Zfp771 | -2.2 | 0.0004 | Zinc finger protein 771 |
| NM_172713 | Sdad1 | -2.2 | 0.0004 | SDA 1 domain containing 1 |
| NM_007582 | Cacng1 | -2.2 | 0.0004 | Calcium channel, voltage-dependent, gamma subunit 1 |
| NM_020033 | Ankrd2 | -2.2 | 0.0004 | Ankyrin repeat domain 2 (stretch responsive muscle) |
| NM_011874 | Psmc4 | -2.2 | 0.0004 | Proteasome (prosome, macropain) 26S subunit, ATPase,4 |
| NM_172845 | Adamts4 | -2.2 | 0.0004 | A distintegrin-like and metallopeptidase |

FIG. 11(cont.)

| | | | | |
|---|---|---|---|---|
| | | | | (reprolysin type) with thrombospondin type 1 motif, 4 |
| NM_025635 | Zwint | -2.2 | 0.0004 | ZW10 interactor |
| NM_009464 | Ucp3 | -2.2 | 0.0004 | Uncoupling protein 3 (mitochondrial, proton carrier) |
| NM_026853 | Asb11 | -2.2 | 0.0004 | Ankyrin repeat and SOCS box-containing protein 11 |
| NM_001290727 | Arid5a | -2.2 | 0.0060 | AT rich interactive domain 5A (Mrf1 like) |
| NM_183270 | Chchd8 | -2.2 | 0.0004 | Coiled-coil-helix-coiled-coil-helix domain containing 8 |
| NM_153065 | Ddx27 | -2.2 | 0.0004 | DEAD (Asp-Glu-Ala-Asp) box polypeptide 27 |
| NR_027965 | 2310061J03Rik | -2.2 | 0.0155 | RIKEN cDNA 2310061J03 gene |
| NM_133218 | Zfp704 | -2.2 | 0.0004 | Zinc finger protein 704 |
| NM_008694 | Ngp | -2.2 | 0.0004 | Neutrophilic granule protein |
| NM_001272031 | Arvcf | -2.2 | 0.0024 | Armadillo repeat gene deleted in velo-cardio-facial syndrome |
| NM_001164560 | Trmt1 | -2.2 | 0.0004 | TRM1 tRNA methyltransferase 1 homolog (S. cerevisiae) |
| NR_028142 | Pnpla2 | -2.2 | 0.0004 | Patatin-like phospholipase domain containing 2 |
| NM_023248 | Sbds | -2.2 | 0.0004 | Shwachman-Bodian-Diamond syndrome homolog (human) |
| NM_027460 | Slc25a33 | -2.2 | 0.0004 | Solute carrier family 25, member 33 |
| NM_025706 | Tbc1d15 | -2.2 | 0.0004 | TBC1 domain family, member 15 |
| NM_175456 | Abra | -2.2 | 0.0004 | Actin-binding Rho activating protein |
| NM_019930 | Ranbp9 | -2.2 | 0.0004 | RAN binding protein 9 |
| NM_025324 | Zfp524 | -2.2 | 0.0004 | Zinc finger protein 524 |
| NM_177325 | Tsr1 | -2.2 | 0.0004 | TSR1, 20S rRNA accumulation, homolog (yeast) |
| NM_001290698 | Synj2 | -2.2 | 0.0004 | Synaptojanin 2 |
| NR_033450 | Serpina3h | -2.2 | 0.0316 | Serine (or cysteine) peptidase inhibitor, clade A, member 3H |
| NM_199469 | Nploc4 | -2.2 | 0.0004 | Nuclear protein localization 4 homolog (S. cerevisiae) |
| NM_026674 | Aph1c | -2.2 | 0.0004 | Anterior pharynx defective 1c homolog (C, elegans) |
| NM_010234 | Fos | -2.3 | 0.0004 | FBJ osteosarcoma oncogene |
| NM_010908 | Nfkbib | -2.3 | 0.0004 | Nuclear factor of kappa light chain gene enhancer in B-cells inhibitor, beta |
| NR_045702 | AW549542 | -2.3 | 0.0004 | Expressed sequence AW549542 |
| NM_011377 | Sim2 | -2.3 | 0.0004 | Single-minded homolog 2 (Drosophila) |
| NM_009349 | Inmt | -2.3 | 0.0004 | Indolethylamine N-methyltransferase |
| NM_026545 | Psmd8 | -2.3 | 0.0004 | Proteasome (prosome, macropain) 26S subunit, non-ATPase, 8 |
| NM_009272 | Srm | -2.3 | 0.0004 | Spermidine synthase |
| NR_104580 | Slc8a1 | -2.3 | 0.0004 | Solute carrier family 8 (sodium/calcium exchanger), member 1 |
| NM_001146707 | Nap1l1 | -2.3 | 0.0004 | Nucleosome assembly protein 1-like 1 |
| NM_008871 | Serpine1 | -2.3 | 0.0004 | Serine (or cysteine) peptidase inhibitor, clade |

FIG. 11(cont.)

| | | | | E, member 1 |
|---|---|---|---|---|
| NM_009963 | Cry2 | -2.3 | 0.0004 | Cryptochrome 2 (photolyase-like) |
| NM_001081185 | Flnc | -2.3 | 0.0004 | Filamin C, gamma (actin binding protein 280) |
| NM_009238 | Sox4 | -2.3 | 0.0004 | SRY-box containing gene 4 |
| NM_172546 | Cnksr3 | -2.3 | 0.0049 | Cnksr family member 3 |
| NM_008951 | Psmd4 | -2.3 | 0.0004 | Proteasome(prosome, macropain) 26S subunit, non-ATPsae,4 |
| NM_146251 | Pnpla7 | -2.3 | 0.0004 | Patatin-like phospholipase domain containing 7 |
| NM_010321 | Gnmt | -2.3 | 0.0004 | Glycine N-methyltransferase |
| NM_001012322 | Sctr | -2.3 | 0.0004 | Secretin receptor |
| NM_178646 | Tigd5 | -2.3 | 0.0004 | Tigger transposable element derived 5 |
| NM_021462 | Mknk2 | -2.3 | 0.0004 | MAP kinase-interacting serine/threonine kinase 2 |
| NM_133753 | Errfi1 | -2.3 | 0.0004 | ERBB receptor feedback inhibitor 1 |
| NM_145604 | D230025D16Rik | -2.4 | 0.0004 | RIKEN cDNA D230025D16 gene |
| NM_017407 | Spag5 | -2.4 | 0.0004 | Sperm associated antigen 5 |
| NM_001159367 | Per1 | -2.4 | 0.0062 | Period homolog 1 (Drosophila) |
| NM_178045 | Rassf4 | -2.4 | 0.0004 | Ras association (RalGDS/AF-6) domain family 4 |
| NM_001135152 | Slc39al4 | -2.4 | 0.0301 | Solute carrier family 39 (zinc transporter), member 14 |
| NM_011227 | Rab20 | -2.4 | 0.0004 | RAB20, member RAS oncogene family |
| NM_011752 | Zfp259 | -2.4 | 0.0004 | Zinc finger protein 259 |
| NM_019873 | Fkbpl | -2.4 | 0.0004 | FK506 binding protein-like |
| NM_027154 | Tmbim1 | -2.4 | 0.0004 | Transmembrane BAX inhibitor motif containing 1 |
| NM_007970 | Ezh1 | -2.4 | 0.0004 | Enhancer of zeste homolog 1 (Drosophila) |
| NM_001289716 | Bcl2l1 | -2.4 | 0.0004 | Bcl2-like 1 |
| NM_008655 | Gadd45b | -2.4 | 0.0004 | Growth arrest and DNA-damage-inducible 45 beta |
| NM_175164 | Arhgap26 | -2.4 | 0.0004 | Rho GTPase activating protein 26 |
| NM_001033335 | Serpina3f | -2.4 | 0.0384 | Serine (or cysteine) peptidase inhibitor, clade A, member 3F |
| NM_009251 | Serpina3g | -2.4 | 0.0384 | Serine (or cysteine) peptidacse inhibitor, clade A, member 3G |
| NM_001165894 | Akt1 | -2.4 | 0.0004 | Thymoma viral proto-oncogene 1 |
| NM_011728 | Xpa | -2.4 | 0.0004 | Xeroderma pigmentosum, complementation group A |
| NM_028133 | Egln3 | -2.4 | 0.0004 | EGL nine homolog 3 (C.elegans) |
| NM_080575 | Acss1 | -2.4 | 0.0004 | Acyl-CoA synthetase short-chain family member 1 |
| NM_019482 | Panx1 | -2.4 | 0.0004 | Pannexin 1 |
| NM_007428 | Agt | -2.5 | 0.0004 | Angiotensinogen (serpin peptidase inhibitor, clade A, member 8) |
| NM_030063 | Acbd7 | -2.5 | 0.0281 | Acyl-Coenzyme A binding domain containing 7 |
| NM_019739 | Foxo1 | -2.5 | 0.0004 | Forkhead box O1 |
| NM_029836 | Tspyl2 | -2.5 | 0.0004 | TSPY-like 2 |
| NM_001161627 | Tmem116 | -2.5 | 0.0004 | Transmembrane protein 116 |
| NM_013560 | Hspb1 | -2.5 | 0.0004 | Heat shock protein 1 |

FIG. 11(cont.)

| | | | | |
|---|---|---|---|---|
| NM_001081212 | Irs2 | -2.5 | 0.0004 | Insulin receptor substrate 2 |
| NM_025525 | Rnf113a2 | -2.5 | 0.0052 | Ring finger protein 113A2 |
| NM_008416 | Junb | -2.5 | 0.0004 | Jun-B oncogene |
| NM_011969 | Psma7 | -2.5 | 0.0004 | Proteasome (prosome, macropain) subunit, alpha type 7 |
| NM_001001446 | Cyp2c44 | -2.5 | 0.0026 | Cytochrome P450, family 2, subfamily c, polypeptide 44 |
| NM_001081024 | Setdb2 | -2.5 | 0.0004 | SET domain, bifurcated 2 |
| NR_027943 | 1110038B12Rik | -2.5 | 0.0004 | RIKEN cDNA 1110038B12 gene |
| NR_027893 | BB123696 | -2.5 | 0.0011 | Expressed sequence BB123696 |
| NM_016693 | Map3k6 | -2.6 | 0.0004 | Mitogen-activated protein kinase kinase kinase 6 |
| NM_026538 | Ddx56 | -2.6 | 0.0004 | DEAD (Asp-Glu-Ala-Asp) box polypeptide 56 |
| NM_001139520 | Samhd1 | -2.6 | 0.0004 | SAM domain and HD domain, 1 |
| NM_020042 | Mocs1 | -2.6 | 0.0004 | Molybdenum cofactor synthesis 1 |
| NM_173027 | Ip6k3 | -2.6 | 0.0004 | n/a |
| NM_133661 | Slc6a12 | -2.6 | 0.0004 | Solute carrier family 6 (neurotransmitter transporter, betaine/GABA), member 12 |
| NM_025404 | Arl4d | -2.6 | 0.0004 | ADP-ribosylation factor-like 4D |
| NM_028638 | Gadl1 | -2.6 | 0.0004 | Glutamate decarboxylase-like 1 |
| NR_015530 | 9530026P05Rik | -2.6 | 0.0276 | RIKEN cDNA 9530026P05 gene |
| NM_013681 | Syn2 | -2.6 | 0.0325 | Synapsin II |
| NM_019432 | Tmem37 | -2.7 | 0.0004 | Transmembrane protein 37 |
| NM_018737 | Ctps2 | -2.7 | 0.0393 | Cytidin 5' triphosphate synthase 2 |
| NM_009667 | Ampd3 | -2.7 | 0.0004 | AMP deaminase 3 |
| NM_001033302 | Gm129 | -2.7 | 0.0014 | Gene model 129, (NCBI) |
| NM_029774 | Ttll11 | -2.7 | 0.0004 | Tubulin tyrosine ligase-like family, member 11 |
| NM_001081005 | 1500012F01Rik | -2.7 | 0.0004 | RIKEN cDNA 1500012F01 gene |
| NM_001081432 | Ptprq | -2.7 | 0.0174 | Protein tyrosine phosphatase, receptor type, Q |
| NM_001282071 | Sftpb | -2.7 | 0.0008 | Surfactant associated protein B |
| NM_030210 | Aacs | -2.7 | 0.0004 | Acetoacetyl-CoA synthetase |
| NM_183257 | Hamp2 | -2.7 | 0.0004 | Hepcidin antimicrobial peptide 2 |
| NM_001164075 | Tgif1 | -2.8 | 0.0004 | TG interacting factor 1 |
| NM_178909 | Wdr92 | -2.8 | 0.0004 | WD repeat domain 92 |
| NM_020590 | Gabarapl1 | -2.8 | 0.0004 | Gamma-aminobutyric acid [GABA(A)] receptor-associated protein-like 1 |
| NR_024067 | Snhg6 | -2.8 | 0.0004 | Small nucleolar RNA host gene (non-protein coding) 6 |
| NM_001166394 | 4931428F04Rik | -2.8 | 0.0004 | RIKEN cDNA 4931428F04 |
| NM_012017 | Zfp346 | -2.8 | 0.0004 | Zinc finger protein 346 |
| NM_174989 | Ticam1 | -2.8 | 0.0004 | Toll-like receptor adaptor molecule 1 |
| NM_001013370 | Sesn1 | -2.9 | 0.0004 | Sestrin 1 |
| NM_134247 | Acot4 | -2.9 | 0.0204 | Acyl-CoA thioesterase 4 |
| NM_009052 | Bex1 | -2.9 | 0.0004 | Brain expressed gene 1 |
| NM_001184710 | Tfdp2 | -2.9 | 0.0004 | Transcription factor Dp 2 |
| NM_008720 | Npc1 | -2.9 | 0.0004 | Niemann Pick type C1 |
| NM_009252 | Serpina3n | -2.9 | 0.0004 | Serine (or cysteine) peptidase inhibitor, clade A, member 3N |
| NM_144536 | Cdka1l | -2.9 | 0.0004 | CDK5 regulatory subunit associated protein |

FIG. 11(cont.)

| | | | | |
|---|---|---|---|---|
| NM_007679 | Cebpd | -2.9 | 0.0004 | CCAAT/enhancer binding protein (C/EBP), delta |
| NM_020581 | Angptl4 | -3.0 | 0.0004 | Angiopoietin-like 4 |
| NM_026346 | Fbxo32 | -3.0 | 0.0004 | F-box protein 32 |
| NM_028770 | Krt80 | -3.0 | 0.0004 | Keratin 80 |
| NM_001159324 | Gaa | -3.0 | 0.0004 | Glucosidase, alpha, acid |
| NM_011510 | Abcc8 | -3.0 | 0.0004 | ATP-binding cassette, sub-family C (CFTR/MRP), member 8 |
| NM_001289632 | Itih4 | -3.0 | 0.0004 | Inter alpha-trypsin inhibitor, heavy chain 4 |
| NR_038151 | 2410004N09Rik | -3.1 | 0.0004 | RIKEN cDNA 2410004N09 gene |
| NM_181593 | Itpkc | -3.1 | 0.0004 | Inositol 1,4,5-trisphosphate 3-kinase C |
| NM_010755 | Maff | -3.1 | 0.0004 | V-maf musculoaponeurotic fibrosarcoma oncogene family, protein F (avian) |
| NM_007918 | Eif4ebp1 | -3.2 | 0.0155 | Eukaryotic translation initiation factor 4E binding protein 1 |
| NM_029799 | Arrdc5 | -3.2 | 0.0004 | Arrestin domain containing 5 |
| NM_177755 | Klh138 | -3.2 | 0.0126 | n/a |
| NM_001282006 | Tekt1 | -3.2 | 0.0004 | Tektin 1 |
| NM_008252 | Hmgb2 | -3.2 | 0.0004 | High mobility group box 2 |
| NM_201610 | Neil2 | -3.2 | 0.0004 | Nei like 2 (E. coli) |
| NM_029035 | Spsb1 | -3.2 | 0.0004 | SplA/ryanodine receptor domain and SOCS box containing 1 |
| NM_025427 | 1190002H23Rik | -3.3 | 0.0004 | RIKEN cDNA 1190002H23 gene |
| NM_001081219 | Myo1a | -3.3 | 0.0449 | Myosin 1A |
| NM_009117 | Saa1 | -3.3 | 0.0004 | Serum amyloid A 1 |
| NM_001287386 | Gck | -3.3 | 0.0004 | Glucokinase |
| NM_008244 | Hgs | -3.3 | 0.0004 | HGF-regulated tyrosine kinase substrate |
| NM_021542 | Kcnk5 | -3.3 | 0.0004 | Potassium channel, subfamily k, member 5 |
| NM_197980 | Cox19 | -3.3 | 0.0004 | COX 19 cytochrome c oxidase assembly homolog (S, cerevisiae) |
| NM_007918 | Eif4cbp1 | -3.3 | 0.0004 | Eukaryotic translation initiation factor 4E |
| NM_145980 | 8430408G22Rik | -3.3 | 0.0004 | RIKEN cDNA 8430408G22 gene |
| NM_033596 | Hist2h4 | -3.4 | 0.0004 | Histone cluster 2, H4 |
| NM_146186 | Wdr62 | -3.4 | 0.0004 | WD repeat domain 62 |
| NM_053110 | Gpnmb | -3.4 | 0.0004 | Glycoprotein (transmembrane) nmb |
| NM_011314 | Saa2 | -3.4 | 0.0004 | Serum amyloid A 2 |
| NM_001291058 | Cd68 | -3.4 | 0.0004 | CD68 antigen |
| NM_012006 | Acot1 | -3.4 | 0.0004 | Acyl-CoA thioesterase 1 |
| NM_134188 | Acot2 | -3.4 | 0.0004 | Acyl-CoA thioesterase 2 |
| NM_177093 | Lrrc58 | -3.4 | 0.0004 | Leucine rich repeat containing 58 |
| NM_026779 | Mocos | -3.4 | 0.0004 | Molybdenum cofactor sulfurase |
| NM_009154 | Sema5a | -3.4 | 0.0004 | Sema domain, seven thrombospondin repeats (type 1 and type 1-like), transmembrane domain |
| NM_146578 | Olfr1033 | -3.4 | 0.0004 | Olfactory receptor 1033 |
| NM_029290 | 1700011I03Rik | -3.4 | 0.0176 | RIKEN cDNA 1700011I03 |
| NM_013468 | Ankrd1 | -3.6 | 0.0004 | Ankyrin repeat domain 1 (cardiac muscle) |
| NM_029774 | Ttll11 | -3.6 | 0.0198 | Tubulin tyrosine ligase-like family, member 11 |

FIG. 11(cont.)

| | | | | |
|---|---|---|---|---|
| NM_010559 | Il6ra | -3.6 | 0.0004 | Interleukin 6 receptor, alpha |
| NM_010559 | Il6ra | -3.6 | 0.0004 | Interleukin 6 receptor, alpha |
| NM_001135152 | Slc39a14 | -3.7 | 0.0004 | Solute carrier family 39 (zinc transporter), member 14 |
| NM_146578 | Olfrl033 | -3.8 | 0.0329 | Olfactory receptor 1033 |
| NM_015803 | Atp8a2 | -3.8 | 0.0470 | ATPase, aminophospholipid transporter-like, class 1, type 8A, member 2 |
| NM_019701 | Clcnkb | -3.8 | 0.0004 | Chloride channel Kb |
| NM_144821 | AI317395 | -3.9 | 0.0004 | Expressed sequence AI317395 |
| NM_001039048 | Trim63 | -3.9 | 0.0004 | Tripartite motif-containing 63 |
| NM_181390 | Mustn1 | -3.9 | 0.0004 | Musculoskeletal, embryonic nuclear protein 1 |
| NM_011315 | Saa3 | -4.0 | 0.0004 | Serum amyloid A 3 |
| NM_203492 | Mrgprg | -4.0 | 0.0004 | MAS-related GPR, member G |
| NM_177028 | 5330437I02Rik | -4.1 | 0.0004 | RIKEN cDNA 5330437I02 gene |
| NM_023065 | Ifi30 | -4.1 | 0.0004 | Interferon gamma inducible protein 30 |
| NM_001081219 | Myo1a | -4.1 | 0.0004 | Myosin 1A |
| NM_001081047 | Cnksr1 | -4.1 | 0.0004 | Connector enhancer of kinase suppressor of Ras 1 |
| NM_008796 | Pctp | -4.1 | 0.0085 | Phosphatidylcholine transfer protein |
| NM_010100 | Edar | -4.2 | 0.0340 | Ectodysplasin-A receptor |
| NM_001256489 | 9030624G23Rik | -4.2 | 0.0004 | RIKEN cDNA 9030624G23 gene |
| NR_030738 | 2410006H16Rik | -4.2 | 0.0004 | RIKEN cDNA 2410006H16 gene |
| NM_023557 | Slc44a4 | -4.3 | 0.0004 | Solute carrier family 44, member 4 |
| NM_011366 | Sorbs3 | -4.3 | 0.0004 | Sorbin and SH3 domain containing 3 |
| NM_175643 | Adamts2 | -4.4 | 0.0004 | A distinte grin-like and metallopeptidase (reprolysin type) with thrombospondin type 1 motif, 2 |
| NM_007873 | Doc2b | -4.7 | 0.0004 | Double C2, beta |
| NM_175681 | Glp2r | -4.7 | 0.0004 | Glucagon-like peptide 2 receptor |
| NM_008630 | Mt2 | -4.8 | 0.0004 | Metallothionein 2 |
| NM_008491 | Lcn2 | -4.9 | 0.0004 | Lipocalin 2 |
| NM_177028 | 5330437I02Rik | -4.9 | 0.0004 | RIKEN cDNA 5330437I02 gene |
| NM_007873 | Doc2b | -5.1 | 0.0004 | Double C2. beta |
| NR_038011 | C730036E19Rik | -5.2 | 0.0004 | RIKEN cDNA C730036E19 gene |
| NM_013602 | Mt1 | -5.2 | 0.0004 | Metallothionein 1 |
| NM_027211 | Anxa13 | -5.4 | 0.0008 | Annexin A13 |
| NM_011104 | Prkce | -7.0 | 0.0004 | Protein kinase C, epsilon |

FIG. 11(cont.)

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacaccagca tccagttcaa                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggttcagtag gccattcctc                                                  20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacattctct cctggaaggg c                                                21

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 4
ttgataaagt cttgagggga aagtg                                          25

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcaattcgc cacaatctgt cc                                             22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggtgatttt ccgctcttgc                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggccttc cgtgttccta                                                20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggcacgtc agatcca                                                   17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcccggtgg cccagtacca                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgcactgggg cgaggacact                                          20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgttccag tacgccagca c                                        21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtgcgtggg gtgagtgcat aa                                       22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacgaagacg agaagatcaa catc                                     24

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccccaaac accttgca                                            18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccaacatcac aagaaatgc                                           19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
tacaaacatc atcacgttcc                                                   20

<210> SEQ ID NO 17
<211> LENGTH: 4
<212> TYPE: PRT
<213> ORGANISM: Unknown
<220> FEATURE:
<223> OTHER INFORMATION: Description of Unknown: 'DEAD' box
      peptide

<400> SEQUENCE: 17

Asp Glu Ala Asp
1
```

METHODS FOR SUPPRESSING CANCER-RELATED CACHEXIA

PRIORITY CLAIM

This application claims priority to U.S. Provisional Patent Application Ser. No. 61/906,738 filed on Nov. 20, 2013. The above referenced application is incorporated herein by reference as if restated in full. All references cited herein, including, but not limited to patents and patent applications, are incorporated by reference in their entirety.

SEQUENCE LISTING

The instant application contains a Sequence Listing which has been submitted electronically in ASCII format and is hereby incorporated by reference in its entirety. Said ASCII copy, created on Dec. 23, 2014, is named AR000005.USU1SL.txt and 4 kilobytes in size.

BACKGROUND

Cancer-related cachexia is a debilitating condition associated with loss of muscle mass, fatigue, weakness, and loss of appetite in cancer patients. Cachexia is also associated with severe clinical consequences including muscle weakness which can result in ambulation difficulties, and pulmonary complications. Cachexia is a significant contributing factor in the death of cancer patients.

Cachexia is characterized by depletion of skeletal muscle mass that is not reversed by conventional nutritional support, leading to pronounced weight loss that severely impacts patient morbidity and mortality. It occurs in more than 80% of patients with gastric, pancreatic, and esophageal cancer; 70% of those with head and neck cancer; and approximately 60% of patients with lung, colorectal, and prostate cancer. See., e.g., Muscle (2012) 3, 245-51. Despite cachexia's impact on mortality among cancer patients, no effective therapies have been developed to prevent or impede the progression of cachexia. For example, more than 85% of pancreatic cancer patients, including early stage patients, are estimated to lose an average of 14% of their pre-illness weight. See e.g., BMC Cancer. 2010 Jul. 8; 10:363. Cachectic pancreatic cancer patients are often weak and fatigued, and have a lower tolerance to therapy and more adverse outcomes to surgery. Consequently, cachexia is the main driver for mortality in pancreas cancer. Sadly, the 5-year survival rate for pancreatic cancer remains at 6% for the last four decades, which is the lowest among all malignancies.

With the advent of new tools to identify cachectic factors and their effects on skeletal muscle, the field of cachexia has recently made significant advances in understanding the underlying mechanisms that regulate muscle atrophy in cancer and other chronic illnesses. As a result, we now have an appreciation for how cytokines and systemic inflammation regulate muscle atrophy by acting on key signaling pathways that operate from inside the myofiber. However, translating these discoveries into effective therapies has been challenging, and, prior to the aspects described herein, an effective treatment for cachexia has been lacking.

Skeletal muscle mass is regulated, in part, by the relative rate of protein synthesis versus protein regulation. Alamdari, N, et al., Acetylation and deacetylation—novel factors in muscle wasting, Metabolism. January 2013; 62(1): 1-11. Loss of skeletal muscle mass occurs when the rate of protein degradation is greater than protein synthesis. Id. Protein acetylation and deacetylation modify transcription factors and gene transcription which may influence muscle mass by rendering proteins more or less susceptible to degradation. Id. Histone acetylases (HATs) and histone deacetylases (HDACs) play a role in regulating protein acetylation and deacetylation.

However, the effects of these molecules on muscle wasting and cachexia have proven to be contradictory—evidence suggests, for example, that use of HDAC inhibitors (e.g., Trichostatin A (TSA)) results in hyperacetylation which can increase protein degradation leading to increased muscle wasting and cachexia. Contradictory results were found by Narver et. al., (Sustained improvement of spinal muscular atrophy mice treated with trichostatin A plus nutrition. Ann Neurol. 2008; 64:465-70) however, these results have been questioned because treatment with TSA was also accompanied by aggressive nutritional support. Alamdari et al., at 5. Thus, HDAC inhibitors were thought to increase rather than decrease cachexia or their use produced conflicting and contradictory results.

The development and progression of cancer cachexia is caused by complex, multifactorial pathophysiological responses to tumors in muscle tissues. To date, no FDA-approved therapies are available to prevent or hamper the progression of muscle wasting in cachectic patients. To date, several investigational drugs, which target different aspects of cachexia pathogenesis, have undergone human trials, however, with different clinical outcomes. For example, while Novartis's BYM38 (bimagrumab), a mAb that blocks binding of myostatin and activin to type II activin receptors, received FDA breakthrough therapy designation, GTx's muscle wasting drug enobosarm, a selective androgen receptor modulator, failed in late-stage clinical trials.

Acetylation of core histones plays an important role in the regulation of gene transcription by controlling nucleosomal packaging of DNA. Deacetylation of histones results in tight packing of nucleosomes and transcriptional repression due to limited access of transcription factors to DNA targets. Histone acetylation relaxes nucleosome structures, providing greater access for transcription factors. The balance between histone deacetylation and acetylation is modulated by the histone deacetyl-transferases (HDACs) and histone acetyl-transferases (HAT). An abnormal balance of these factors is correlated with abnormal cell growth and several forms of cancer as discussed in U.S. Pat. No. 8,318,808, incorporated by reference herein in its entirety. HDAC inhibitors, in particular, change the balance between acetylation and deacetylation resulting in growth arrest, differentiation, and apoptosis in many tumor cell types. See, e.g., U.S. Pat. No. 8,318,808.

18 HDACs have been identified in humans and are characterized as being zinc dependent or nicotinamide adenine dinucleotide (NAD) dependent (Discov Med 10(54):462-470, November 2010) and are associated with the following classes: class I (HDACs 1, 2, 3, and 8); class II (HDACs 4, 5, 6, 7, 9, and 10; class III (sirtuins 1-7 (SIRT)); and class IV (HDAC 11). Id.

Of particular interest herein are HDAC inhibitors described in U.S. Pat. No. 8,318,808 and are based on, for example, fatty acids coupled with $Zn^{2+}$-chelating motifs through aromatic Ω-amino acid linkers. In various aspects, the HDAC inhibitors may have the formula:

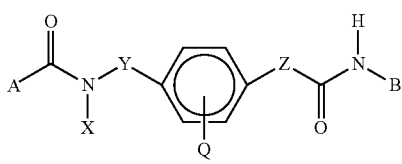

wherein X is chosen from H and CH3; Y is (CH2)n wherein n is 0-2; Z is chosen from (CH2)m wherein m is 0-3 and (CH)2; A is a hydrocarbyl group; B is o-aminophenyl or hydroxyl group; and Q is a halogen, hydrogen, or methyl. One HDAC inhibitor of particular (N-hydroxy-4-(3-methyl-2-phenyl-butyrylamino)-benzamide) is also known as AR-42. In one aspect, the structure of AR-42 is as follows:

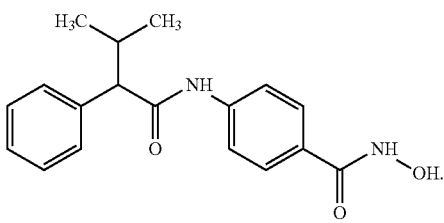 [SMILES: CC(C)C(C(=O)Nc1ccc(C(=O)NO)cc1)c1ccccc1]

AR-42 is a broad-spectrum deacetylase inhibitor of both histone and non-histone proteins with demonstrated greater potency and activity in solid tumors and hematological malignancies when compared to vorinostat (i.e., SAHA). See, e.g., Lu Y S, et al., Efficacy of a novel histone deacetylase inhibitor in murine models of hepatocellular carcinoma, Hepatology. 2007 October; 46(4):1119-30; Kulp S K, et al., Antitumor effects of a novel phenylbutyrate-based histone deacetylase inhibitor, (S)-HDAC-42, in prostate cancer, Clin Cancer Res. 2006 Sep. 1; 12(17):5199-206.

AR-42 may also possess additional histone-independent mechanisms which contribute to its therapeutic profile. See, e.g., Chen M C, et al., Novel mechanism by which histone deacetylase inhibitors facilitate topoisomerase IIα degradation in hepatocellular carcinoma cells, Hepatology. 2011 January; 53(1):148-59; Chen C S, et al., Histone acetylation-independent effect of histone deacetylase inhibitors on Akt through the reshuffling of protein phosphatase 1 complexes, J Biol Chem. 2005 Nov. 18; 280(46):38879-87; Yoo C B, et al., Epigenetic therapy of cancer: past, present and future, Nat Rev Drug Discov. 2006 January; 5(1):37-50.

AR-42 has a demonstrated inhibitory effect in tumors including, but not limited to, breast, prostate, ovarian, blood cell (e.g., lymphoma, myeloma, and leukemia), liver, and brain. See, e.g., Mims A, et. al., Increased anti-leukemic activity of decitabine via AR-42-induced upregulation of miR-29b: a novel epigenetic-targeting approach in acute myeloid leukemia, Leukemia. 2012 Nov. 26. doi: 10.1038/leu.2012.342. [Epub ahead of print]; Burns S S, et al., Histone deacetylase inhibitor AR-42 differentially affects cell-cycle transit in meningeal and meningioma cells, potently inhibiting NF2-deficient meningioma growth, Cancer Res. 2013 Jan. 15; 73(2):792-803; Lu Y S, et. al., Radiosensitizing effect of a phenylbutyrate-derived histone deacetylase inhibitor in hepatocellular carcinoma, Int J Radiat Oncol Biol Phys. 2012 Jun. 1; 83(2); Zimmerman B, et. al., Efficacy of novel histone deacetylase inhibitor, AR42, in a mouse model of, human T-lymphotropic virus type 1 adult T cell lymphoma, Leuk Res. 2011 November; 35(11):1491-7; Zhang S, et al., The novel histone deacetylase inhibitor, AR-42, inhibits gp130/Stat3 pathway and induces apoptosis and cell cycle arrest in multiple myeloma cells, Int J Cancer. 2011 Jul. 1; 129(1):204-13.

SUMMARY

Aspects described herein provide methods of suppressing cachexia in a mammal with cancer comprising administering a HDAC class 1 and 2b inhibitor to said mammal. One aspect provides a method of suppressing cachexia in a mammal with cancer by administering a HDAC class 1 and 2b inhibitor to said mammal in an amount effective to substantially maintain the mammal's weight compared to a mammal that does not receive the HDAC class 1 and 2b inhibitor. In another aspect, the HDAC class 1 and 2b inhibitor is administered to a mammal with cancer in an amount effective to substantially maintain at least about 90% of said mammal's weight over a period of time of at least fifteen days. In another aspect, the HDAC class 1 and 2b inhibitor is AR-42. In yet another aspect, the mammal with cancer has at least one tumor and the tumor volume is not reduced by more than 6% during about the first fifteen days following treatment with AR-42.

Other aspects described herein provide methods of suppressing cachexia by administering AR-42 to a mammal with cancer wherein the expression of multiple mediators of muscle atrophy (e.g., pro-cachexia drivers such as IL-6, IL-6Rα, LIF, MuRF1, Atrogin-I) in cancer cachexia is reduced compared to a mammal having cancer that is not treated with AR-42.

Further aspects provide methods of suppressing cachexia by administering AR-42 to a mammal with cancer wherein cachexia-induced loss of adipose tissue and reduction in skeletal muscle fiber size is substantially restored compared to a mammal that does not receive AR-42.

Aspects described herein provide methods of maintaining skeletal muscle weight in a mammal having cancer by administering a HDAC class 1 and 2b inhibitor to said mammal in an amount effective to maintain at least about 90% of said mammal's skeletal muscle weight over a period of time of at least fifteen days compared to a mammal that does not receive the HDAC class 1 and 2b inhibitor.

Further aspects provide methods of prolonging survival of a mammal having cancer by administering a HDAC class 1 and 2b inhibitor to the mammal in an amount effective to substantially prolong survival of the mammal compared to a mammal that does not receive the HDAC class 1 and 2b inhibitor.

As disclosed herein, AR-42 shows in vivo efficacy in suppressing, reducing, or blocking muscle wasting and prolonging survival in animal models of cancer cachexia. In addition, the effect of AR-42 on cancer-related cachexia is independent of AR-42's effects on reducing tumor load.

FIGURES

FIG. 1A shows exemplary suppression of cancer-induced cachexia in C-26 tumor-bearing mice and depicts changes in total weight (left, tumor included) and body weight (center, tumor excluded) during the 15-day study in vehicle-treated tumor-free mice (Control) versus tumor-bearing mice treated with vehicle (Vehicle) or oral AR-42 at 50 mg/kg every other day (AR-42). Arrows indicate the times of AR-42 treatment. Right, lack of suppressive effect of AR-42 on tumor growth in C-26 tumor-bearing mice. Data are presented as means±S.D. P values: a, 0.045; b, 0.0027; c, 0.049; d, 0.0048;

Figure 2A:
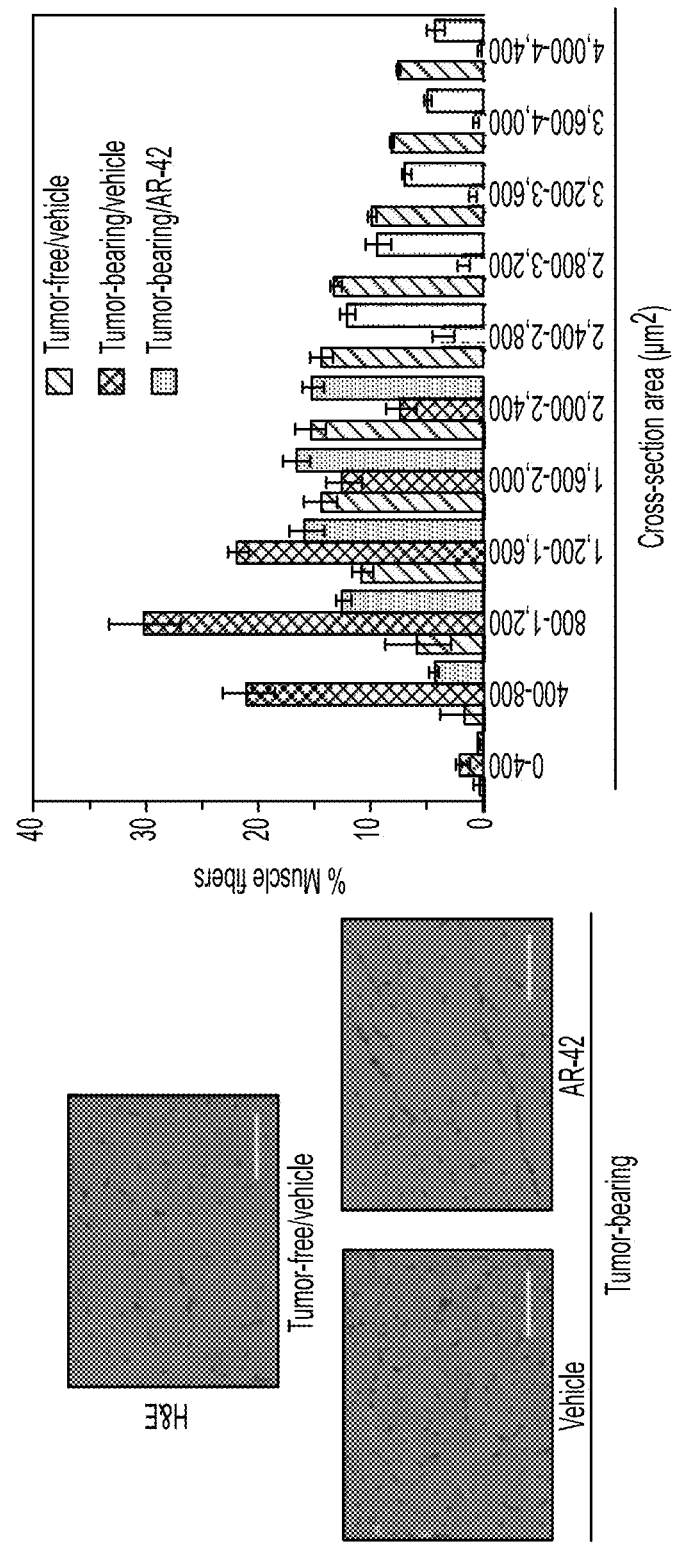
Figure 2B:
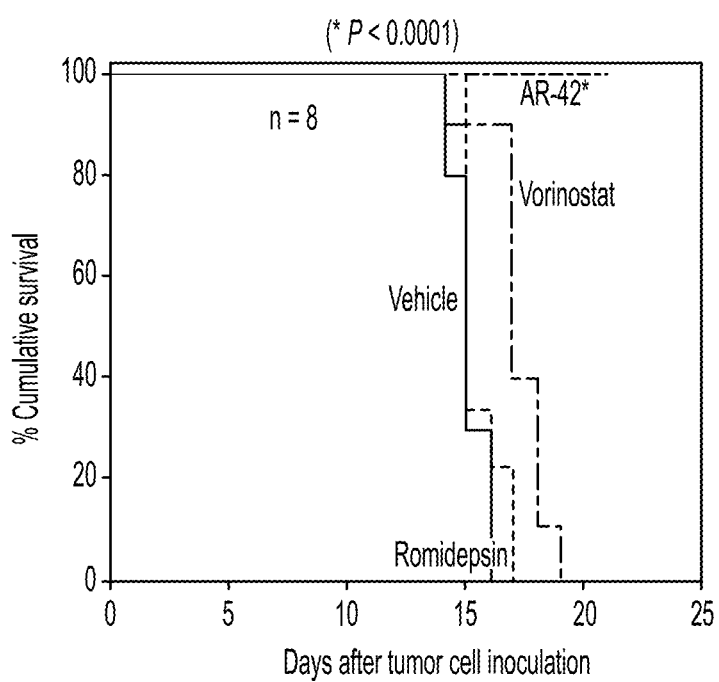
Figure 2C:
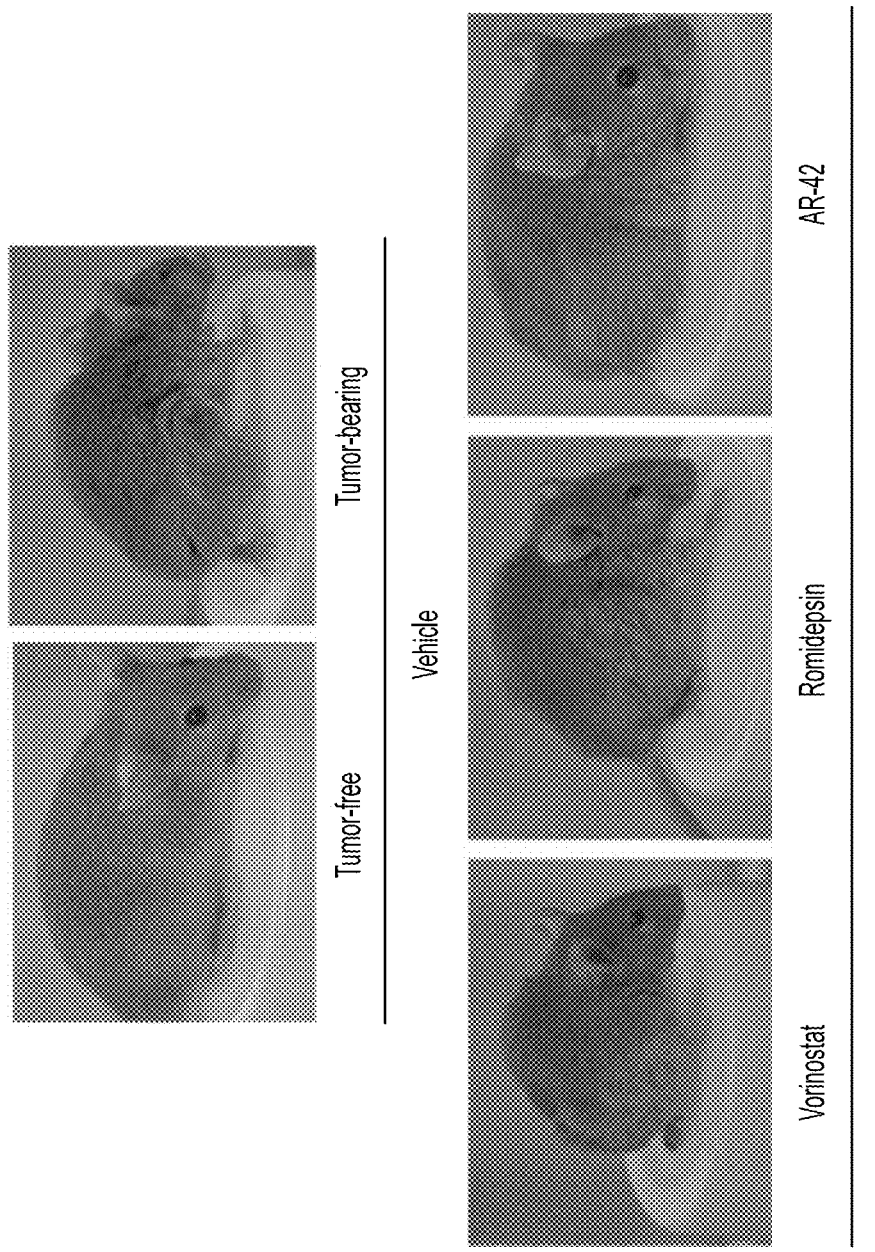
Figure 2D:
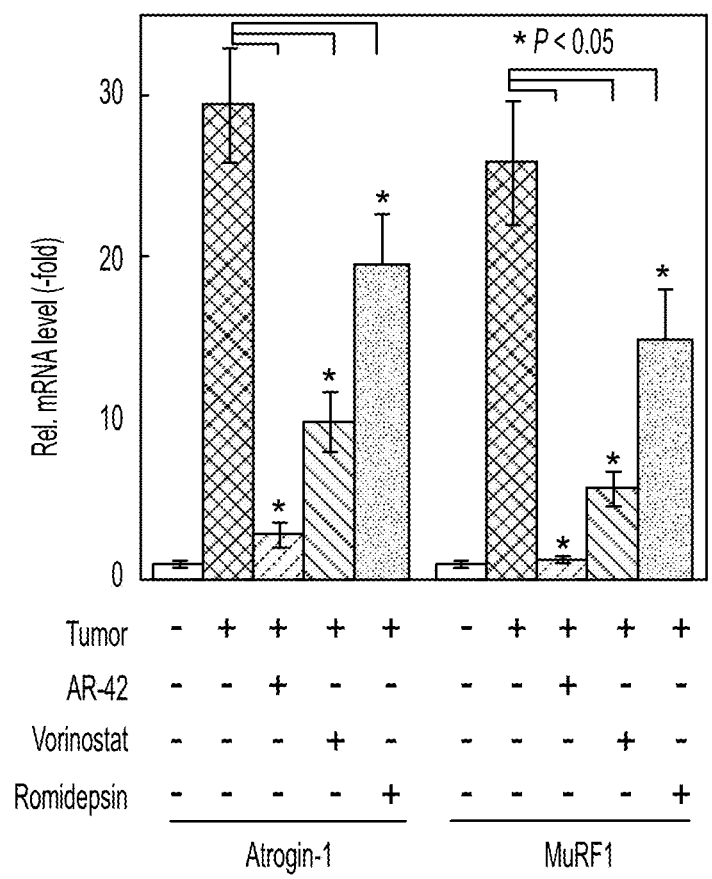
Figure 3A:
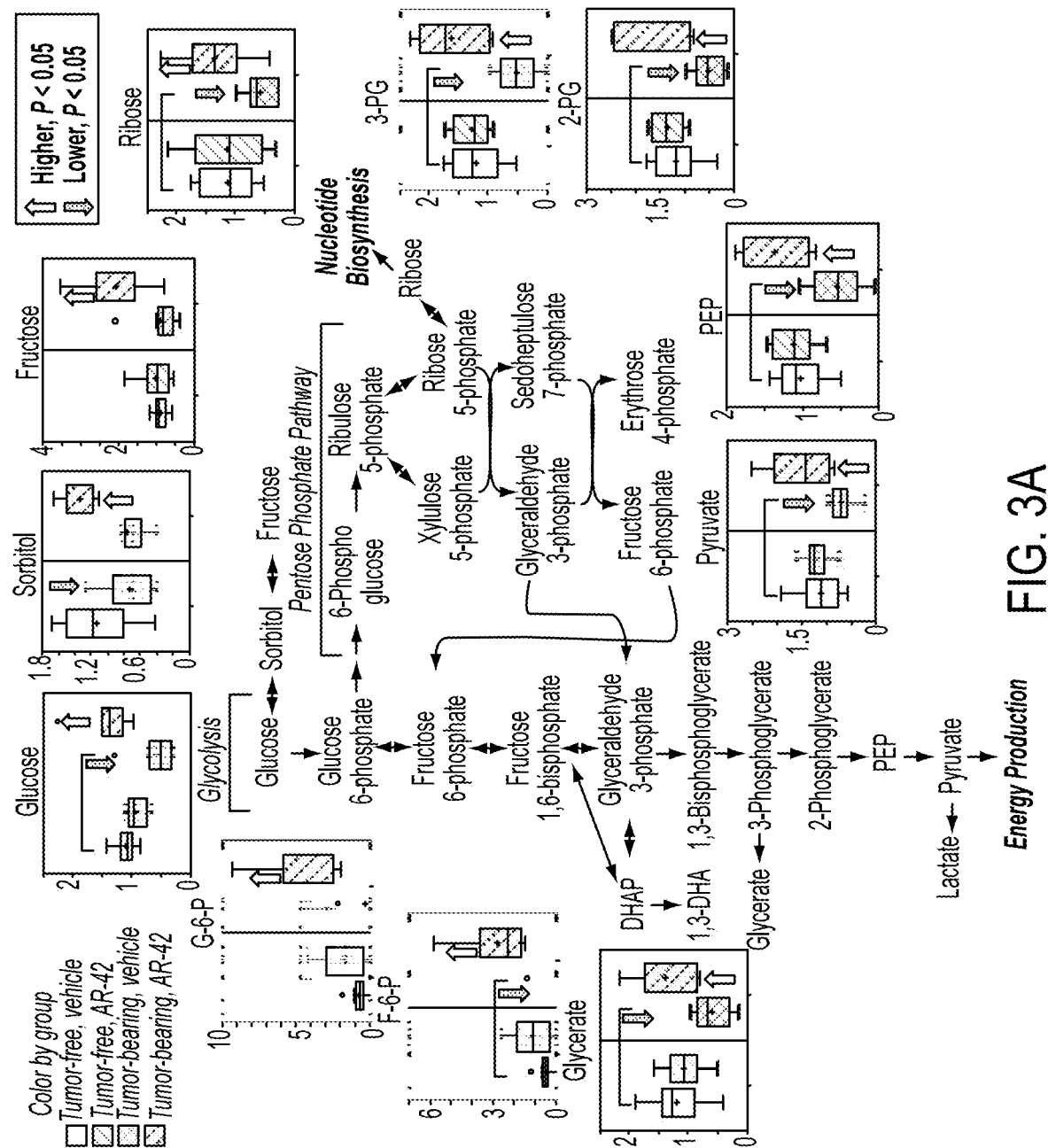
Figure 3B:
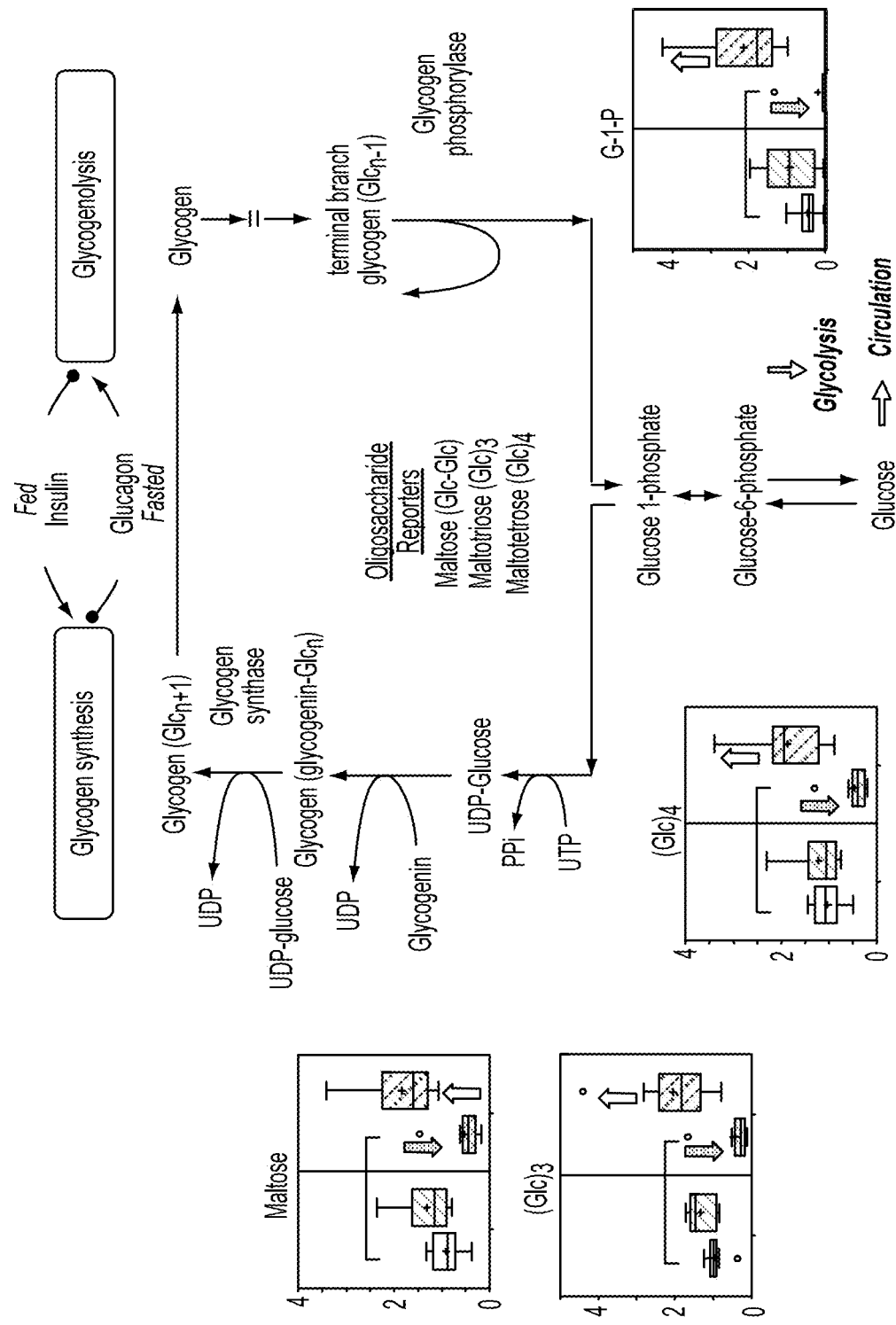
Figure 4:
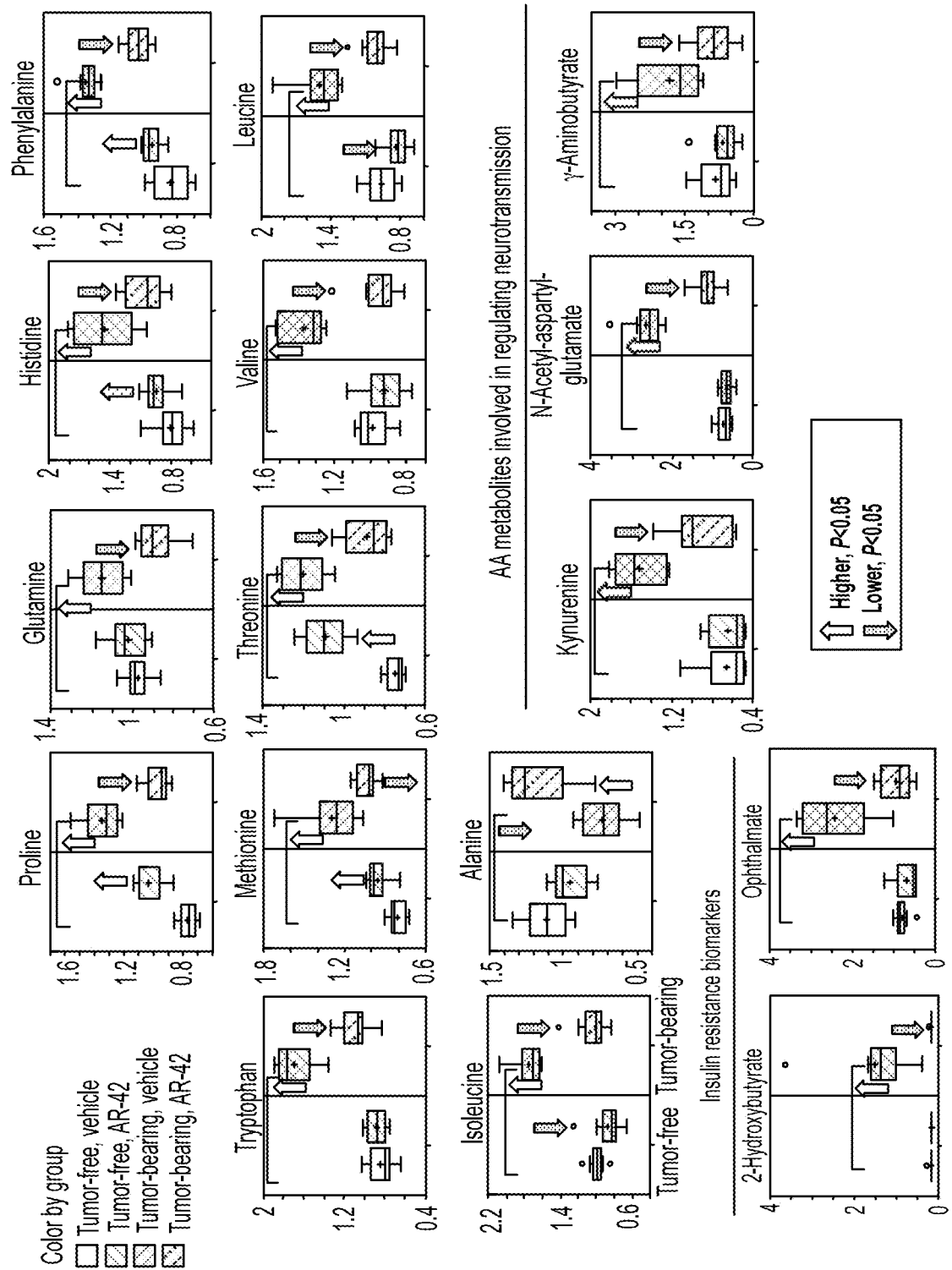
Figure 5A:
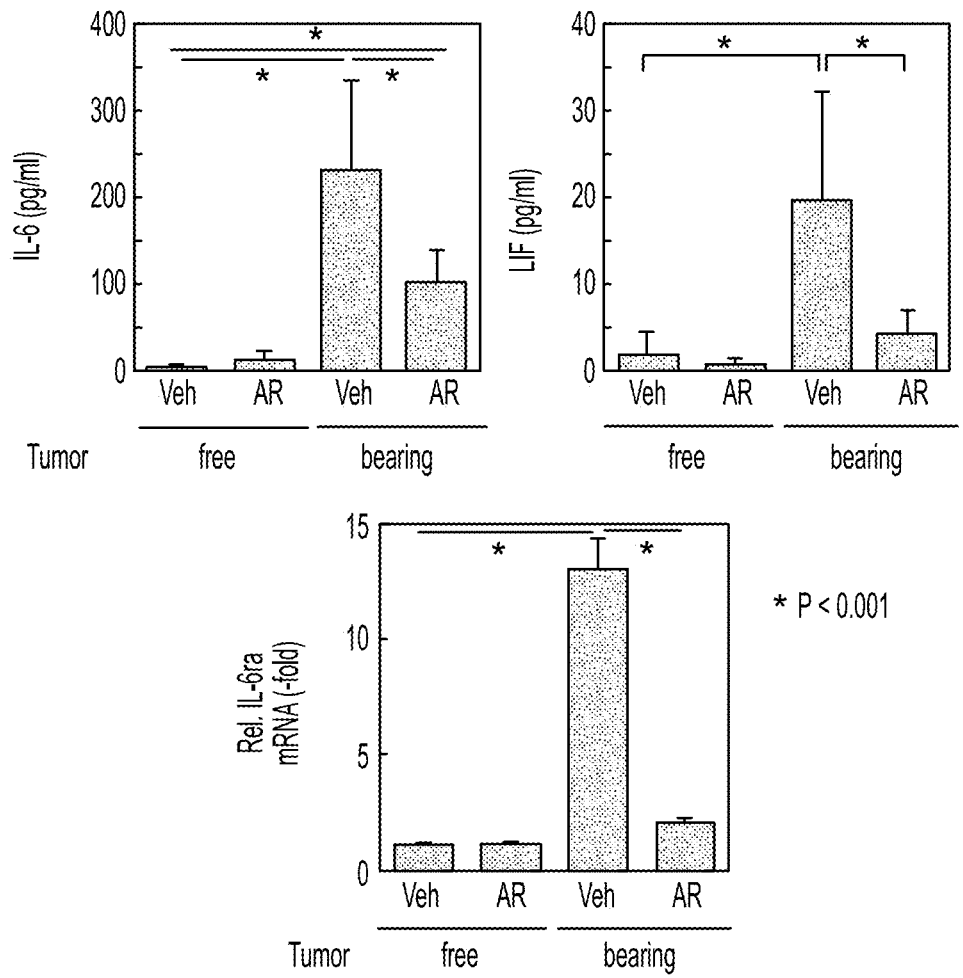
Figure 5B:
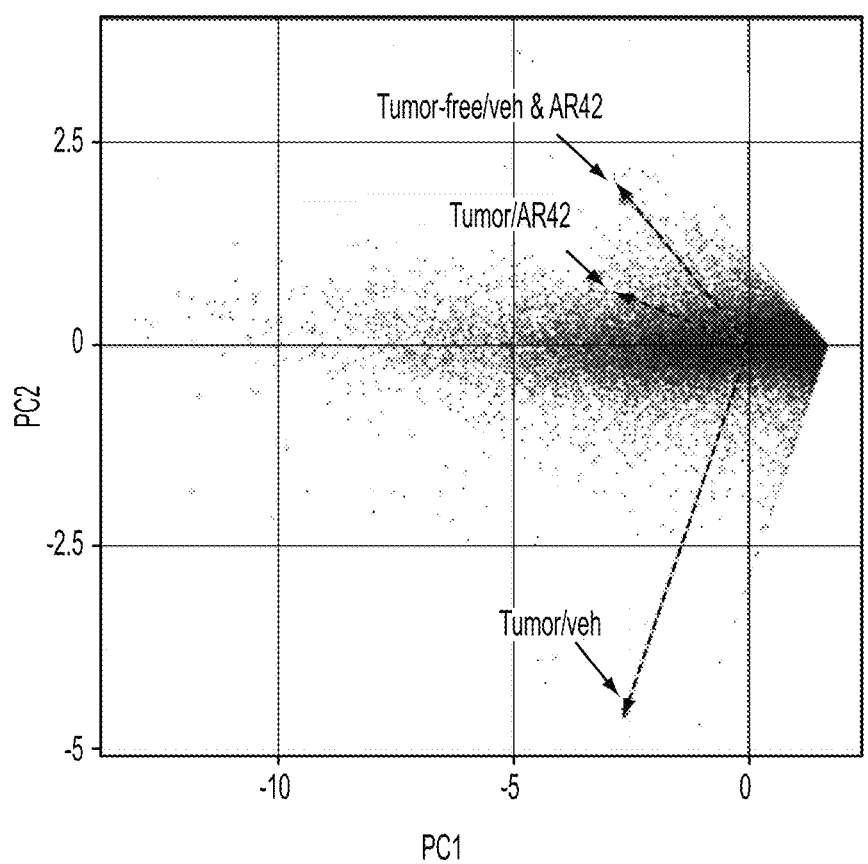
Figure 5C:
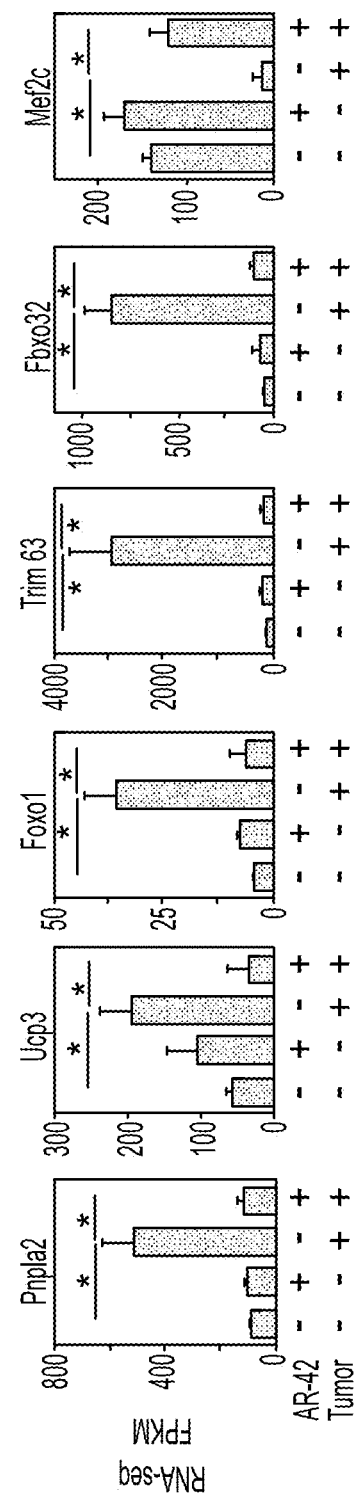
Figure 5D:
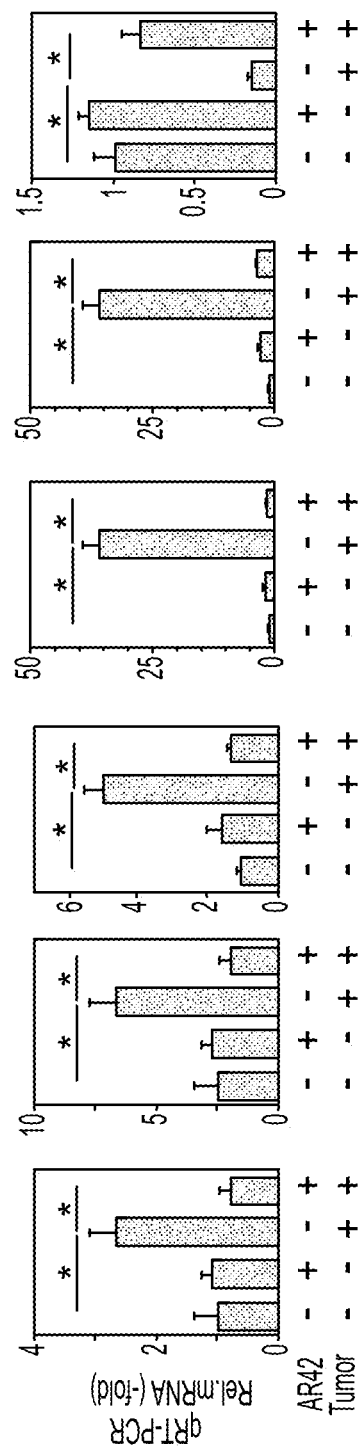
Figure 6A:
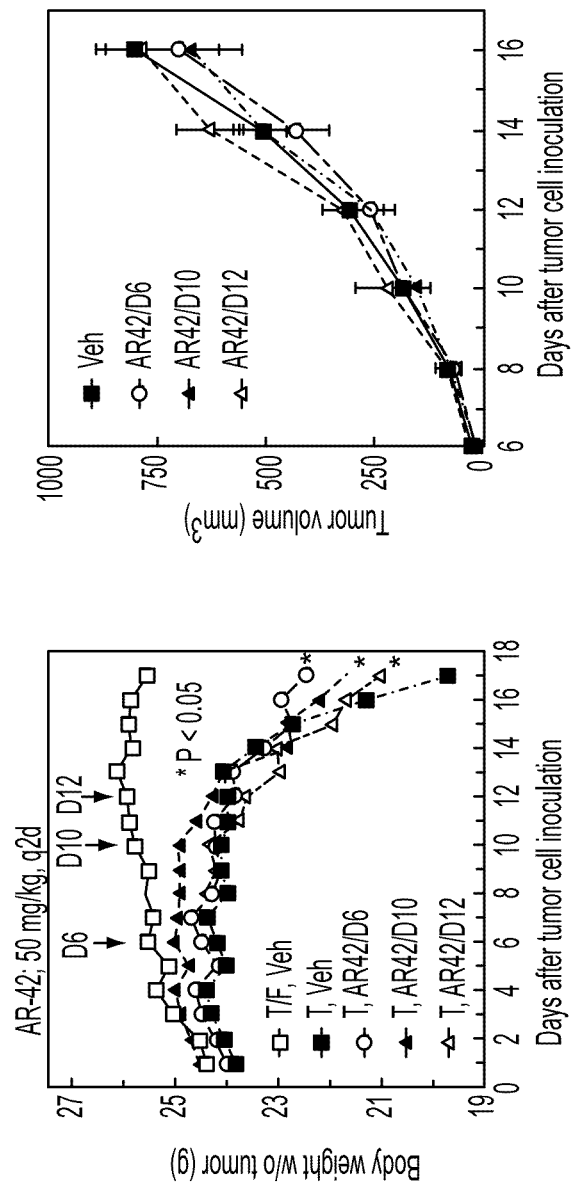
Figure 6B:
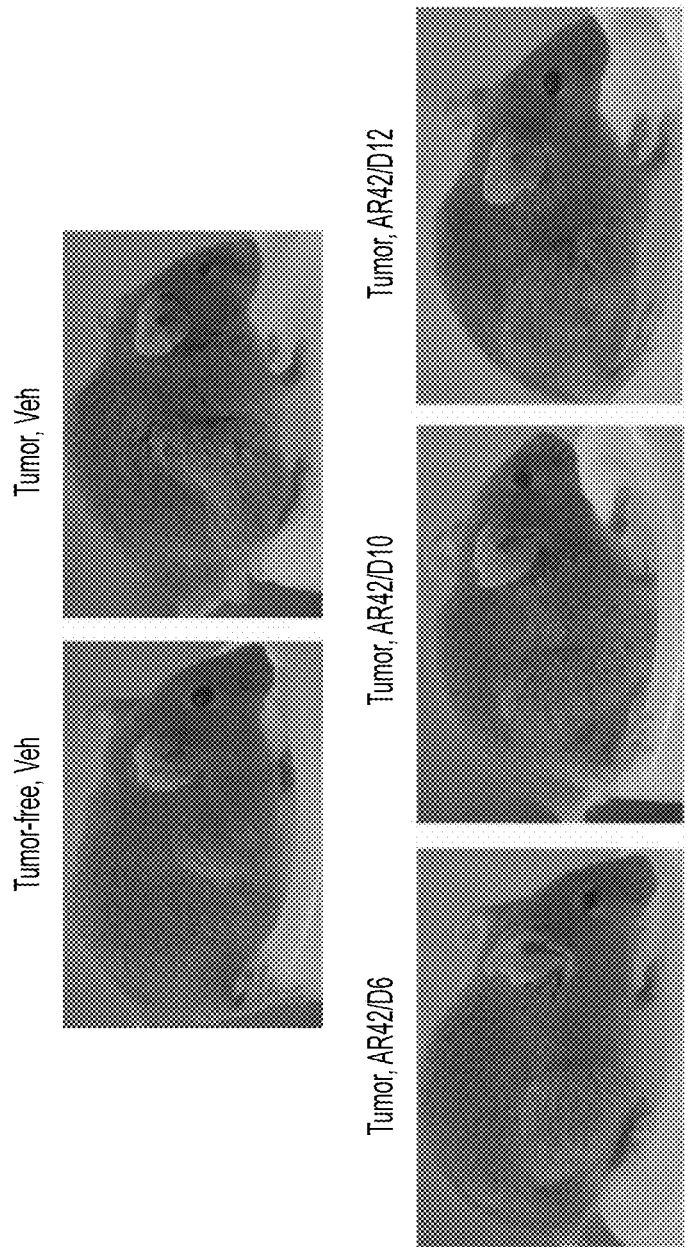
Figure 6C:
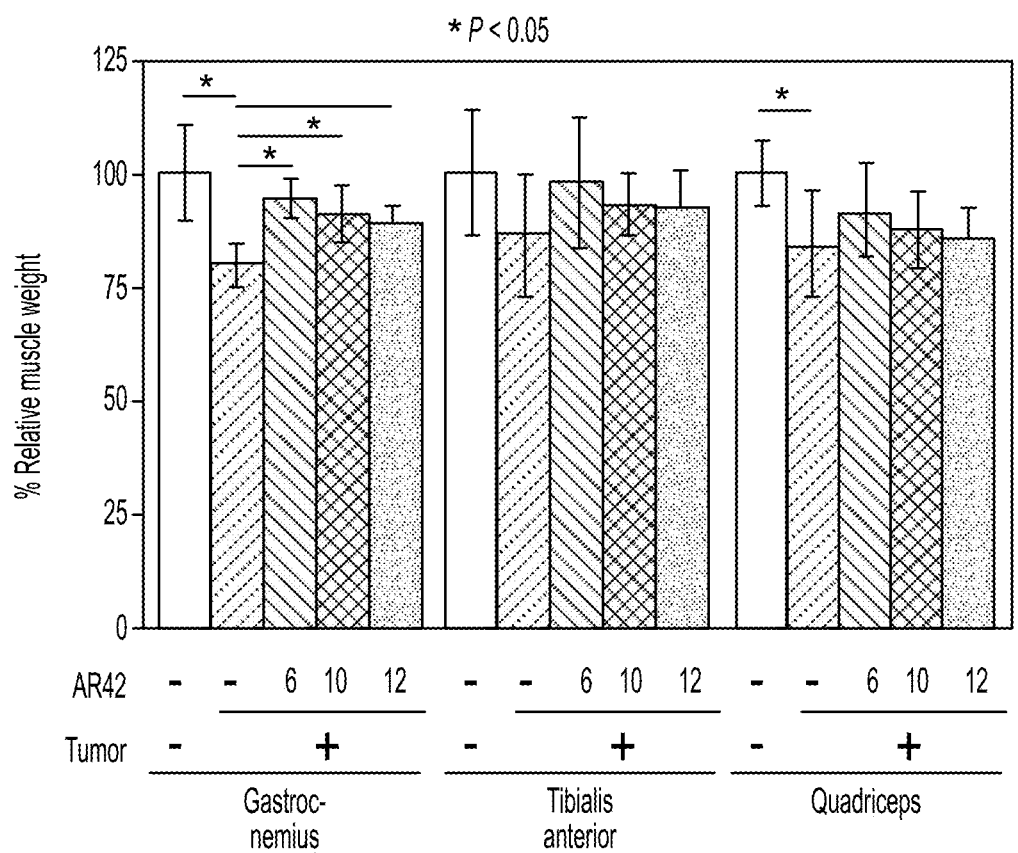
Figure 6D:
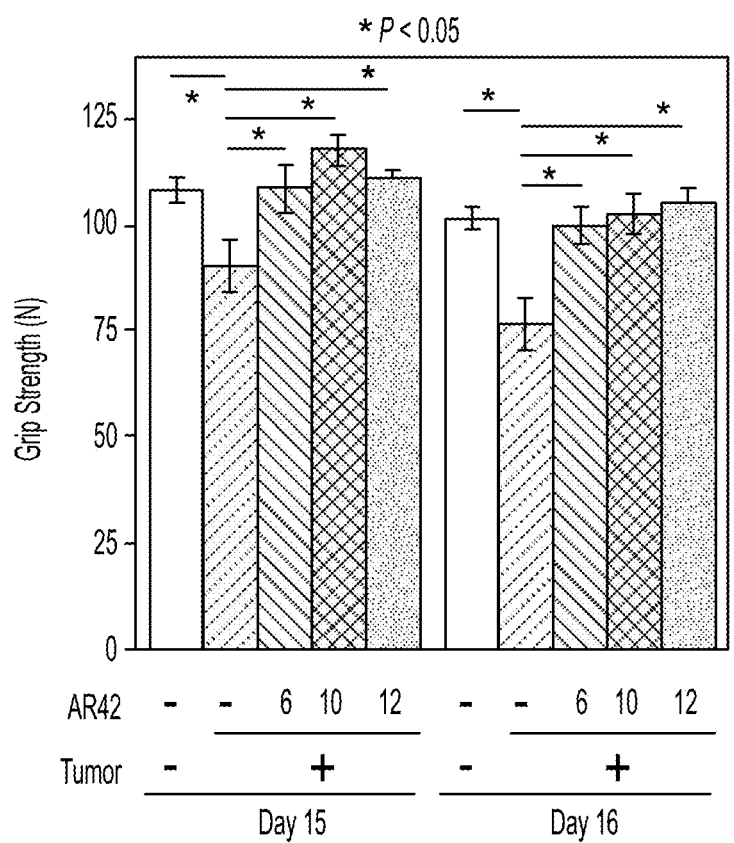
Figure 7:
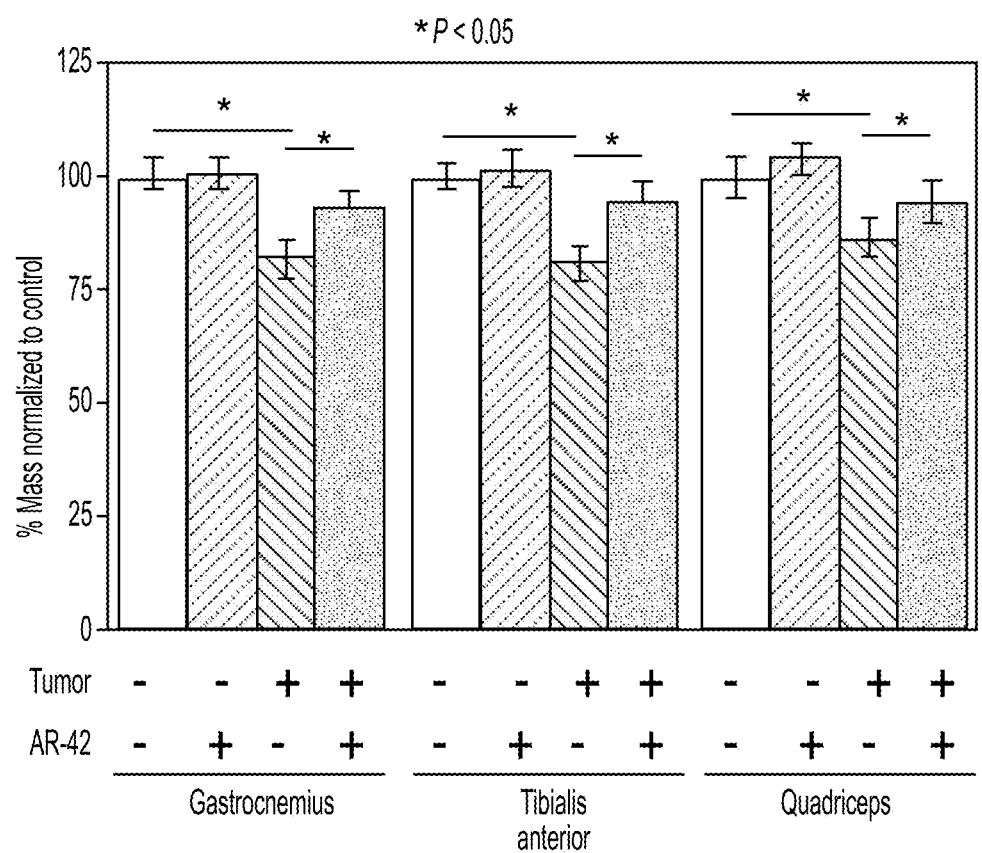

FIG. 2A shows exemplary preservation of muscle fiber size in C-26 tumor bearing mice depicting on the left, photomicrographs of H&E-stained sections of gastrocnemius muscles from tumor-free control mice and tumor-bearing mice treated with vehicle or AR-42. Scale bars, 100 m and on the right, the cross-sectional areas of muscle fibers in gastrocnemius muscles represented as a frequency histogram with a significance of (P<0.001). Data are presented as means±S.D.;

FIG. 2B shows exemplary Kaplan-Meier survival curves for tumor-bearing mice treated with vehicle, vorinostat (50 mg/kg, p.o., daily), romidepsin (0.6 mg/kg, i.p., twice weekly), or AR-42 (50 mg/kg, p.o., every other day). Survival was defined as the time at which loss of body weight (tumor excluded) reached 20% of starting body weight, which served as a humane endpoint for removal from the study (*, P<0.001, vehicle vs. AR-42; n=8);

FIG. 2C shows exemplary photographs of representative mice from each group depicting the therapeutic effect of AR-42 versus vorinostat and romidepsin on cancer cachexia in tumor-bearing mice, as manifested by posture, haircoat and body condition;

FIG. 2D shows exemplary relative mRNA expression levels of Atrogin-1//MAFbx and MuRF1 in the skeletal muscles of vehicle-treated tumor-free mice (n=6) and tumor-bearing mice treated with AR-42 (n=8), vorinostat (n=8), or romidepsin (n=5) compared to that of vehicle-treated tumor-bearing mice (n=8) at 15 days after tumor cell injection. Data are presented as means±S.D. P values: a, <0.001; b, 0.016; c, 0.0063;

FIG. 3A shows exemplary effects of on the levels of intermediates associated with glycolysis and alternative pathways of glucose metabolism;

FIG. 3B shows exemplary effects of AR-42 on glycogen metabolism in gastrocnemius muscles from tumor-free and tumor-bearing mice (n=8 for each group). Tumor-bearing mice were treated with vehicle or AR-42 (50 mg/kg, p.o., every other day) beginning at day 6 post-tumor cell injection and ending at day 17. Tumor-free control mice were treated with vehicle or AR-42 in parallel. Data are presented in box and whisker plots. The bottom and top of the box represent the first and third quartiles, and the "+" symbol and the band inside the box denote the mean and median values, respectively. The ends of the whiskers represent the maximum and minimum values in each group;

FIG. 4 shows that AR-42 blocks cachexia-induced changes in the levels of free amino acids and amino acid metabolites involved in regulating neurotransmission, and biomarkers of insulin resistance in the muscles of C-26 tumor-bearing mice. Samples for analysis were generated from the experiment described with respect to FIGS. 3A and 3B. Data are presented in box-and-whisker plots as described with respect to FIGS. 3A and 3B;

FIG. 5A shows exemplary (upper) effects of AR-42 on the levels of the procachexia cytokines IL-6 (left) and LIF (right) in the sera of tumor-free versus C-26 tumor-bearing mice and (lower) qPCR analysis of the effects of AR-42 on the mRNA expression of IL-6Ra in skeletal muscle of tumor-free versus C-26 tumor-bearing mice. Data are presented as means±S.D. P values: a, <0.001; b, 0.006; c, 0.012 (n=3). Mice were treated as described with respect to FIG. 3;

FIG. 5B shows exemplary principle component analysis of RNA-seq data (left) and Venn diagram (right) showing differentially expressed genes among the four treatment groups. TF, tumor-free; T, tumor-bearing; veh, vehicle-treated; AR, AR-42-treated. Mice were treated as described with respect to FIG. 3;

FIG. 5C shows exemplary analysis of the effects of AR-42 on the transcript levels of six key pro-cachexia drivers by RNA-seq (P values: a, 0.024; b, 0.028; c, 0.015; d, 0.007; e, 0.024; f, 0.026; g, 0.01; h, 0.012; i, <0.001; j, 0.014; n=3). Mice were treated as described with respect to FIG. 3;

FIG. 5D shows exemplary analysis of the effects of AR-42 on the transcript levels of six key pro-cachexia drivers by qPCR in skeletal muscle of mice in the four treatment groups (*, P<0.001; n=6). Data are presented as means±S.D. Mice were treated as described with respect to FIG. 3;

FIG. 6A shows suppression of cancer cachexia in C-26 tumor-bearing mice by delaying treatment with AR-42 until late stages of tumor and cachexia. Changes in body weight (tumor excluded) in the course of 18-day study in vehicle-treated tumor-free control mice (T/F, Veh) and tumor-bearing mice treated with vehicle (T, Veh) versus those treated with oral AR-42 (shown on the left) starting at day 6 (T, AR42/D6), day 10 (T, AR42/D10), or day 12 (T, AR42/D12). P values: a, 0.0015; b, 0.023 (n=8). Arrows indicate the time points for the start of AR-42 treatment. Data are presented as means. For clarity of presentation, the S.D. bars for each data point are not shown. On the right are results showing the lack of suppressive effect of AR-42 on tumor growth in C-26 tumor-bearing mice in the delayed treatment experiment. Data are presented as means±S.D. (n=8);

FIG. 6B shows exemplary photographs depicting the therapeutic effect of AR-42 on cancer cachexia in tumor-bearing mice, despite delayed treatment, as manifested by normal posture, smooth haircoat and better body condition, despite large tumor burdens;

FIG. 6C shows the exemplary effects of AR-42 treatment, initiated at different stages of disease progression as described in FIG. 6A, on the weights of hindlimb muscles, including gastrocnemius, tibialis anterior, and quadriceps, in C-26 tumor-bearing mice. Data are presented as means±S.D. (n=8; *, P<0.001);

FIG. 6D shows the effects of AR-42 on grip strength of tumor-bearing mice relative to the vehicle-treated tumor-free and tumor-bearing controls at day 15 and day 16. Data are presented as means±S.D. (n=8; P values: a, 0.01; b, 0.022; c, <0.001; d, 0.0019). N, Newtons;

FIG. 7 shows that AR-42 protects against cancer-induced muscle wasting in the LLC mouse model of cachexia. Exemplary effects of AR-42 versus vehicle on the mass of hindlimb muscles, including gastrocnemius, tibialis anterior, and quadriceps, in both tumor-free and tumor-bearing mice compared to that of vehicle-treated tumor-bearing mice are shown. Mice were treated in the same manner as described in FIG. 1A, except that mice were sacrificed at day 20 after tumor cell injection. Data are presented as means±S.D. (n=8);

FIG. 8 shows exemplary sequences of primers (SEQ ID NOS 1-16, respectively, in order of appearance) used for real-time RT-PCT;

FIG. 9 shows exemplary Ingenuity Pathway Analysis (IPA)(QIAGEN) of differentially expressed genes (4-fold) related to muscle disease or functions between AR-42-and vehicle-treated C-26 tumor-bearing mice (n=6);

FIG. 10 shows exemplary cytokine profile analysis of serum samples from tumor-free and C-26 tumor-bearing mice treated with vehicle or AR-42 (means±S.D.; n=3 for each group); and FIG. 11 shows exemplary RNA-seq analysis of differentially expressed genes (≥4-fold) in muscles from AR-42-treated versus vehicle-treated C-26 tumor bearing mice (n=3). FIG. 11 discloses "DEAD(Asp-Glu-Ala-Asp)" as SEQ ID NO: 17.

DETAILED DESCRIPTION

Before describing several exemplary aspects described herein, it is to be understood that the invention is not limited to the details of construction or process steps set forth in the following description. The aspects described herein are capable of being practiced or being carried out in various ways.

Aspects described herein disclose the effects of oral AR-42 in attenuating cachexia-induced weight loss and skeletal muscle atrophy and prolonging survival in the CD2F$_1$ mouse colon 26 (C-26) tumor model of cancer cachexia. The mouse CD2F$_1$ cachexia model is described, for example, in BMC Cancer. 2010 Jul. 8; 10:363, incorporated by reference herein in its entirety. The observed anti-cachexia effect was associated with the ability of AR-42 to reprogram cell metabolism and to downregulate IL-6 levels in diseased muscle tissues to suppress muscle wasting and other cachexia-related effects independent of AR-42's effects on reducing tumor load.

Aspects described herein disclose the effects of oral AR-42 in attenuating cachexia-induced weight loss, skeletal muscle atrophy, and prolonging survival in the Lewis Lung Carcinoma (LLC) tumor model of cancer cachexia. See, e.g., Expert Opin Drug Discov. Nov. 1, 2009; 4(11): 1145-1155.

HDAC inhibitors described in U.S. Pat. No. 8,318,808 can be used in various methods described herein. These HDAC inhibitors are based on, for example, fatty acids coupled with $Zn^{2+}$-chelating motifs through aromatic Ω-amino acid linkers. In various aspects, the HDAC inhibitors may have the formula:

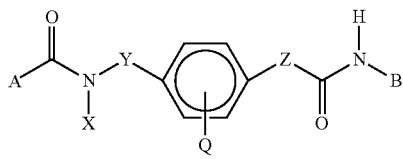

wherein X is chosen from H and CH3; Y is (CH2)n wherein n is 0-2; Z is chosen from (CH2)m wherein m is 0-3 and (CH)2; A is a hydrocarbyl group; B is o-aminophenyl or hydroxyl group; and Q is a halogen, hydrogen, or methyl.

In another aspect, methods described herein utilize AR-42, also known as (S)—N-hydroxy-4-(3-methyl-2-phenylbutanamido)benzamide having the following chemical structure:

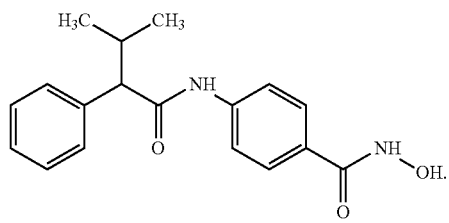 [SMILES: CC(C)C(C(=O)Nc1ccc(C(=O)NO)cc1)c1ccccc1]

In yet another aspect, AR-42 includes salts, solvates, hydrates, anhydrous, co-crystalline and other crystalline forms and combinations. AR-42 can be formulated into a variety of dosage forms having increased stability, increased bioavailability, sustained release, and other properties.

In one aspect, HDAC inhibitors are classified characterized as being zinc dependent or nicotinamide adenine dinucleotide (NAD) dependent (Discov Med 10(54):462-470, November 2010) and are placed into four classes with eighteen family subtypes based on its HDAC substrate: class I (HDACs 1, 2, 3, and 8); class II (HDACs 4, 5, 6, 7, 9, and 10; class III (sirtuins 1-7 (SIRT)); and class IV (HDAC 11). Id. In another aspect, HDAC inhibitors include, but are not limited to, Vorinostat (SAHA) (class I and II inhibitor), Depsipeptide class I inhibitor, and AR-42 (class I and IIb inhibitor). See, e.g., Strahl, B. D. and Allis, C. D. (2000) Nature 403:41-45. Other HDAC inhibitors (e.g., Trichostatin A or TSA) inhibit class 1 and class 2 HDACs. The substrates for HDAC inhibitors vary among the classes and subtypes.

In another aspect, the HDAC inhibitor inhibits class 1 and class 2b HDACs. In yet another aspect, the HDAC inhibitor is AR-42.

In the colon 26 (C-26) tumor model of cancer cachexia, a fragment of the C26 tumor is grafted in isogenic BALB/c mice and the mice develop an undifferentiated carcinoma. Skeletal muscle atrophy (measured by muscle force and resistance to fatigue) correlated with the observed biochemical changes and the model was described as a "well standardized experimental model for research on cancer cachexia." BMC Cancer. 2010 Jul. 8; 10:363.

In one aspect, methods of suppressing cachexia in a mammal with cancer by administering an HDAC class 1 and 2b inhibitor to the mammal in an amount effective to substantially maintain the mammal's weight compared to a mammal that does not receive the HDAC class 1 and 2b inhibitor are provided. In another aspect, the HDAC inhibitor is AR-42.

In yet another aspect, the mammal's weight is not reduced by more than about 6% after about the first 15 days following treatment with AR-42.

In another aspect, the cancer is selected from the group consisting of pancreatic, colon, head, neck, gastric, and esophageal. In another aspect, the mammal is a human.

AR-42 can be administered in an amount of about 1 mg/kg to about 100 mg/kg of the mammal and administered at least once a day. In another aspect, AR-42 is administered twice a day in an amount of about 50 mg/kg of the mammal's weight.

In yet another aspect, levels of IL-6 are reduced by about 56% compared to a mammal that does not receive AR-42. In another aspect, levels of leukemia inhibitory factor (LIF) are reduced by about 88% compared to a mammal that does not receive AR-42. In another aspect, expression of Atrogin-1 mRNA is restored to basal levels compared to a mammal that does not receive AR-42.

In one aspect, expression of MuRF1 mRNA is restored to basal levels compared to a mammal that does not receive AR-42. In another aspect, cachexia-induced increase in IL-6Rα mRNA levels is reduced by about 85% compared to a mammal that does not receive AR-42.

In yet another aspect, cachexia-induced loss of adipose tissue is substantially restored compared to a mammal that does not receive AR-42. In another aspect, cachexia-induced reduction in skeletal muscle fiber size is restored by AR-42 compared to a mammal that does not receive AR-42.

Methods of maintaining skeletal muscle weight in a mammal having cancer comprising administering a HDAC class 1 and 2b inhibitor to said mammal in an amount effective to maintain at least about 90% of said mammal's skeletal muscle weight over a period of time of at least fifteen days compared to a mammal that does not receive the HDAC class 1 and 2b inhibitor are also provided.

In another aspect, methods of prolonging survival of a mammal having cancer comprising administering a HDAC class 1 and 2b inhibitor to the mammal in an amount effective to substantially prolong survival of the mammal compared to a mammal that does not receive the HDAC class 1 and 2b inhibitor are provided. In yet another aspect, the mammal survives at least about 21 days after the administering of AR-42 to the mammal.

In another aspect, administration of AR-42 attenuated cachexia-induced weight loss and skeletal muscle atrophy and prolonged survival in mammals. Without being bound by theory, it is thought that the anti-cachexia effect is associated with the ability of AR-42 to reprogram cell metabolism and to downregulate IL-6 levels in diseased muscle tissues to suppress muscle wasting and other cachexia-related effects independent of AR-42's effects on reducing tumor load.

In one aspect, the anti-cachexia effects of AR-42 were measured by variety of techniques including qRT-PCT analysis of the expression of established mediators of muscle atrophy in cancer (e.g., Cancer Cell. 2008 Nov. 4; 14(5):369-81), measurement of the levels of anti-inflammatory cytokines in serum and gastrocnemius muscle tissues (Am J Pathol. 2011 March; 178(3):1059-68), metaolomic profiling analysis (J Cachexia Sarcopenia Muscle. 2013 June; 4(2):145-55), measuring the levels of free amino acids in muscle tissue (J Cachexia Sarcopenia Muscle. 2013 June; 4(2):145-55; Am J Physiol Endocrinol Metab. 2007 February; 292(2): E501-12), measuring the "glycolytic signature" of cachectic muscle by measuring levels of biochemical associated with the glycolysis pathway (Cachexia Sarcopenia Muscle. 2013 June; 4(2):145-55), measuring the level of glycogen storage in cachectic muscle tissue (Cell Death Differ. 2012 October; 19(10):1698-708), analyzing branched-chain amino acid metabolism in cachectic muscle (Int J Biochem Cell Biol. 2013 October; 45(10):2163-72), and measuring levels of 2-hydroxybutyrate and ophthalmate in cachectic muscle (PLoS One. 2010 May 28; 5(5): e10883; Int J Cancer. 2010 Feb. 1; 126(3):756-63).

HDAC inhibitors, as described herein, can be administered to patient in need of treatment (e.g., a patient having cancer and exhibiting symptoms of cachexia). In one aspect, certain cancers are particularly associated with cachexia including, but not limited to pancreatic, gastric, head, neck, and esophageal ("cachexia-associated cancers"). In another aspect, a class 1, 2b HDAC inhibitor (e.g., AR-42) is administered to a patient in need of treatment.

As used herein, the term "substantially" refers to "most of," a "majority of," or at least 50%, 60%, 70%, 80%, and 90% of the weight or amount of, for example, of a mammal that does not have cancer.

The terms "treat," "reduce," "suppress," "inhibit," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial.

The terms "treatment" or "prevention" also refer to delaying onset of a disease for a period of time or delaying onset indefinitely. The term "treatment" or "treating" refers to administering a drug or treatment to a patient or prescribing a drug to a patient (e.g., by a doctor, nurse, or other medical professional) where the patient or a third party (e.g., caretaker, family member, or health care professional) administers the drug or treatment. The term "amount effective" refers to an amount of a drug or treatment (e.g., an HDAC class I and IIb inhibitor) that will treat, reduce, suppress, inhibit, prevent disease(s) or condition(s) (e.g., cachexia) or prolong survival of a mammal with a disease or condition.

The term "prolong" or "prolonging" as used herein, refers to increasing time of survival of a mammal receiving treatment compared to a mammal that does not receive treatment. In this aspect, "prolonged survival" can refer to increasing the lifespan of the mammal by, for example, 1%, 5%, 10%, 20%, 30%, 40%, 50%, 60%, 70%, 80% or 90% of the lifespan of mammal that does not have cancer.

Any of the HDAC inhibitors described herein can be administered orally, parenterally (IV, IM, depot-IM, SQ, and depot-SQ), sublingually, intranasally (inhalation), intrathecally, topically, or rectally. Dosage forms known to those of skill in the art are suitable for delivery of the HDAC inhibitors described herein.

In one aspect, exemplary HDAC inhibitors are administered in an oral dosage form (e.g., pill, capsule, caplet, or tablet, etc.) to a patient diagnosed with a cancer associated with cachexia (e.g., pancreatic, bladder, gastric, head and neck).

HDAC inhibitors can be formulated into suitable pharmaceutical preparations such as tablets, capsules, or elixirs for oral administration or in sterile solutions or suspensions for parenteral administration. HDAC inhibitors described herein can be formulated into pharmaceutical compositions using techniques and procedures well known in the art.

In one aspect, about 0.1 to 1000 mg, about 5 to about 100 mg, or about 10 to about 50 mg of the HDAC inhibitor (e.g., AR-42), or a physiologically acceptable salt or ester can be compounded with a physiologically acceptable vehicle, carrier, excipient, binder, preservative, stabilizer, flavor, etc., in a unit dosage form as called for by accepted pharmaceutical practice. The amount of active substance in compositions or preparations comprising the HDAC inhibitors is such that a suitable dosage in the range indicated is obtained.

In another aspect, the compositions can be formulated in a unit dosage form, each dosage containing from about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In one aspect, one or more of the HDAC inhibitors are mixed with a suitable pharmaceutically acceptable carrier to form compositions. Upon mixing or addition of the compound(s), the resulting mixture may be a solution, suspension, emulsion, or the like. Liposomal suspensions or any other nanoparticle delivery system may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

In yet another aspect, AR-42 suppresses muscle wasting in cachexia as shown in the C-26 and LLC tumor models of cachexia. The pro-inflammatory cytokines, IL-6 and TNF, represent major pro-cachectic factors in the two models (31, 32). Cytokine profile analysis indicated that, while AR-42 had no effect on serum TNF levels in C-26 tumor-bearing mice, it reduced levels of serum IL-6 and intramuscular IL-6Ra mRNA expression. Nonetheless, these AR-42-treated C-26 tumor-bearing mice still exhibited elevated serum IL-6 levels and IL-6Rα mRNA compared to tumor-free mice, suggesting that decreased IL-6 signaling is not solely responsible for AR-42-mediated suppression of muscle wasting.

Mechanistically, the anti-cachectic effect of AR-42 is unique as the HDAC inhibitors valproic acid and trichostatin-A could not reverse muscle loss in C-26 tumor-bearing mice despite their ability to modulate the myostatin/follistatin axis (33). Similarly, our findings show that, unlike AR-42, vorinostat and romidepsin were ineffective in attenuating cachexia-induced weight loss in the C-26 model. This discrepancy was attributable to the greater ability of AR-42 to suppress the mRNA expression of the E3 ligases Atrogin-1 and MuRF1 in the muscles of tumor-bearing mice, which may reflect differences in their respective abilities to modulate global gene expression in skeletal muscles. Recent evidence suggests a mechanistic link between aberrant acetylation/expression of transcription factors and muscle wasting in diseased muscles, leading to dysregulated expression of cachexia-associated genes [review: (34)]. It was reported that the histone acetyltransferase activity of p300/CBP differentially regulates transcriptional activity and nuclear localization of Foxo family transcription factors in skeletal muscles (35), and that class I HDACs, especially HDAC1, play a crucial role in mediating nutrient deprivation- or muscle disuse-induced muscle atrophy by regulating expression of Foxo and its targets Atrogin-1 and MuRF1 (22).

RNA-seq analysis revealed the ability of AR-42 to reverse tumor-induced shift in gene expression. A total of 677 genes were identified that were differentially expressed by 4-fold or greater between AR-42- and vehicle-treated tumor-bearing mice. Conceivably, this large number of differentially expressed genes might arise from the effect of AR-42 on the transcriptional activity and/or expression of multiple transcription factors/regulators. In addition to Foxo1, AR-42 also modulated the expression of many other transcription factors/regulators, including C/EBPδ, Fos, Jun-b, DAXX, ERN1, HIF3a, MAFF, MAFK, and Mef2c (FIG. 11). Among these transcription factors, the importance of Mef2c in the development of skeletal, cardiac, and smooth muscle is well documented (36), and the AP-1 signaling cascade has been implicated in cancer-associated muscle wasting (37).

It has been proposed that cachectic muscles in C-26 tumor-bearing mice exhibit tumor Warburg physiology, characterized by a high rate of glycolysis (38). Our metabolomic data reveals a pronounced reprogramming of skeletal muscle metabolism in C-26 tumor-bearing mice, which was completely reversed by AR-42. Moreover, the suppressive effect of AR-42 on the production of 2-hydroxybutyrate and opthalmate, biomarkers for insulin resistance (17) and oxidative stress (18), is noteworthy, as substantial evidence has associated insulin resistance (39, 40) and oxidative stress (41) with cachexia.

Mechanistically, the ability of AR-42 to maintain the integrity of skeletal muscles in tumor-bearing mice arises from its diverse, cumulative effects on tumor-induced changes in multiple transcriptional programs and metabolic phenotype. It is of therapeutic significance that oral administration of AR-42 at a late stage of tumor growth was still effective in slowing down the progression of muscle wasting in C-26 tumor-bearing mice. Together, these findings show that HDAC inhibitors (e.g., AR-42) can be used as part of a comprehensive therapeutic strategy for cancer cachexia, as described herein.

Pharmaceutical carriers or vehicles suitable for administration of the HDAC inhibitors described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if the HDAC inhibitors exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, the HDAC inhibitors described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, the HDAC inhibitors and compositions described herein can be enclosed in multiple or single dose containers. The enclosed compounds and compositions can be provided in kits, for example, including component parts that can be assembled for use. For example, AR-42 in lyophilized form and a suitable diluent may be provided as separated components for combination prior to use. A kit may include AR-42 and a second therapeutic agent for co-administration. AR-42 and a second therapeutic agent may be provided as separate component parts. A kit may include a plurality of containers, each container holding one or more unit dose of the compounds described herein. In one aspect, the containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of the exemplary HDAC inhibitor in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The HDAC inhibitors can be used, for example, in combination with an antitumor agent, a hormone, a steroid, or a retinoid. The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents include those agents which promote depolarization of tubulin. Examples include colchicine and vinca alkaloids, including vinblastine and vincristine.

In another aspect, the HDAC inhibitors described herein can be co-administered or administered before or after immunization of a patient with a vaccine to enhance the immune response to the vaccine. In one aspect the vaccine is a DNA vaccine, for example, and HPV vaccine.

In one aspect, solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions, or any other nanoparticle delivery system, including tissue-targeted liposomes may also be suitable as pharmaceutically acceptable carriers. These may be prepared according to methods known in the art.

In another aspect, the HDAC inhibitors may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The oral dosage forms can be administered to the patient 1, 2, 3, or 4 times daily. The HDAC inhibitors described herein can be administered either three or fewer times, or even once or twice daily. Hence, the HDAC inhibitor compounds employed in the methods of the disclosure be administered in oral dosage form. Whatever oral dosage form is used, they can be designed so as to protect the compounds employed in the methods described herein from the acidic environment of the stomach. Enteric coated tablets are well known to those skilled in the art. In addition, capsules filled with small spheres each coated to protect from the acidic stomach, are also well known to those skilled in the art.

The terms "therapeutically effective amount" and "therapeutically effective period of time" are used to denote treatments at dosages and for periods of time effective to reduce neoplastic cell growth. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.1 µM to about 100 mM. For localized administration, much lower concentrations than this can be effective, and much higher concentrations may be tolerated. One of skill in the art will appreciate that such therapeutic effect resulting in a lower effective concentration of an HDAC inhibitor or AR-42 may vary considerably depending on the tissue, organ, or the particular animal or patient to be treated. It is also understood that while a patient may be started at one dose, that dose may be varied overtime as the patient's condition changes.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians who are skilled in this art.

EXAMPLES

The following non-limiting examples illustrate aspects described herein.

Example 1

Cancer Cachexia Models
C-26 Model

In one aspect, tumors were established by subcutaneous injection of C-26 cells (0.5×106 cells in 0.1 ml) into the right flank of male CD2F1 mice (approximately 6 weeks of age; Harlan Laboratories, Indianapolis, Ind.)(11). Tumor-bearing mice, as well as tumor-free mice serving as non-cachectic controls, were randomized into groups that were treated with either AR-42 (50 mg/kg, p.o. by gavage, every other day; Arno Therapeutics, Inc., Flemington, N.J.) or vehicle (0.5% methylcellulose (w/v) and 0.1% Tween-80 (v/v) in sterile water) starting 6 days after cell injection. To investigate the effect of delayed treatment, treatments with drug and/or vehicle were started 6, 10 and 12 days after cancer cell injection.

In another aspect, the effects of AR-42 were compared to other HDAC inhibitors. In this aspect, additional groups of C-26 tumor-bearing mice were treated with vorinostat (50 mg/kg, p.o., once daily) and romidepsin (0.6 mg/kg; i.p., twice weekly) (ChemieTek (Indianapolis, Ind.)).

LLC Model

In another aspect, subcutaneous tumors were established in male C57BL/6 mice (approximately 6 weeks of age; Harlan) by injection of 0.5×106 LLC cells into the right flank. Treatment with AR-42 and vehicle was performed as for the C-26 model beginning 6 days after cell injection. In both models, body weights and food consumption were monitored daily and tumor size was measured no less than every two days. Mice were fasted for 2 hours prior to sacrifice, at which time, hind limb muscles, heart, spleen, epididymal fat, and blood were collected and the weights of the solid tissues were measured. Muscle samples were frozen in liquid nitrogen-chilled 2-methylbutane and then stored at −80° C. until analysis.

Example 2

Grip Strength Measurement

Forelimb grip strength was measured mice using a Digital Grip Strength Meter (Columbus Instruments, Columbus, Ohio). Five measurements were taken from each mouse, the average of which was designated as the mouse's grip strength.

Morphometric Analysis of Muscle Fiber Size

Ten-µm sections were cut from frozen skeletal muscle samples using a cryostat (Leica) and then stained with H&E. Images were captured using an Olympus BX51 microscope (Olympus America, Inc.) and muscle fiber cross-sectional areas were determined using Olympus CellSens 1.11 software. Measurements were obtained from five different sections of muscle from each of five mice from each group.

RNA Isolation, qRT-PCR, and RNA-seq Analysis

Total RNA was isolated from homogenized gastrocnemius muscles (n=3/group) with TRIzol reagent (Life Technologies, Carlsbad, Calif.) and then purified using the RNAeasy Mini Kit (Qiagen, Valencia, Calif.). qRT-PCR was performed as described previously (42) by using the Bio-Rad CFX96 Real-Time PCR Detection System with iQ SYBR Green Supermix (Bio-Rad, Hercules, Calif.). Primer sequences are listed in FIG. 8. RNA-seq library generation and data analysis were performed at The Ohio State University Comprehensive Cancer Center (OSUCCC) Nucleic Acid Shared Resource.

Metabolomic and Cytokine Profiling

Gastrocnemius muscles and sera were collected at day 17 post-cell injection from each treatment group (n=8/group). Muscle was submitted to Metabolon, Inc. (Durham, N.C.) for metabolomic analysis of 270 metabolic intermediates via proprietary mass spectrometry platforms. Serum was submitted to Eve Technologies (Alberta, Canada) for analysis of 32 cytokines using a mouse cytokine array (32-plex panel).

Statistical Analysis

Data analysis was conducted by using SAS 9.3 software (SAS, Inc; Cary, N.C.). For the experiments with repeated measures, data were analyzed by mixed effect models, incorporating observational dependencies across each subject. For other experiments involving independent groups, data were analyzed by ANOVA. For the time-to-event experiment (FIG. 2B), the difference in survival functions were compared by log-rank tests. Multiplicities were adjusted by Holm's method to control the overall family-wise error rate at 0.05. RNA-seq data were analyzed by using Ingenuity Pathway Analysis (IPA) software (Ingenuity Systems, Redwood City, Calif.). Only genes with >4-fold change and P<0.05 were selected for pathway analysis.

Example 3

AR-42 Suppresses Cancer Cachexia in the C-26 Colon Adenocarcinoma Model

Figure 1A:
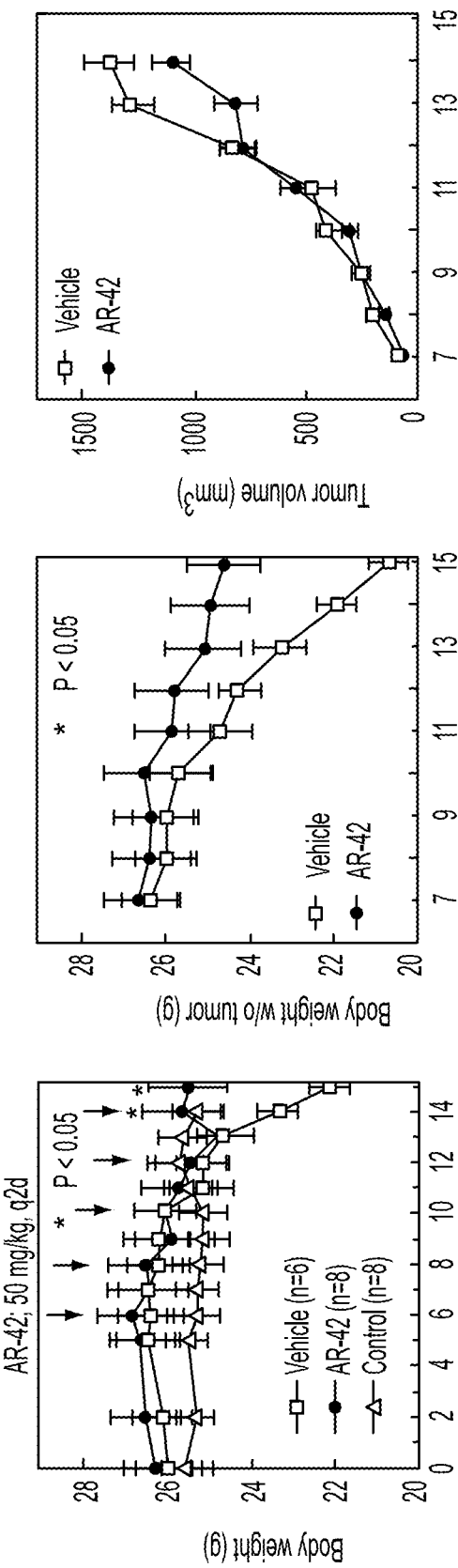
FIG. 1B shows photographs of representative mice with tumor burdens from each group depicting the therapeutic effect of AR-42 on cancer cachexia.
FIG. 1C shows an exemplary average daily diet consumption among the three treatment groups in the course of study. Data are presented as means±S.D. (n=8)
FIG. 1D shows the exemplary effects of AR-42 on the weights of hindlimb muscles, including gastrocnemius, tibialis anterior, and quadriceps (P values: a, <0.001; b, 0.0042; c, 0.0046) in both tumor-free and tumor-bearing mice compared to those of vehicle-treated tumor-bearing and tumor-free mice (n=8)
FIG. 1E shows the exemplary effects of AR-42 on heart, adipose tissue, and spleen (P values: a, <0.001; b, 0.0059; c, 0.001; d, 0.009) in both tumor-free and tumor bearing mice compared to those of vehicle-treated tumor-bearing and tumor-free mice (n=8)
Figure 1B:
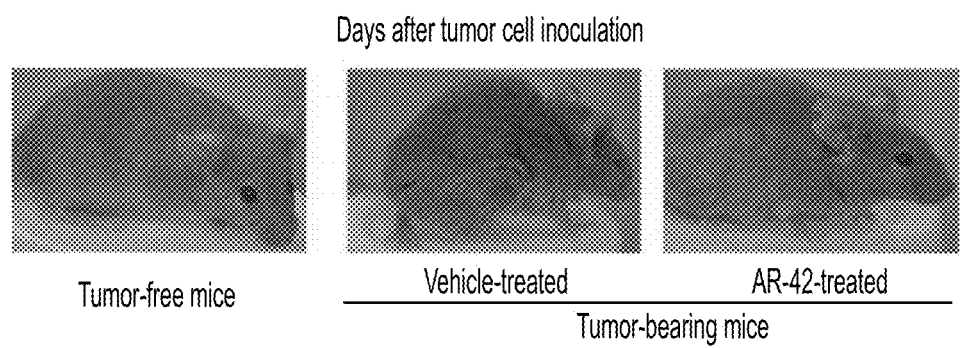
Figure 1C:
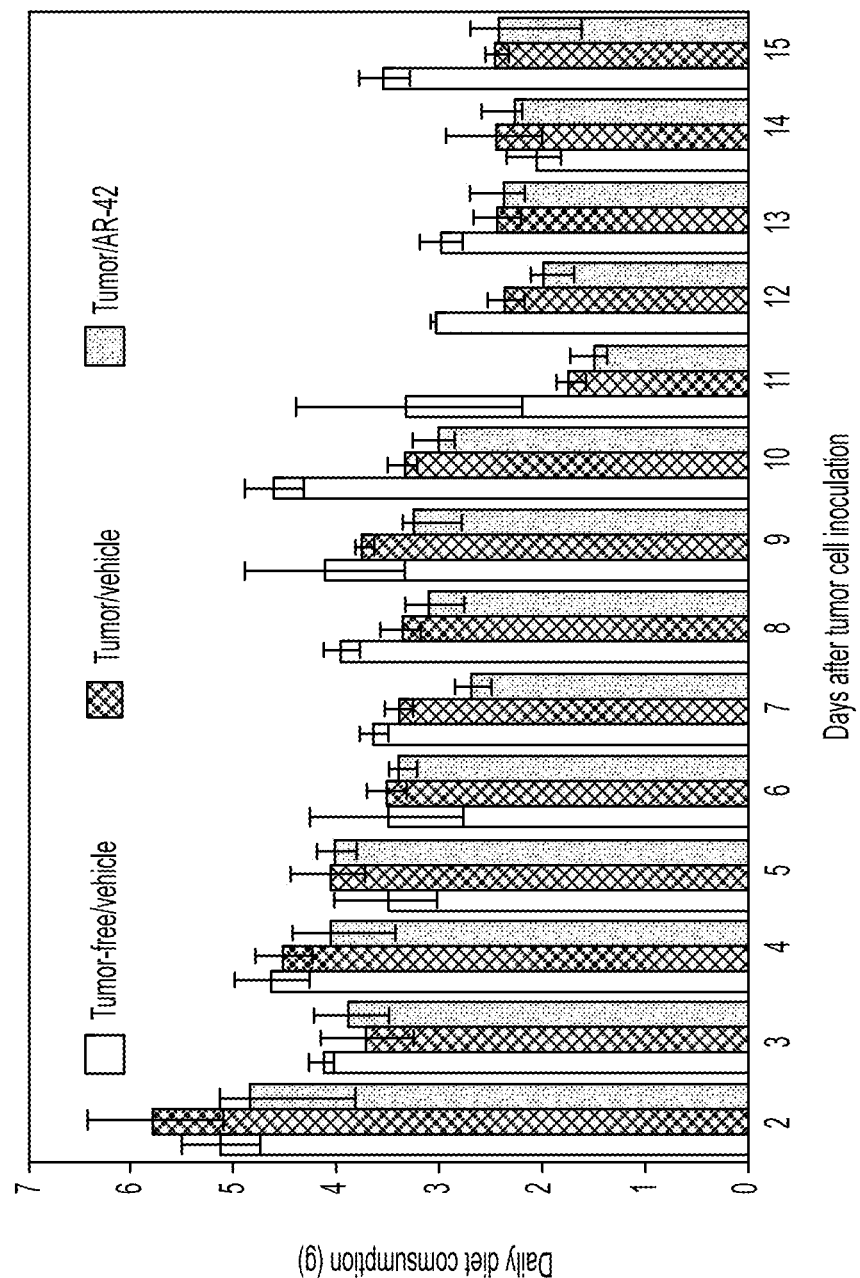

In one aspect, mice were treated orally by gavage with AR-42 (50 mg/kg) or vehicle every other day starting 6 days after injection C-26 cells, when palpable tumors had formed. While the vehicle group showed a large drop in body weight starting at day 12, AR-42-treated mice maintained their weight at levels comparable to that of tumor-free controls (FIG. 1A, left). By the study endpoint (day 15), the magnitude of the weight loss, after deducting the mass of the tumors (1 cm$^3$ volume=1 gram mass), reached >20% for the vehicle-treated group, and 6% for AR-42-treated mice (center). This effect cannot be attributed to decreased tumor burden, since AR-42 did not alter tumor growth relative to vehicle (right), or to increased food intake, since average daily consumption was comparable in the AR-42-treated and vehicle-treated groups, and less than that in tumor-free mice (FIG. 1C). The AR-42-treated mice, despite their large tumor burden, were alert, responsive, active, and lacked the hunched posture and rough haircoat observed in vehicle-treated counterparts by the end point of this study (FIG. 1B).

Example 4

AR-42 Protects Muscle Against Cachexia-Induced Atrophy

Figure 1D:
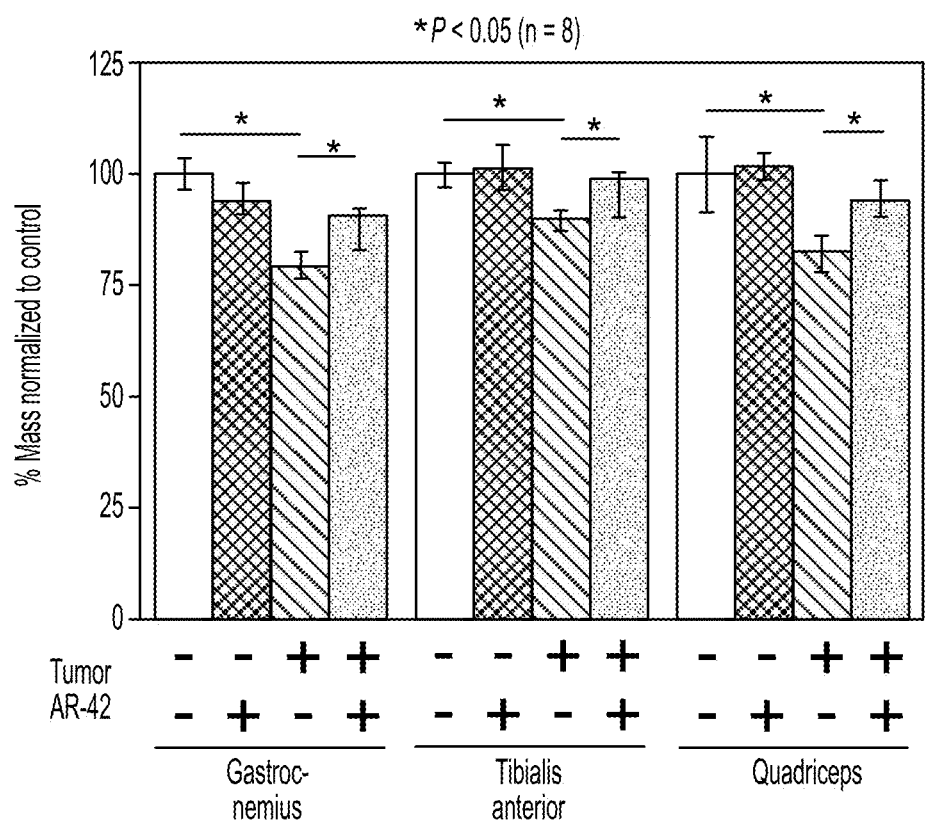

Consistent with the preservation of body weight, skeletal muscle mass was preserved in AR-42-treated tumor-bearing mice. Indicative of cachexia, the weights of gastrocnemius, tibialis anterior and quadriceps from vehicle-treated tumor-bearing (tumor-bearing/vehicle) mice were reduced by 20.6%, 10.5%, and 18.1%, respectively, relative to corresponding muscles from tumor-free control mice, while those in AR-42-treated tumor-bearing (tumor-bearing/AR-42) mice were reduced by 9.6%, 0.8%, and 5.8%, respectively (FIG. 1D).

Figure 1E:
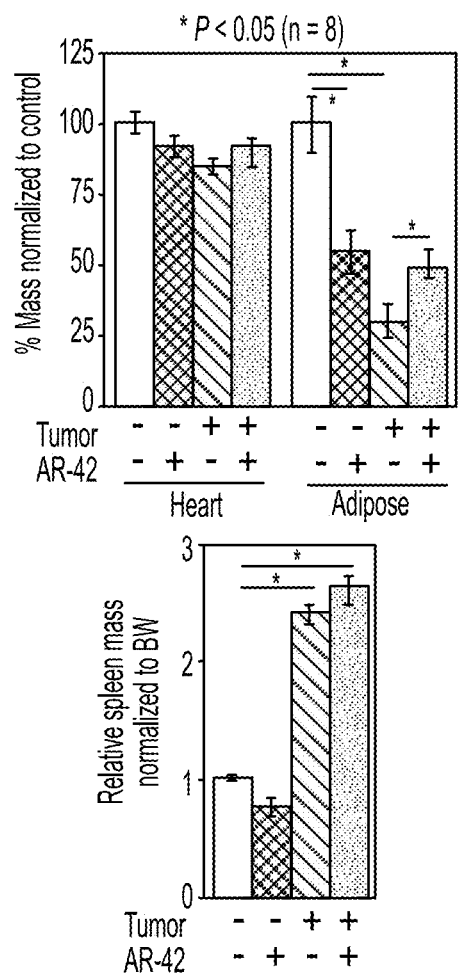

Tumor-bearing/vehicle mice exhibited other hallmarks of cachexia, including significant losses of cardiac and, particularly, adipose tissue mass (29.3±6.0% of tumor-free control), which were ameliorated by AR-42 treatment (FIG. 1E, upper). Interestingly, AR-42 significantly reduced the mass of adipose tissue by approximately 50% in tumor-free mice yet restored the loss of adipose tissue mass in tumor-bearing mice to a level comparable to that of tumor-free/AR-42 mice, a dichotomous effect suggesting its ability to maintain lipid homeostasis.

In another aspect, C-26 tumor-bearing mice exhibited grossly enlarged spleens relative to tumor-free control mice (11), which were not improved by AR-42 (FIG. 1E, lower). As splenomegaly in C-26 tumor-bearing mice results from expansion of myeloid-derived suppressor cells and other immune cells in the spleen (12), this finding suggests AR-42 was acting predominantly on the muscle rather than through an immunologic mechanism.

The protective effect of AR-42 against muscle wasting was manifested by the abrogation of cachexia-induced reduction in skeletal muscle fiber size. Tumor-bearing/vehicle mice exhibited a 48.2% decrease relative to the tumor-free control in mean cross-sectional area of muscle fibers at day 15 (1297.6±638.8 versus 2503.5±917.5 µm$^2$), which was restored by AR-42 (2146.3±923.4 µm$^2$)(FIG. 2A, left). The prominent shift in fiber size distribution to smaller cross-sectional area in cachectic muscles of tumor-bearing/vehicle mice was reversed by AR-42 (FIG. 2A, right)

AR-42 Prolongs the Survival of C-26 Tumor-Bearing Mice

The effects of AR-42 were compared to other HDAC inhibitors (i.e., vorinostat and romidepsin) in C-26 tumor-bearing mice. Starting on day 6 after tumor cell injection, mice were treated continuously with AR-42 (50 mg/kg every other day, orally), vorinostat [50 mg/kg once daily, orally (13)], romidepsin [0.6 mg/kg twice weekly, i.p. (14)], or vehicle, until weight loss, as determined by daily body weight measurements and subtraction of tumor mass, reached 20% of starting weight. As shown, oral AR-42 was effective in protecting these mice from tumor-associated wasting, with 100% cumulative survival at day 21 when tumor volume reached the threshold for euthanasia (FIG. 2B). In contrast, vorinostat and romidepsin showed limited or no appreciable protective effects on body weight. Moreover, tumor-bearing/AR-42 mice were alert, responsive, active, and appeared healthy at 21 days after tumor cell injection, in contrast to vehicle—(Day 15), romidepsin—(Day 16), and vorinostat-treated mice (Day 18)(FIG. 2C).

Example 3

Differential Effects on the Regulation of Skeletal Muscle Protein Turnover

Skeletal muscle mass is regulated by a balance between protein synthesis and degradation. Without being bound by theory, it is believed that the differential anti-cachectic effect of AR-42 versus vorinostat and romidepsin may be attributable to differences in their ability to regulate pathways governing protein turnover. This was supported by the suppressive effect of AR-42 on the mRNA expression of Atrogin-1/MAFbx and, MuRF1, two E3 ligases involved in ubiquitin-mediated skeletal muscle protein degradation (15, 16) (FIG. 2D).

qPCR analysis of gastrocnemius muscles revealed a significant increase in Atrogin-1 and MuRF1 mRNA levels (29.4±3.5-fold and 25.8±3.9-fold, respectively) in cachectic muscle (tumor-bearing/vehicle; n=8) relative to the tumor-free/vehicle control (n=6). AR-42 was able to restore expression of Atrogin-1 (2.7±0.7-fold) and MuRF1 (1.1±0.2-fold) mRNA to basal levels (n=8). Vorinostat (n=8) and romidepsin (n=5) also significantly reduced the mRNA expression of these two E3 ligases in cachectic muscles, but to a lesser extent than AR-42 (Atrogin-1/MuRF1: vorinostat, 9.6±1.8/5.5±1.1-fold; romidepsin, 19.6±3.1/14.6±3.3-fold)(FIG. 2D).

To confirm that the anti-cachectic activity of AR-42 was not specific to the C-26 model, it was also evaluated in the LLC model. C57BL/6 mice bearing subcutaneous LLC tumors were treated with AR-42 (50 mg/kg, p.o., every other day) starting on day 6 after tumor cell injection, and continuing until day 20 when hind limb muscles were harvested at sacrifice. As shown in FIG. 7, AR-42 protected LLC tumor-bearing C57Bl/6 mice from loss of muscle mass (gastrocnemius: vehicle, 81.7±3.7% of non-cachectic control; AR-42, 92.2±3.5%; tibialis anterior: vehicle, 80.3±4.0%; AR-42, 93.4±3.9%; quadriceps: vehicle, 84.4±4.6%; AR-42, 93.4±4.8%; all P values <0.05, n=8).

Example 4

AR-42 Maintains Metabolic Integrity of Muscle in Tumor-Bearing Mice

With cachexia, skeletal muscles undergo complex metabolic changes in response to tumor/host-derived inflammatory and neuroendocrine stressors (1). Accordingly, we conducted metabolic profiling analysis to investigate the effect of AR-42 on cachexia-induced shifts in metabolic phenotype in skeletal muscle. Tumor-free and C-26 tumor-bearing mice were treated with vehicle or AR-42 as aforementioned, and gastrocnemius muscles were collected at day 17 for metabolomic analysis. Comparison of muscle biochemical profiles among the four groups (n=8/group) revealed the ability of AR-42 to restore cachexia-induced metabolic changes in skeletal muscles, which are summarized as follows.

Glycolysis. Cachectic muscles from tumor-bearing/vehicle mice showed significantly lower levels of glucose and key glycolytic intermediates than tumor-free controls (FIG. 3A). AR-42 reversed these metabolic changes, restoring the intramuscular levels of glucose and intermediates to or, in some cases, above baseline levels detected in tumor-free/vehicle mice. Moreover, elevated glucose was shunted into sorbitol-fructose biosynthesis and pentose phosphate pathways, leading to increased production of sorbitol, fructose, and ribose, a metabolite derived from the pentose phosphate pathway.

Glycogen stores. Muscle from tumor-bearing/vehicle mice showed significant decreases in short-chain malto-oligosaccharides and glucose 1-phosphate (FIG. 3B), suggesting the depletion of glycogen stores in cachectic muscles. AR-42 treatment significantly replenished these glycogen metabolic intermediates.

Free amino acids. Consistent with the increased protein degradation that characterizes muscle wasting, a large number of free amino acids were significantly elevated in cachectic muscles from tumor-bearing/vehicle mice relative to that in tumor-free/vehicle mice (FIG. 4), indicative of a cachectic phenotype. Similarly, several amino acid derivatives/metabolites that function as neurotransmitters, including kynurenin, N-acetyl-aspartyl-glutamate, and y-aminobutyrate, were elevated. In contrast, alanine, which is released from muscles to support liver gluconeogenesis, was reduced in cachectic muscles. This cachectic phenotype was reversed by AR-42 treatment, indicating its ability to block muscle protein degradation.

Organic acids. The amino acid metabolites 2-hydroxybutyrate and ophthalmate are biomarkers for insulin resistance (17) and oxidative stress (18), respectively. The increase in these two organic acids in muscles of tumor-bearing/vehicle mice (FIG. 4) suggests that cachexia promotes insulin resistance and oxidative stress, which, in turn, exacerbates muscle wasting. AR-42 dramatically reduced the two biomarkers to levels comparable to those measured in tumor-free mice.

Example 5

AR-42 Suppresses Cancer Cachexia by Targeting Multiple Pro-Cachexia Drivers

To shed light onto the mechanism by which AR-42 mediated its anti-cachectic effect, sera and gastrocnemius muscle from vehicle- or AR-42-treated tumor-free and C-26 tumor-bearing mice were used for cytokine profiling analysis and whole transcriptome shotgun sequencing (RNA-seq), respectively.

Cytokine profiles. Of 32 cytokines examined (FIG. 10), IL-6 and leukemia inhibitory factor (LIF), two well-recognized cachexia drivers (19), were significantly increased in the sera of tumor-bearing/vehicle mice relative to that of tumor-free/vehicle mice (IL-6; 230±105 versus 2.9±1.3 pg/ml; LIF, 19.7±9.3 versus 1.7±1.5 pg/ml) (FIG. 5A, upper), while no significant differences were noted with other cytokines. AR-42 reduced IL-6 and LIF levels by 56% and 88%, respectively, in tumor-bearing mice (IL-6, 102±38 pg/ml; LIF, 3.8±1.6 pg/ml) compared to the vehicle-treated counterparts. In light of the ability of AR-42 to blunt cachexia-associated increases in IL-6, we examined the effect of AR-42 on intramuscular mRNA levels of IL-6 receptor alpha chain (IL-6Rα). IL-6Rα mRNA was significantly elevated (13±1.4-fold) in muscle of tumor-bearing/vehicle mice (n=9) compared to that of tumor-free mice (n=6). AR-42 reduced this cachexia-induced increase by 85% (2.0±0.2-fold; n=10)(FIG. 5, lower). These findings suggest that AR-42 inhibits muscle wasting, in part, by blocking IL-6 signaling.

RNA-seq analysis. Principal component analysis of the RNA-seq data revealed a pronounced effect of the C-26 tumor on the global gene expression pattern in the muscle of tumor-bearing/vehicle mice relative to tumor-free/vehicle counterparts (FIG. 5B, left). While AR-42 had no appreciable effect on the pattern of gene expression in the non-cachectic muscle of tumor-free mice, it reversed the tumor-induced shift in gene expression in cachectic muscle to a state close to that in tumor-free mice. Pursuant to this, we conducted pairwise analysis of differentially expressed genes between tumor-bearing/vehicle mice and the other three treatment groups, the results of which are represented in a Venn diagram (FIG. 5B, right). The largely overlapping areas among paired analyses suggest that AR-42 restores, to a great extent, tumor-induced changes in global gene expression.

Pairwise comparison of gene expression in muscles from vehicle- and AR-42-treated tumor-bearing mice revealed a total of 677 genes with 4-fold or greater differential expression (376 upregulated and 301 downregulated) (FIG. 10). Analysis of these genomic data for their functional and disease associations using Ingenuity Pathway Analysis (IPA) revealed that 66 of these differentially expressed genes were annotated to categories of atrophy, contractility, development, and muscle morphology, and skeletal muscle cell size, muscle cell death, and protein catabolism (FIG. 11).

Of these muscle function- and disease-associated genes, the effects of AR-42 on the following six genes are noteworthy in light of their demonstrated links with cancer-induced cachexia. These include Foxo1 (encoding Forkhead box protein O1) (20-23) and its target genes Trim63 (MuRF1) and Fbxo32 (Atrogin-1) (24, 25), PNPLA2 [adipose triglyceride lipase (ATGL)] (26, 27), UCP3 (uncoupling protein 3) (28, 29), and Mef2c [myogenic transcription factor myocyte enhancer factor] (30) (FIG. 5C). Validation of the RNA-seq data for these six genes by qRT-PCR showed a high correlation between the data sets for the relative mRNA expression levels among the four treatment groups (FIG. 5D).

Example 6

Delayed Treatment with AR-42 Remains Effective in Suppressing Muscle Wasting

The above findings demonstrate the efficacy of oral AR-42 in suppressing cancer-associated muscle wasting by restoring metabolic and gene expression profiles in skeletal muscle. In those experiments, treatment was initiated early in the progression of cachexia when overt signs of wasting were undetectable. To investigate whether later initiation of AR-42 treatment remains protective against cachexia, C-26 tumor-bearing mice were treated with AR-42 (50 mg/kg, p.o., every other day) starting at 6, 10 and 12 days after tumor cell injection.

Consistent with our earlier data (FIG. 1), tumor-bearing/vehicle mice lost 19% of body weight (tumor excluded) by day 17. In contrast, treatment with AR-42 starting at day 6 (D6), 10 (D10), or 12 (D12) limited weight loss to 6%, 11%, and 12%, respectively (n=8)(FIG. 6A, left), without appreciable effects on tumor growth (right). Moreover, AR-42-treated mice exhibited signs better health than their vehicle-treated counterparts (FIG. 6B). This protective effect of AR-42 was reflected in the preservation of gastrocnemius weight and, to a lesser extent, that of tibialis anterior and quadriceps muscles (FIG. 6C). Consistent with the protective effect on muscle mass, handgrip dynamometry indicated that AR-42 helped preserve forelimb muscle strength in all drug-treated groups relative to the vehicle-treated control at day 15 and 16 (FIG. 6D).

Example 7

Tumor-bearing/vehicle mice exhibited other hallmarks of cachexia, including significant losses of cardiac and, particularly, adipose tissue mass (29.3±6.0% of tumor free control), which were ameliorated by AR-42 treatment (FIG. 1E, upper). Interestingly, AR-42 significantly reduced the mass of adipose tissue by approximately 50% in tumor free mice yet restored the loss of adipose tissue mass in tumor-bearing mice to a level comparable to that of tumor-free/AR-42 mice, a dichotomous effect suggesting its ability to maintain lipid homeostasis.

C-26 tumor-bearing mice exhibited grossly enlarged spleens relative to tumor-free control mice (11), which was not improved by AR-42 (FIG. 1E, lower). As splenomegaly in C-26 tumor-bearing mice results from expansion of myeloid-derived suppressor cells and other immune cells in the spleen (12), this finding suggests AR-42 was acting predominantly on the muscle rather than through an immunologic mechanism.

The protective effect of AR-42 against muscle wasting was manifested by the abrogation of cachexia-induced reduction in skeletal muscle fiber size. Tumor-bearing/vehicle mice exhibited a 48.2% decrease relative to the tumor-free control in mean cross-sectional area of muscle fibers at day 15 (1297.6±638.8 versus 2503.5±917.5 $\mu m_2$), which was restored by AR-42 (2146.3±923.4 $\mu m_2$)(FIG. 2A, left). The prominent shift in fiber size distribution to smaller cross-sectional area in cachectic muscles of tumor-bearing/vehicle mice was reversed by AR-42 (FIG. 2A, right).

Example 8

Differential Effects on the Regulation of Skeletal Muscle Protein Turnover

As skeletal muscle mass is regulated by a balance between protein synthesis and degradation, the differential anti-cachectic effect of AR-42 versus vorinostat and romidepsin may be attributable to differences in their ability to regulate pathways governing protein turnover. This was supported by the suppressive effect of AR-42 on the mRNA expression of Atrogin-1/MAFbx and, MuRF1, two E3 ligases involved in ubiquitin-mediated skeletal muscle protein degradation (15, 16) (FIG. 2D). As expected, qPCR analysis of gastrocnemius muscles revealed a significant increase in Atrogin-1 and MuRF1 mRNA levels (29.4±3.5-fold and 25.8±3.9-fold, respectively) in cachectic muscle (tumor-bearing/vehicle; n=8) relative to the tumor-free/vehicle control (n=6). AR-42 was able to restore expression of Atrogin-1 (2.7±0.7-fold) and MuRF1 (1.1±0.2-fold) mRNA to basal levels (n=8). Vorinostat (n=8) and romidepsin (n=5) also significantly reduced the mRNA expression of these two E3 ligases in cachectic muscles, but to a lesser extent than AR-42 (Atrogin-1/MuRF1: vorinostat, 9.6±1.8/5.5±1.1-fold; romidepsin, 19.6±3.1/14.6±3.3-fold) (FIG. 2D).

Example 9

Cells

Cultured C-26 and LLC cells were maintained in fetal bovine serum (FBS)-supplemented (10%) RPMI 1640 medium and DMEM medium (Invitrogen, Carlsbad, Calif.), respectively, at 37° C. in a humidified incubator with 5% $CO_2$. For injection into mice for cancer cachexia models, cells were harvested by trypsinization, pelleted in the FBS-supplemented culture medium, and then resuspended in sterile PBS at a concentration of $5 \times 10^6$ cells/ml.

Mice

CD2F1 and C57BL/6 mice were group-housed under conditions of constant photoperiod (12-hour light/12-hour dark), temperature and humidity with ad libitum access to water and standard diet. Mice were briefly anesthetized (isoflurane, 3-4%) during administration of drugs (AR-42, vorinostat, vehicle) by oral gavage. Food consumption was estimated by weighing food in each cage daily and dividing the daily decrease in food by the number of mice in the cage. Tumor volumes were calculated from caliper measurements using a standard formula (length×width$^2$×π/6).

Grip Strength Measurement

To measure forelimb grip strength, each mouse was held by the base of its tail and lowered over the apparatus until its forepaws grasped the pull bar. The mouse was then gently pulled horizontally in a straight line away from the grip meter until the mouse released the bar, and the maximum force attained was recorded. Five measurements were taken from each mouse, the average of which was designated as the mouse's grip strength.

RNA-seq Library Generation and Data Analysis Pipeline

RNA quality was assessed on an Agilent 2100 Bioanalyzer using a Pico RNA chip and the input total RNA amount was assessed using Agilent Qubit RNA assay. Transcriptome libraries were prepared using the Illumina TruSeq RNA Sample Preparation Kit V2. The resultant libraries were assessed for quantity and quality using Agilent Qubit DNA assay and with PerkinElmer Labchip DNA GX analysis, respectively. All libraries were mixed in equal proportions generating pools of samples that would yield approximately 40 million passed filter reads when sequenced on Illumina HiSeq 2500 sequencer. The raw sequencing data from the Illumina HiSeq CASAVA pipeline were assessed for quality using FastQC, RNASeQC and RSeQC software. Subsequent analyses were as follows: demultiplexed passed filter sequencing reads were aligned to GRCm38/mm10 using TopHat 2 (v2.0.7) RNAseq aligner; CuffLinks 2 (c2.1.1) was used for assembling the aligned reads to UCSC mm10 gene annotation; CuffCompare and CuffMerge was used to compile aligned reads to mm10 genes and merge assembled transcripts into a custom gene annotation; CuffDiff was used to compare differential gene expression associated with each treatment group.

Example 10

To confirm that the anti-cachectic activity of AR-42 was not specific to the C-26 model, it was also evaluated in the LLC model. C57BL/6 mice bearing subcutaneous 11 LLC tumors were treated with AR-42 (50 mg/kg, p.o., every other day) starting on day 6 after tumor cell injection, and continuing until day 20 when hind limb muscles were harvested at sacrifice.

As shown in FIG. 7, AR-42 protects against cancer-induced muscle wasting in the LLC mouse model of cachexia. Effects of AR-42 versus vehicle on the mass of hindlimb muscles, including gastrocnemius, tibialis anterior, and quadriceps, in both tumor-free and tumor-bearing mice compared to that of vehicle-treated tumor-bearing mice. Mice were treated in the same manner as described in FIG. 1A, except that mice were sacrificed at day 20 after tumor cell injection. Data are presented as means±S.D. (n=8); (gastrocnemius: vehicle, 81.7±3.7% of non-cachectic control; AR-42, 92.2±3.5%; tibialis anterior: vehicle, 80.3±4.0%; AR-42, 93.4±3.9%; quadriceps: vehicle, 84.4±4.6%; AR-42, 93.4±4.8%; all P values <0.05, n=8).

REFERENCES

1. Fearon K C, Glass D J, Guttridge D C. Cancer cachexia: mediators, signaling, and metabolic pathways. Cell Metab 2012; 16: 153-66.
2. Tisdale M J. Cachexia in cancer patients. Nat Rev Cancer 2002; 2: 862-71.
3. von Haehling S, Anker S D. Cachexia as a major underestimated and unmet medical need: facts and numbers. J Cachexia Sarcopenia Muscle 2010; 1: 1-5.
4. Tisdale M J. Mechanisms of cancer cachexia. Physiol Rev 2009; 89: 381-410.
5. Lee S J, Glass D J. Treating cancer cachexia to treat cancer. Skelet Muscle 2011; 1: 2.
6. Maccio A, Madeddu C, Mantovani G. Current pharmacotherapy options for cancer anorexia and cachexia. Expert Opin Pharmacother 2012; 13: 2453-72.
7. Kulp S K, Chen C S, Wang D S, Chen C Y, Chen C S. Antitumor effects of a novel phenylbutyrate-based histone deacetylase inhibitor, (S)-HDAC-42, in prostate cancer. Clin Cancer Res 2006; 12: 5199-206.
8. Lu Y S, Kashida Y, Kulp S K, Wang Y C, Wang D, Hung J H, et al. Efficacy of a novel histone deacetylase inhibitor in murine models of hepatocellular carcinoma. Hepatology 2007; 46: 1119-30.
9. Sargeant A M, Rengel R C, Kulp S K, Klein R D, Clinton S K, Wang Y C, et al. OSU-HDAC42, a histone deacetylase inhibitor, blocks prostate tumor progression in the transgenic adenocarcinoma of the mouse prostate model. Cancer Res 2008; 68: 3999-4009.
10. Yang Y T, Balch C, Kulp S K, Mand M R, Nephew K P, Chen C S. A rationally designed histone deacetylase inhibitor with distinct antitumor activity against ovarian cancer. Neoplasia 2009; 11: 552-63, 3 p following 63.
11. Acharyya S, Ladner K J, Nelsen L L, Damrauer J, Reiser P J, Swoap S, et al. Cancer cachexia is regulated by selective targeting of skeletal muscle gene products. J Clin Invest 2004; 114: 370-8.
12. Mundy-Bosse B L, Lesinski G B, Jaime-Ramirez A C, Benninger K, Khan M, Kuppusamy P, et al. Myeloid-derived suppressor cell inhibition of the IFN response in tumor-bearing mice. Cancer Res 2011; 71: 5101-10.
13. Lucas D M, Alinari L, West D A, Davis M E, Edwards R B, Johnson A J, et al. The novel deacetylase inhibitor AR-42 demonstrates pre-clinical activity in B-cell malignancies in vitro and in vivo. PLoS One 2010; 5: e10941.
14. Sasakawa Y, Naoe Y, Inoue T, Sasakawa T, Matsuo M, Manda T, et al. Effects of FK228, a novel histone deacetylase inhibitor, on human lymphoma U-937 cells in vitro and in vivo. Biochem Pharmacol 2002; 64: 1079-90.
15. Bodine S C, Latres E, Baumhueter S, Lai V K, Nunez L, Clarke B A, et al. Identification of ubiquitin ligases required for skeletal muscle atrophy. Science 2001; 294: 1704-8.
16. Lecker S H, Jagoe R T, Gilbert A, Gomes M, Baracos V, Bailey J, et al. Multiple types of skeletal muscle atrophy involve a common program of changes in gene expression. FASEB J 2004; 18: 39-51.
17. Gall W E, Beebe K, Lawton K A, Adam K P, Mitchell M W, Nakhle P J, et al. alpha-hydroxybutyrate is an early biomarker of insulin resistance and glucose intolerance in a nondiabetic population. PLoS One 2010; 5: e10883.
18. Soga T, Baran R, Suematsu M, Ueno Y, Ikeda S, Sakurakawa T, et al. Differential metabolomics reveals ophthalmic acid as an oxidative stress biomarker indicating hepatic glutathione consumption. J Biol Chem 2006; 281: 16768-76.
19. Tisdale M J. Biology of cachexia. J Natl Cancer Inst 1997; 89: 1763-73.
20. Kamei Y, Miura S, Suzuki M, Kai Y, Mizukami J, Taniguchi T, et al. Skeletal muscle FOXO1 (FKHR) transgenic mice have less skeletal muscle mass, down-regulated Type I (slow twitch/red muscle) fiber genes, and impaired glycemic control. J Biol Chem 2004; 279: 41114-23.
21. Reed S A, Sandesara P B, Senf S M, Judge A R. Inhibition of FoxO transcriptional activity prevents muscle fiber atrophy during cachexia and induces hypertrophy. FASEB J 2012; 26: 987-1000.
22. Beharry A W, Sandesara P B, Roberts B M, Ferreira L F, Senf S M, Judge A R. HDAC1 activates FoxO and is both sufficient and required for skeletal muscle atrophy. J Cell Sci 2014; 127: 1441-53.
23. Sandri M, Sandri C, Gilbert A, Skurk C, Calabria E, Picard A, et al. Foxo transcription factors induce the atrophy-related ubiquitin ligase atrogin-1 and cause skeletal muscle atrophy. Cell 2004; 117: 399-412.
24. Gumucio J P, Mendias C L. Atrogin-1, MuRF-1, and sarcopenia. Endocrine 2013; 43: 12-21.
25. Bonaldo P, Sandri M. Cellular and molecular mechanisms of muscle atrophy. Dis Model Mech 2013; 6: 25-39.
26. Das S K, Hoefler G. The role of triglyceride lipases in cancer associated cachexia. Trends Mol Med 2013; 19: 292-301.
27. Young S G, Zechner R. Biochemistry and pathophysiology of intravascular and intracellular lipolysis. Genes Dev 2013; 27: 459-84.
28. Collins P, Bing C, McCulloch P, Williams G. Muscle UCP-3 mRNA levels are elevated in weight loss associated with gastrointestinal adenocarcinoma in humans. Br J Cancer 2002; 86: 372-5.
29. Constantinou C, Fontes de Oliveira C C, Mintzopoulos D, Busquets S, He J, Kesarwani M, et al. Nuclear magnetic resonance in conjunction with functional genomics suggests mitochondrial dysfunction in a murine model of cancer cachexia. Int J Mol Med 2011; 27: 15-24.
30. Shum A M, Mahendradatta T, Taylor R J, Painter A B, Moore M M, Tsoli M, et al. Disruption of MEF2C signaling and loss of sarcomeric and mitochondrial integrity in cancer-induced skeletal muscle wasting. Aging (Albany N.Y.) 2012; 4: 133-43.
31. Sherry B A, Gelin J, Fong Y, Marano M, Wei H, Cerami A, et al. Anticachectin/tumor necrosis factor-alpha antibodies attenuate development of cachexia in tumor models. FASEB J 1989; 3: 1956-62.
32. Strassmann G, Fong M, Kenney J S, Jacob C O. Evidence for the involvement of interleukin 6 in experimental cancer cachexia. J Clin Invest 1992; 89: 1681-4.

33. Bonetto A, Penna F, Minero V G, Reffo P, Bonelli G, Baccino F M, et al. Deacetylase inhibitors modulate the myostatin/follistatin axis without improving cachexia in tumor-bearing mice. Curr Cancer Drug Targets 2009; 9: 608-16.

34. Alamdari N, Aversa Z, Castillero E, Hasselgren P O. Acetylation and deacetylation—novel factors in muscle wasting. Metabolism 2013; 62: 1-11.

35. Senf S M, Sandesara P B, Reed S A, Judge A R. p300 Acetyltransferase activity differentially regulates the localization and activity of the FOXO homologues in skeletal muscle. Am J Physiol Cell Physiol 2011; 300: C1490-501.

36. Black B L, Olson E N. Transcriptional control of muscle development by myocyte enhancer factor-2 (MEF2) proteins. Annu Rev Cell Dev Biol 1998; 14: 167-96.

37. Moore-Carrasco R, Garcia-Martinez C, Busquets S, Ametller E, Barreiro E, Lopez-Soriano F J, et al. The AP-1/CJUN signaling cascade is involved in muscle differentiation: implications in muscle wasting during cancer cachexia. FEBS Lett 2006; 580: 691-6.

38. Der-Torossian H, Wysong A, Shadfar S, Willis M S, McDunn J, Couch M E. Metabolic derangements in the gastrocnemius and the effect of Compound A therapy in a murine model of cancer cachexia. J Cachexia Sarcopenia Muscle 2013; 4: 145-55.

39. Asp M L, Tian M, Wendel A A, Belury M A. Evidence for the contribution of insulin resistance to the development of cachexia in tumor-bearing mice. Int J Cancer 2010; 126: 756-63.

40. Honors M A, Kinzig K P. The role of insulin resistance in the development of muscle wasting during cancer cachexia. J Cachexia Sarcopenia Muscle 2012; 3: 5-11.

41. Moylan J S, Reid M B. Oxidative stress, chronic disease, and muscle wasting. Muscle Nerve 2007; 35: 411-29.

42. Chu P C, Kulp S K, Chen C S. Insulin-like growth factor-I receptor is suppressed through transcriptional repression and mRNA destabilization by a novel energy restriction-mimetic agent. Carcinogenesis 2013; 34: 2694-705.

Although the above description refers to particular aspects, it is to be understood that these aspects are merely illustrative. It will be apparent to those skilled in the art that various modifications and variations can be made to the methods described herein. Thus, it is intended that the present description include modifications and variations that are within the scope of the appended claims and their equivalents.

What is claimed is:

1. A method of restoring skeletal muscle weight in a mammal having cancer and loss of skeletal muscle weight associated with cancer-induced cachexia, comprising administering a composition comprising AR-42 to said mammal wherein the skeletal muscle weight is substantially restored compared to a mammal that does not receive AR-42.

2. The method of claim 1, wherein the cancer is selected from the group consisting of pancreatic, colon, head, neck, gastric, lung, and esophageal.

3. The method of claim 1, wherein the mammal is a human.

4. The method of claim 1, wherein AR-42 is administered in an amount of about 1 mg/kg to about 100 mg/kg of the mammal.

5. The method of claim 4, wherein AR-42 is administered at least once a day.

6. The method of claim 5, wherein AR-42 is administered twice a day in an amount of about 50 mg/kg of the mammal.

7. The method of claim 1, wherein levels of IL-6 are reduced by about 56% compared to a mammal that does not receive AR-42.

8. The method of claim 1, wherein levels of LIF are reduced by about 88% compared to a mammal that does not receive AR-42.

9. The method of claim 1, wherein expression of Atrogin-1 mRNA is restored to basal levels compared to a mammal that does not receive AR-42.

10. The method of claim 1, wherein expression of MuRF1 mRNA is restored to basal levels compared to a mammal that does not receive AR-42.

11. The method of claim 1, wherein expression of IL-6Rα mRNA is restored to basal levels compared to a mammal that does not receive AR-42.

12. The method of claim 1, wherein a cachexia-induced loss of adipose tissue is substantially restored compared to a mammal that does not receive AR-42.

13. The method of claim 1, wherein at least about 90% of said mammal's skeletal muscle weight is maintained over a period of time of at least fifteen days compared to a mammal that does not receive AR-42.

14. The method of claim 1, wherein the cancer is lung cancer.

15. The method of claim 1, wherein the cancer is prostate cancer.

* * * * *